US006207169B1

(12) United States Patent
Reed et al.

(10) Patent No.: US 6,207,169 B1
(45) Date of Patent: *Mar. 27, 2001

(54) COMPOUNDS AND METHODS FOR THE DIAGNOSIS AND TREATMENT OF EHRLICHIA INFECTION

(75) Inventors: Steven G. Reed, Bellevue; Michael J. Lodes, Seattle; Raymond L. Houghton, Bothell, all of WA (US)

(73) Assignee: Corixa Corporation, Seattle, WA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 08/975,762

(22) Filed: Nov. 20, 1997

Related U.S. Application Data

(63) Continuation-in-part of application No. 08/821,324, filed on Mar. 21, 1997.

(51) Int. Cl.[7] ................ A61K 9/02; C12Q 1/68; C07H 21/04
(52) U.S. Cl. ............ 424/234.1; 435/6; 536/23.7; 536/24.32; 536/24.33
(58) Field of Search ................ 435/6; 424/234.1; 536/23.7, 24.32, 24.33

(56) References Cited

FOREIGN PATENT DOCUMENTS

| WO 96/39484 | 12/1996 | (WO) | C12N/1/20 |
| WO 98/14584 | 4/1998 | (WO) | C12N/15/31 |
| WO 98/42740 | 10/1998 | (WO) | . |
| WO 98/49313 | 11/1998 | (WO) | . |

OTHER PUBLICATIONS

Asanovich et al., "Partial Characterization of Cloned Genes Encoding Immunoreactive Proteins of *Ehrlichia equi* and the Agent of Human Granulocytic Ehrlichiosis," *Abstracts of the General Meeting of the American Society for Microbiology*: Abstract No. D–22, 1996.

Dumler et al., "Serologic Cross–Reactions among *Ehrlichia equi*, *Ehrlichia phagocytophila*, and Human Granulocytic Ehrlichia," *Journal of Clinical Microbiology* 33(11): 1098–1103, 1995.

Palmer et al., "The Immunoprotective *Anaplasma marginale* Major Surface Protein 2 Is Encoded by a Polymorphic Multigene Family," *Infection And Immunity* 62(9): 3808–3816, 1994.

Magnarelli et al., "Coexistence of Antibodies to Tick–Borne Pathogens of Babesiosis Ehrlichiosis, and Lyme Borreliosis in Human Sera," *Journal Of Clinical Microbiology* 33(11): 3054–3057, 1995.

*Primary Examiner*—Rodney P. Swartz
(74) *Attorney, Agent, or Firm*—Seed Intellectual Property Law Group PLLC

(57) ABSTRACT

Compounds and methods for the diagnosis and treatment of Ehrlichia infection, in particular human granulocytic ehrlichiosis, are disclosed. The compounds provided include polypeptides that contain at least one antigenic portion of an Ehrlichia antigen and DNA sequences encoding such polypeptides. Pharmaceutical compositions and vaccines comprising such polypeptides or DNA sequences are also provided. Diagnostic kits containing such polypeptides or DNA sequences and a suitable detection reagent may be used for the detection of Ehrlichia infection in patients and biological samples. Antibodies directed against such polypeptides are also provided.

3 Claims, 5 Drawing Sheets

COMPOUNDS AND METHODS FOR THE DIAGNOSIS AND TREATMENT OF EHRLICHIA INFECTION

CROSS-REFERENCE TO RELATED APPLICATIONS

This application is a continuation-in-part of U.S. patent application Ser. No. 08/821,324, filed Mar. 21, 1997.

TECHNICAL FIELD

The present invention relates generally to the detection and treatment of Ehrlichia infection. In particular, the invention is related to polypeptides comprising an Ehrlichia antigen and the use of such polypeptides for the serodiagnosis and treatment of Human granulocytic ehrlichiosis (HGE).

BACKGROUND OF THE INVENTION

Human granulocytic ehrlichiosis (HGE) is an illness caused by a rodent bacterium which is generally transmitted to humans by the same tick that is responsible for the transmission of Lyme disease and babesiosis, thereby leading to the possibility of co-infection with Lyme disease, babesiosis and HGE from a single tick bite. The bacterium that causes HGE is believed to be quite widespread in parts of the northeastern United States and has been detected in parts of Europe. While the number of reported cases of HGE infection is increasing rapidly, infection with Ehrlichia, including co-infection with Lyme disease, often remains undetected for extended periods of time. HGE is a potentially fatal disease, with the risk of death increasing if appropriate treatment is delayed beyond the first few days after symptoms occur. In contrast, deaths from Lyme disease and babesiosis are relatively rare.

The preferred treatments for HGE, Lyme disease and babesiosis are different, with penicillins, such as doxycycline and amoxicillin, being most effective in treating Lyme disease, anti-malarial drugs being preferred for the treatment of babesiosis and tetracycline being preferred for the treatment of ehrlichiosis. Accurate and early diagnosis of Ehrlichia infection is thus critical but methods currently employed for diagnosis are problematic.

All three tick-borne illnesses share the same flu-like symptoms of muscle aches, fever, headaches and fatigue, thus making clinical diagnosis difficult. Microscopic analysis of blood samples may provide false-negative results when patients are first seen in the clinic. The only tests currently available for the diagnosis of HGE infection are indirect fluorescent antibody staining methods for total immunoglobulins to Ehrlichia causative agents and polymerase chain reaction (PCR) amplification tests. Such methods are time-consuming, labor-intensive and expensive. There thus remains a need in the art for improved methods for the detection of Ehrlichia infection, particularly as related to HGE. The present invention fulfills this need and further provides other related advantages.

SUMMARY OF THE INVENTION

The present invention provides compositions and methods for the diagnosis and treatment of Ehrlichia infection and, in particular, for the diagnosis and treatment of HGE. In one aspect, polypeptides are provided comprising an immunogenic portion of an Ehrlichia antigen, particularly one associated with HGE, or a variant of such an antigen that differs only in conservative substitutions and/or modifications. In one embodiment, the antigen comprises an amino acid sequence encoded by a DNA sequence selected from the group consisting of (a) sequences recited in SEQ ID NO: 1–3, 5, 7, 16, 20, 34, 39–49; (b) the complements of said sequences; and (c) sequences that hybridize to a sequence of (a) or (b) under moderately stringent conditions.

In another aspect, the present invention provides an antigenic epitope of an Ehrlichia antigen comprising an amino acid sequence selected from the group consisting of sequences recited in SEQ ID NO: 30 and 51, together with polypeptides comprising at least two such antigenic epitopes, the epitopes being contiguous.

In a related aspect, DNA sequences encoding the above polypeptides, recombinant expression vectors comprising one or more of these DNA sequences and host cells transformed or transfected with such expression vectors are also provided.

In another aspect, the present invention provides fusion proteins comprising either a first and a second inventive polypeptide, a first and a second inventive antigenic epitope, or, alternatively, an inventive polypeptide and an inventive antigenic epitope.

In further aspects of the subject invention, methods and diagnostic kits are provided for detecting Ehrlichia infection in a patient. In one embodiment, the method comprises: (a) contacting a biological sample with at least one of the above polypeptides, antigenic epitopes or fusion proteins; and (b) detecting in the sample the presence of antibodies that bind to the polypeptide, antigenic epitope or fusion protein, thereby detecting Ehrlichia infection in the biological sample. Suitable biological samples include whole blood, sputum, serum, plasma, saliva, cerebrospinal fluid and urine. The diagnostic kits comprise one or more of the above polypeptides, antigenic epitopes or fusion proteins in combination with a detection reagent.

The present invention also provides methods for detecting Ehrlichia infection comprising: (a) obtaining a biological sample from a patient; (b) contacting the sample with at least two oligonucleotide primers in a polymerase chain reaction, at least one of the oligonucleotide primers being specific for a DNA sequence encoding the above polypeptides; and (c) detecting in the sample a DNA sequence that amplifies in the presence of the oligonucleotide primers. In one embodiment, the oligonucleotide primer comprises at least about 10 contiguous nucleotides of a DNA sequence encoding the above polypeptides.

In a further aspect, the present invention provides a method for detecting Ehrlichia infection in a patient comprising: (a) obtaining a biological sample from the patient; (b) contacting the sample with an oligonucleotide probe specific for a DNA sequence encoding the above polypeptides; and (c) detecting in the sample a DNA sequence that hybridizes to the oligonucleotide probe. In one embodiment, the oligonucleotide probe comprises at least about 15 contiguous nucleotides of a DNA sequence encoding the above polypeptides.

In yet another aspect, the present invention provides antibodies, both polyclonal and monoclonal, that bind to the polypeptides described above, as well as methods for their use in the detection of Ehrlichia infection.

In further aspects, the present invention provides methods for detecting either Ehrlichia infection, Lyme disease or *B. microti* infection in a patient. Such inventive methods comprise (a) obtaining a biological sample from the patient; (b) contacting the sample with (i) at least one of the inventive polypeptides, antigenic epitopes or fusion proteins, (ii) a known Lyme disease antigen and (iii) a known *B. microti* antigen; and (b) detecting in the sample the presence of antibodies that bind to the inventive polypeptide, antigenic epitope or fusion protein, the known Lyme disease antigen or the known *B. microti* antigen, thereby detecting either Ehrlichia infection, Lyme disease or *B. microti* infection in the patient.

Within other aspects, the present invention provides pharmaceutical compositions that comprise one or more of the above polypeptides or antigenic epitopes, or a DNA molecule encoding such polypeptides, and a physiologically acceptable carrier. The invention also provides vaccines comprising one or more of the inventive polypeptides or antigenic epitopes and a non-specific immune response enhancer, together with vaccines comprising one or more DNA sequences encoding such polypeptides and a non-specific immune response enhancer.

In yet another aspect, methods are provided for inducing protective immunity in a patient, comprising administering to a patient an effective amount of one or more of the above pharmaceutical compositions or vaccines.

These and other aspects of the present invention will become apparent upon reference to the following detailed description and attached drawings. All references disclosed herein are hereby incorporated by reference in their entirety as if each was incorporated individually.

DETAILED DESCRIPTION OF THE INVENTION

Figure 1:
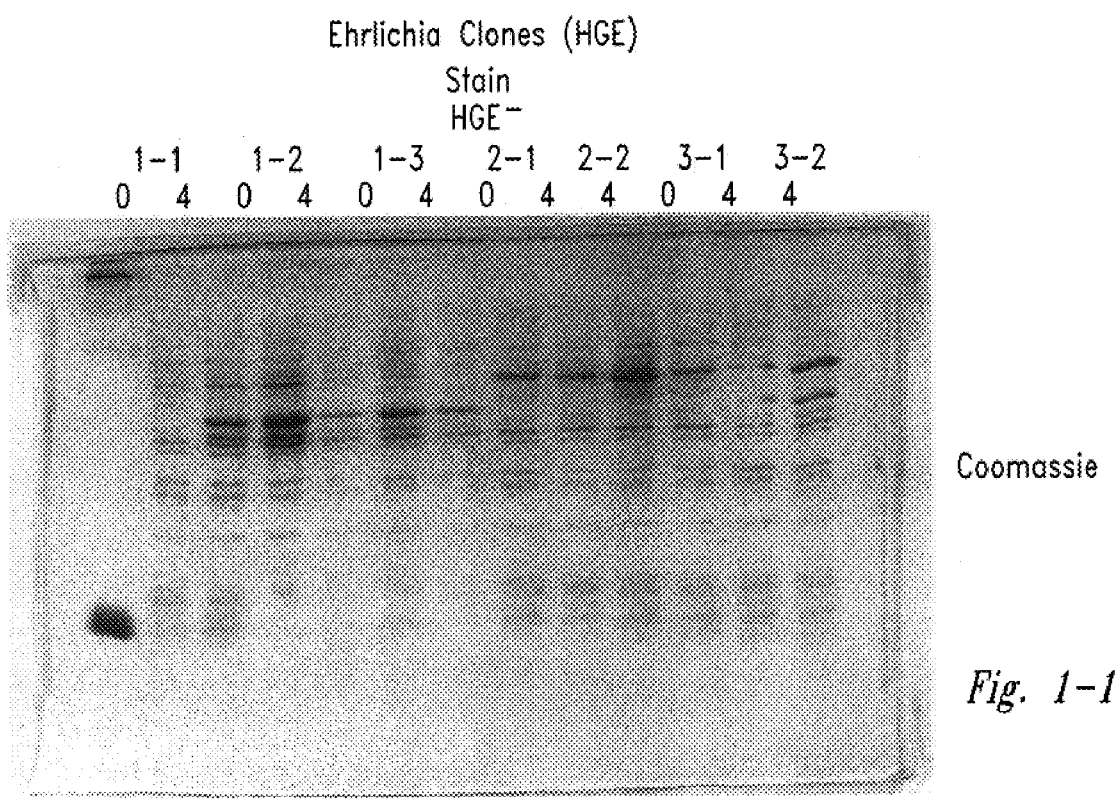
FIG. 1 shows the results of Western blot analysis of representative Ehrlichia antigens of the present invention.
Figures 1, 2:
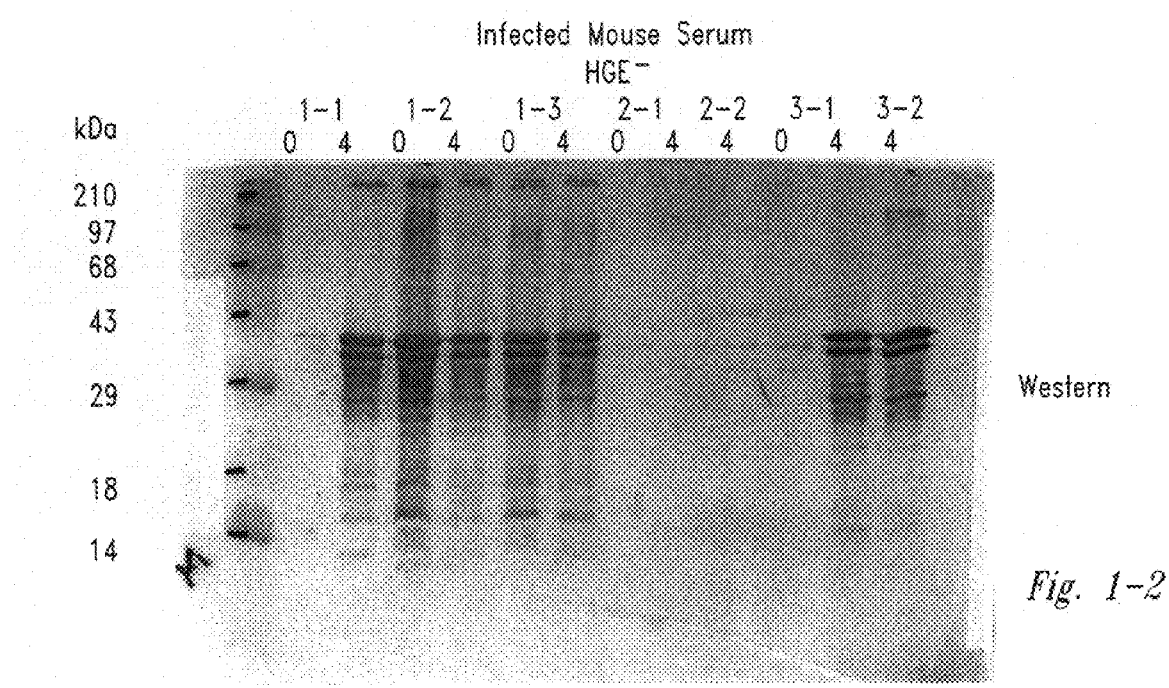
Figures 1, 2, 3:
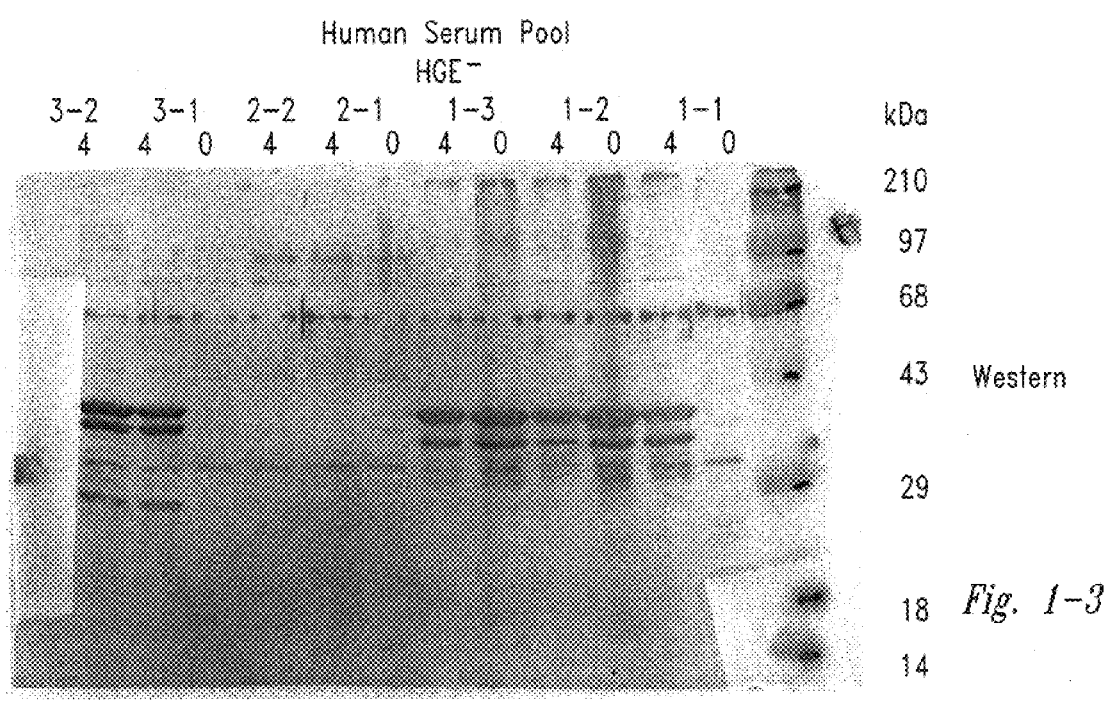

As noted above, the present invention is generally directed to compositions and methods for the diagnosis and treatment of Ehrlichia infection, in particular HGE. In one aspect, the compositions of the subject invention include polypeptides that comprise at least one immunogenic portion of an Ehrlichia antigen, or a variant of such an antigen that differs only in conservative substitutions and/or modifications.

As used herein, the term "polypeptide" encompasses amino acid chains of any length, including full length proteins (i.e., antigens), wherein the amino acid residues are linked by covalent peptide bonds. Thus, a polypeptide comprising an immunogenic portion of one of the above antigens may consist entirely of the immunogenic portion, or may contain additional sequences. The additional sequences may be derived from the native Ehrlichia antigen or may be heterologous, and such sequences may (but need not) be immunogenic.

An "immunogenic portion" of an antigen is a portion that is capable of reacting with sera obtained from an Ehrlichia-infected individual (i.e., generates an absorbance reading with sera from infected individuals that is at least three standard deviations above the absorbance obtained with sera from uninfected individuals, in a representative ELISA assay described herein). Polypeptides comprising at least an immunogenic portion of one or more Ehrlichia antigens as described herein may generally be used, alone or in combination, to detect HGE in a patient.

The compositions and methods of this invention also encompass variants of the above polypeptides. A "variant," as used herein, is a polypeptide that differs from the native antigen only in conservative substitutions and/or modifications, such that the antigenic properties of the polypeptide are retained. Such variants may generally be identified by modifying one of the above polypeptide sequences, and evaluating the antigenic properties of the modified polypeptide using, for example, the representative procedures described herein.

A "conservative substitution" is one in which an amino acid is substituted for another amino acid that has similar properties, such that one skilled in the art of peptide chemistry would expect the secondary structure and hydropathic nature of the polypeptide to be substantially unchanged. In general, the following groups of amino acids represent conservative changes: (1) ala, pro, gly, glu, asp, gln, asn, ser, thr; (2) cys, ser, tyr, thr; (3) val, ile, leu, met, ala, phe; (4) lys, arg, his; and (5) phe, tyr, trp, his.

Variants may also (or alternatively) be modified by, for example, the deletion or addition of amino acids that have minimal influence on the antigenic properties, secondary structure and hydropathic nature of the polypeptide. For example, a polypeptide may be conjugated to a signal (or leader) sequence at the N-terminal end of the protein which co-translationally or post-translationally directs transfer of the protein. The polypeptide may also be conjugated to a linker or other sequence for ease of synthesis, purification or identification of the polypeptide (e.g., poly-His), or to enhance binding of the polypeptide to a solid support. For example, a polypeptide may be conjugated to an immunoglobulin Fc region.

In specific embodiments, the subject invention discloses polypeptides comprising at least an immunogenic portion of an Ehrlichia antigen (or a variant of such an antigen), that comprises one or more of the amino acid sequences encoded by (a) a DNA sequence selected from the group consisting of SEQ ID NO: 1–3, 5, 7, 16, 20, 34, 39–49, (b) the complements of such DNA sequences or (c) DNA sequences substantially homologous to a sequence in (a) or (b).

The Ehrlichia antigens provided by the present invention include variants that are encoded by DNA sequences which are substantially homologous to one or more of the DNA sequences specifically recited herein. "Substantial homology," as used herein, refers to DNA sequences that are capable of hybridizing under moderately stringent conditions. Suitable moderately stringent conditions include pre-washing in a solution of 5× SSC, 0.5% SDS, 1.0 mM EDTA (pH 8.0); hybridizing at 50° C.–65° C., 5× SSC, overnight or, in the event of cross-species homology, at 45° C. with 0.5× SSC; followed by washing twice at 65° C. for 20 minutes with each of 2×, 0.5× and 0.2× SSC containing 0.1% SDS. Such hybridizing DNA sequences are also within the scope of this invention, as are nucleotide sequences that, due to code degeneracy, encode an immunogenic polypeptide that is encoded by a hybridizing DNA sequence.

In general, Ehrlichia antigens, and DNA sequences encoding such antigens, may be prepared using any of a variety of procedures. For example, DNA molecules encoding Ehrlichia antigens may be isolated from an Ehrlichia genomic or cDNA expression library by screening with sera from HGE-infected individuals as described below in Example 1, and sequenced using techniques well known to those of skill in the art. DNA molecules encoding Ehrlichia antigens may also be isolated by screening an appropriate Ehrlichia expression library with anti-sera (e.g., rabbit) raised specifically against Ehrlichia antigens.

Antigens may be induced from such clones and evaluated for a desired property, such as the ability to react with sera obtained from an HGE-infected individual as described herein. Alternatively, antigens may be produced recombinantly, as described below, by inserting a DNA sequence that encodes the antigen into an expression vector and expressing the antigen in an appropriate host. Antigens may be partially sequenced using, for example, traditional Edman chemistry. See Edman and Berg, *Eur. J Biochem.* 80:116–132, 1967.

DNA sequences encoding antigens may also be obtained by screening an appropriate Ehrlichia cDNA or genomic DNA library for DNA sequences that hybridize to degenerate oligonucleotides derived from partial amino acid sequences of isolated antigens. Degenerate oligonucleotide sequences for use in such a screen may be designed and synthesized, and the screen may be performed, as described (for example) in Sambrook et al., *Molecular Cloning: A Laboratory Manual,* Cold Spring Harbor Laboratories, Cold Spring Harbor, N.Y. (and references cited therein). Polymerase chain reaction (PCR) may also be employed, using the above oligonucleotides in methods well known in the art, to isolate a nucleic acid probe from a cDNA or genomic library. The library screen may then be performed using the isolated probe.

Synthetic polypeptides having fewer than about 100 amino acids, and generally fewer than about 50 amino acids, may be generated using techniques well known in the art. For example, such polypeptides may be synthesized using any of the commercially available solid-phase techniques, such as the Merrifield solid-phase synthesis method, where amino acids are sequentially added to a growing amino acid chain. See Merrifield, *J. Am. Chem. Soc.* 85:2149–2146, 1963. Equipment for automated synthesis of polypeptides is commercially available from suppliers such as Perkin Elmer/Applied BioSystems Division, Foster City, Calif., and may be operated according to the manufacturer's instructions.

Immunogenic portions of Ehrlichia antigens may be prepared and identified using well known techniques, such as those summarized in Paul, *Fundamental Immunology,* 3d ed., Raven Press, 1993, pp. 243–247 and references cited therein. Such techniques include screening polypeptide portions of the native antigen for immunogenic properties. The representative ELISAs described herein may generally be employed in these screens. An immunogenic portion of a polypeptide is a portion that, within such representative assays, generates a signal in such assays that is substantially similar to that generated by the full length antigen. In other words, an immunogenic portion of an Ehrlichia antigen generates at least about 20%, and preferably about 100%, of the signal induced by the full length antigen in a model ELISA as described herein.

Portions and other variants of Ehrlichia antigens may be generated by synthetic or recombinant means. Variants of a native antigen may generally be prepared using standard mutagenesis techniques, such as oligonucleotide-directed site-specific mutagenesis. Sections of the DNA sequence may also be removed using standard techniques to permit preparation of truncated polypeptides.

Recombinant polypeptides containing portions and/or variants of a native antigen may be readily prepared from a DNA sequence encoding the polypeptide using a variety of techniques well known to those of ordinary skill in the art. For example, supernatants from suitable host/vector systems which secrete recombinant protein into culture media may be first concentrated using a commercially available filter. Following concentration, the concentrate may be applied to a suitable purification matrix such as an affinity matrix or an ion exchange resin. Finally, one or more reverse phase HPLC steps can be employed to further purify a recombinant protein.

Any of a variety of expression vectors known to those of ordinary skill in the art may be employed to express recombinant polypeptides as described herein. Expression may be achieved in any appropriate host cell that has been transformed or transfected with an expression vector containing a DNA molecule that encodes a recombinant polypeptide. Suitable host cells include prokaryotes, yeast and higher eukaryotic cells. Preferably, the host cells employed are *E. coli,* yeast or a mammalian cell line, such as COS or CHO. The DNA sequences expressed in this manner may encode naturally occurring antigens, portions of naturally occurring antigens, or other variants thereof.

In another aspect, the present invention provides antigenic epitopes of an Ehrlichia antigen or epitope repeat sequences, as well as polypeptides comprising at least two such contiguous antigenic epitopes. As used herein, an "epitope" is a portion of an antigen that reacts with sera from Ehrlichia-infected individuals (i.e. an epitope is specifically bound by one or more antibodies present in such sera). As discussed above, epitopes of the antigens described in the present application may be generally identified using techniques well known to those of skill in the art.

In specific embodiments, antigenic epitopes of the present invention comprise an amino acid sequence selected from the group consisting of sequence recited in SEQ ID NO: 30 and 51. As discussed in more detail below, antigenic epitopes provided herein may be employed in the diagnosis and treatment of Ehrlichia infection, either alone or in combination with other Ehrlichia antigens or antigenic epitopes. Antigenic epitopes and polypeptides comprising such epitopes may be prepared by synthetic means, as described generally above and in detail in Example 3.

In general, regardless of the method of preparation, the polypeptides and antigenic epitopes disclosed herein are prepared in substantially pure form. Preferably, the polypeptides and antigenic epitopes are at least about 80% pure, more preferably at least about 90% pure and most preferably at least about 99% pure.

In a further aspect, the present invention provides fusion proteins comprising either a first and a second inventive polypeptide, a first and a second inventive antigenic epitope, or an inventive polypeptide and an antigenic epitope of the present invention, together with variants of such fusion proteins. The fusion proteins of the present invention may also include a linker peptide between the polypeptides or antigenic epitopes.

A DNA sequence encoding a fusion protein of the present invention may be constructed using known recombinant DNA techniques to assemble separate DNA sequences encoding, for example, the first and second polypeptides, into an appropriate expression vector. The 3' end of a DNA sequence encoding the first polypeptide is ligated, with or without a peptide linker, to the 5' end of a DNA sequence encoding the second polypeptide so that the reading frames of the sequences are in phase to permit mRNA translation of the two DNA sequences into a single fusion protein that retains the biological activity of both the first and the second polypeptides.

A peptide linker sequence may be employed to separate the first and the second polypeptides by a distance sufficient to ensure that each polypeptide folds into its secondary and tertiary structures. Such a peptide linker sequence is incorporated into the fusion protein using standard techniques well known in the art. Suitable peptide linker sequences may be chosen based on the following factors: (1) their ability to adopt a flexible extended conformation; (2) their inability to adopt a secondary structure that could interact with functional epitopes on the first and second polypeptides; and (3) the lack of hydrophobic or charged residues that might react with the polypeptide functional epitopes. Preferred peptide linker sequences contain Gly, Asn and Ser residues. Other near neutral amino acids, such as Thr and Ala may also be used in the linker sequence. Amino acid sequences which may be usefully employed as linkers include those disclosed in Maratea et al., *Gene* 40:39–46, 1985; Murphy et al., *Proc. Natl. Acad. Sci. USA* 83:8258–8562, 1986; U.S. Pat. No. 4,935,233 and U.S. Pat. No. 4,751,180. The linker sequence may be from 1 to about 50 amino acids in length. As an alternative to the use of a peptide linker sequence (when desired), one can utilize non-essential N-terminal amino acid regions (when present) on the first and second polypeptides to separate the functional domains and prevent steric hindrance.

In another aspect, the present invention provides methods for using the polypeptides and antigenic epitopes described above to diagnose Ehrlichia infection, in particular HGE. In this aspect, methods are provided for detecting Ehrlichia infection in a biological sample, using one or more of the above polypeptides and antigenic epitopes, either alone or in combination. For clarity, the term "polypeptide" will be used when describing specific embodiments of the inventive diagnostic methods. However, it will be clear to one of skill in the art that the antigenic epitopes and fusion proteins of the present invention may also be employed in such methods.

As used herein, a "biological sample" is any antibody-containing sample obtained from a patient. Preferably, the sample is whole blood, sputum, serum, plasma, saliva, cerebrospinal fluid or urine. More preferably, the sample is a blood, serum or plasma sample obtained from a patient. The polypeptides are used in an assay, as described below, to determine the presence or absence of antibodies to the polypeptide(s) in the sample, relative to a predetermined cut-off value. The presence of such antibodies indicates previous sensitization to Ehrlichia antigens which may be indicative of HGE.

In embodiments in which more than one polypeptide is employed, the polypeptides used are preferably complementary (ie., one component polypeptide will tend to detect infection in samples where the infection would not be detected by another component polypeptide). Complementary polypeptides may generally be identified by using each polypeptide individually to evaluate serum samples obtained from a series of patients known to be infected with HGE. After determining which samples test positive (as described below) with each polypeptide, combinations of two or more polypeptides may be formulated that are capable of detecting infection in most, or all, of the samples tested.

A variety of assay formats are known to those of ordinary skill in the art for using one or more polypeptides to detect antibodies in a sample. See, e.g., Harlow and Lane, *Antibodies: A Laboratory Manual,* Cold Spring Harbor Laboratory, 1988, which is incorporated herein by reference. In a preferred embodiment, the assay involves the use of polypeptide immobilized on a solid support to bind to and remove the antibody from the sample. The bound antibody may then be detected using a detection reagent that contains a reporter group. Suitable detection reagents include antibodies that bind to the antibody/polypeptide complex and free polypeptide labeled with a reporter group (e.g., in a semi-competitive assay). Alternatively, a competitive assay may be utilized, in which an antibody that binds to the polypeptide is labeled with a reporter group and allowed to bind to the immobilized antigen after incubation of the antigen with the sample. The extent to which components of the sample inhibit the binding of the labeled antibody to the polypeptide is indicative of the reactivity of the sample with the immobilized polypeptide.

The solid support may be any solid material known to those of ordinary skill in the art to which the antigen may be attached. For example, the solid support may be a test well in a microtiter plate, or a nitrocellulose or other suitable membrane. Alternatively, the support may be a bead or disc, such as glass, fiberglass, latex or a plastic material such as polystyrene or polyvinylchloride. The support may also be a magnetic particle or a fiber optic sensor, such as those disclosed, for example, in U.S. Pat. No. 5,359,681.

The polypeptides may be bound to the solid support using a variety of techniques known to those of ordinary skill in the art. In the context of the present invention, the term "bound" refers to both noncovalent association, such as adsorption, and covalent attachment (which may be a direct linkage between the antigen and functional groups on the support or may be a linkage by way of a cross-linking agent). Binding by adsorption to a well in a microtiter plate or to a membrane is preferred. In such cases, adsorption may be achieved by contacting the polypeptide, in a suitable buffer, with the solid support for a suitable amount of time. The contact time varies with temperature, but is typically between about 1 hour and 1 day. In general, contacting a well of a plastic microtiter plate (such as polystyrene or polyvinylchloride) with an amount of polypeptide ranging from about 10 ng to about 1 $\mu$g, and preferably about 100 ng, is sufficient to bind an adequate amount of antigen.

Covalent attachment of polypeptide to a solid support may generally be achieved by first reacting the support with a bifunctional reagent that will react with both the support and a functional group, such as a hydroxyl or amino group, on the polypeptide. For example, the polypeptide may be bound to supports having an appropriate polymer coating using benzoquinone or by condensation of an aldehyde group on the support with an amine and an active hydrogen on the polypeptide (see, e.g., Pierce Immunotechnology Catalog and Handbook, 1991, at A12–A13).

In certain embodiments, the assay is an enzyme linked immunosorbent assay (ELISA). This assay may be performed by first contacting a polypeptide antigen that has been immobilized on a solid support, commonly the well of a microtiter plate, with the sample, such that antibodies to the polypeptide within the sample are allowed to bind to the immobilized polypeptide. Unbound sample is then removed from the immobilized polypeptide and a detection reagent capable of binding to the immobilized antibody-polypeptide complex is added. The amount of detection reagent that remains bound to the solid support is then determined using a method appropriate for the specific detection reagent.

More specifically, once the polypeptide is immobilized on the support as described above, the remaining protein binding sites on the support are typically blocked. Any suitable blocking agent known to those of ordinary skill in the art, such as bovine serum albumin (BSA) or Tween 20™ (Sigma Chemical Co., St. Louis, Mo.) may be employed. The immobilized polypeptide is then incubated with the sample, and antibody is allowed to bind to the antigen. The sample may be diluted with a suitable diluent, such as phosphate-buffered saline (PBS) prior to incubation. In general, an appropriate contact time (i.e., incubation time) is that period of time that is sufficient to detect the presence of antibody within an HGE-infected sample. Preferably, the contact time is sufficient to achieve a level of binding that is at least 95% of that achieved at equilibrium between bound and unbound antibody. Those of ordinary skill in the art will recognize that the time necessary to achieve equilibrium may be readily determined by assaying the level of binding that occurs over a period of time. At room temperature, an incubation time of about 30 minutes is generally sufficient.

Unbound sample may then be removed by washing the solid support with an appropriate buffer, such as PBS containing 0.1% Tween 20™. Detection reagent may then be added to the solid support. An appropriate detection reagent is any compound that binds to the immobilized antibody-polypeptide complex and that can be detected by any of a variety of means known to those in the art. Preferably, the detection reagent contains a binding agent (such as, for example, Protein A, Protein G, immunoglobulin, lectin or free antigen) conjugated to a reporter group. Preferred reporter groups include enzymes (such as horseradish peroxidase), substrates, cofactors, inhibitors, dyes, radionuclides, luminescent groups, fluorescent groups and biotin. The conjugation of binding agent to reporter group may be achieved using standard methods known to those of ordinary skill in the art. Common binding agents may also be purchased conjugated to a variety of reporter groups from many commercial sources (e.g., Zymed Laboratories, San Francisco, Calif., and Pierce, Rockford, Ill.).

The detection reagent is then incubated with the immobilized antibody-polypeptide complex for an amount of time sufficient to detect the bound antibody. An appropriate amount of time may generally be determined from the manufacturers instructions or by assaying the level of binding that occurs over a period of time. Unbound detection reagent is then removed and bound detection reagent is detected using the reporter group. The method employed for detecting the reporter group depends upon the nature of the reporter group. For radioactive groups, scintillation counting or autoradiographic methods are generally appropriate. Spectroscopic methods may be used to detect dyes, luminescent groups and fluorescent groups. Biotin may be detected using avidin, coupled to a different reporter group (commonly a radioactive or fluorescent group or an enzyme). Enzyme reporter groups may generally be detected by the addition of substrate (generally for a specific period of time), followed by spectroscopic or other analysis of the reaction products.

To determine the presence or absence of anti-Ehrlichia antibodies in the sample, the signal detected from the reporter group that remains bound to the solid support is generally compared to a signal that corresponds to a predetermined cut-off value. In one preferred embodiment, the cut-off value is the average mean signal obtained when the immobilized antigen is incubated with samples from an uninfected patient. In general, a sample generating a signal that is three standard deviations above the predetermined cut-off value is considered positive for HGE. In an alternate preferred embodiment, the cut-off value is determined using a Receiver Operator Curve, according to the method of Sackett et al., *Clinical Epidemiology: A Basic Science for Clinical Medicine,* Little Brown and Co., 1985, pp. 106–107. Briefly, in this embodiment, the cut-off value may be determined from a plot of pairs of true positive rates (i.e., sensitivity) and false positive rates (100%-specificity) that correspond to each possible cut-off value for the diagnostic test result. The cut-off value on the plot that is the closest to the upper left-hand corner (ie., the value that encloses the largest area) is the most accurate cut-off value, and a sample generating a signal that is higher than the cut-off value determined by this method may be considered positive. Alternatively, the cut-off value may be shifted to the left along the plot, to minimize the false positive rate, or to the right, to minimize the false negative rate. In general, a sample generating a signal that is higher than the cut-off value determined by this method is considered positive for HGE.

In a related embodiment, the assay is performed in a rapid flow-through or strip test format, wherein the antigen is immobilized on a membrane, such as nitrocellulose. In the flow-through test, antibodies within the sample bind to the immobilized polypeptide as the sample passes through the membrane. A detection reagent (e.g., protein A-colloidal gold) then binds to the antibody-polypeptide complex as the solution containing the detection reagent flows through the membrane. The detection of bound detection reagent may then be performed as described above. In the strip test format, one end of the membrane to which polypeptide is bound is immersed in a solution containing the sample. The sample migrates along the membrane through a region containing detection reagent and to the area of immobilized polypeptide. Concentration of detection reagent at the polypeptide indicates the presence of anti-Ehrlichia antibodies in the sample. Typically, the concentration of detection reagent at that site generates a pattern, such as a line, that can be read visually. The absence of such a pattern indicates a negative result. In general, the amount of polypeptide immobilized on the membrane is selected to generate a visually discernible pattern when the biological sample contains a level of antibodies that would be sufficient to generate a positive signal in an ELISA, as discussed above. Preferably, the amount of polypeptide immobilized on the membrane ranges from about 25 ng to about 1 $\mu$g, and more preferably from about 50 ng to about 500 ng. Such tests can typically be performed with a very small amount (e.g., one drop) of patient serum or blood.

Of course, numerous other assay protocols exist that are suitable for use with the polypeptides and antigenic epitopes of the present invention. The above descriptions are intended to be exemplary only.

The inventive polypeptides may be employed in combination with known Lyme disease and/or *B. microti* antigens to diagnose the presence of either Ehrlichia infection, Lyme disease and/or *B. microti* infection, using either the assay formats described herein or other assay protocols. One example of an alternative assay protocol which may be usefully employed in such methods is a Western blot, wherein the proteins present in a biological sample are separated on a gel, prior to exposure to a binding agent. Such techniques are well known to those of skill in the art. Lyme disease antigens which may be usefully employed in such methods are well known to those of skill in the art and include, for example, those described by Magnarelli, L. et al. (J. Clin. Microbiol., 1996 34:237–240), Magnarelli, L. (Rheum. Dis. Clin. North Am., 1989, 15:735–745) and Cutler, S. J. (J. Clin. Pathol., 1989, 42:869–871). *B. microti* antigens which may be usefully employed in the inventive methods include those described in U.S. patent application Ser. No. 08/845,258, filed Apr. 24, 1997, the disclosure of which is hereby incorporated by reference.

In yet another aspect, the present invention provides antibodies to the polypeptides and antigenic epitopes of the present invention. Antibodies may be prepared by any of a variety of techniques known to those of ordinary skill in the art. See, e.g, Harlow and Lane, *Antibodies: A Laboratory Manual,* Cold Spring Harbor Laboratory, Cold Spring Harbor, N.Y., 1988. In one such technique, an immunogen comprising the antigenic polypeptide or epitope is initially injected into any of a wide variety of mammals (e.g., mice, rats, rabbits, sheep and goats). The polypeptides and antigenic epitopes of this invention may serve as the immunogen without modification. Alternatively, particularly for relatively short polypeptides, a superior immune response may be elicited if the polypeptide is joined to a carrier protein, such as bovine serum albumin or keyhole limpet hemocyanin. The immunogen is injected into the animal host, preferably according to a predetermined schedule incorporating one or more booster immunizations, and the animals are bled periodically. Polyclonal antibodies specific for the polypeptide or antigenic epitope may then be purified from such antisera by, for example, affinity chromatography using the polypeptide coupled to a suitable solid support.

Monoclonal antibodies specific for the antigenic polypeptide or epitope of interest may be prepared, for example, using the technique of Kohler and Milstein, *Eur. J Immunol.* 6:511–519, 1976, and improvements thereto. Briefly, these methods involve the preparation of immortal cell lines capable of producing antibodies having the desired specificity (i.e., reactivity with the polypeptide or antigenic epitope of interest). Such cell lines may be produced, for example, from spleen cells obtained from an animal immunized as described above. The spleen cells are then immortalized by, for example, fusion with a myeloma cell fusion partner, preferably one that is syngeneic with the immunized animal. A variety of fusion techniques may be employed. For example, the spleen cells and myeloma cells may be combined with a nonionic detergent for a few minutes and then plated at low density on a selective medium that supports the growth of hybrid cells, but not myeloma cells. A preferred selection technique uses HAT (hypoxanthine, aminopterin, thymidine) selection. After a sufficient time, usually about 1 to 2 weeks, colonies of hybrids are observed. Single colonies are selected and tested for binding activity against the polypeptide or antigenic epitope. Hybridomas having high reactivity and specificity are preferred.

Monoclonal antibodies may be isolated from the supernatants of growing hybridoma colonies. In addition, various techniques may be employed to enhance the yield, such as injection of the hybridoma cell line into the peritoneal cavity of a suitable vertebrate host, such as a mouse. Monoclonal antibodies may then be harvested from the ascites fluid or the blood. Contaminants may be removed from the antibodies by conventional techniques, such as chromatography, gel filtration, precipitation, and extraction. The polypeptides or antigenic epitopes of this invention may be used in the purification process in, for example, an affinity chromatography step.

Antibodies may be used in diagnostic tests to detect the presence of Ehrlichia antigens using assays similar to those detailed above and other techniques well known to those of skill in the art, thereby providing a method for detecting Ehrlichia infection in a patient.

Diagnostic reagents of the present invention may also comprise DNA sequences encoding one or more of the above polypeptides, or one or more portions thereof. For example, at least two oligonucleotide primers may be employed in a polymerase chain reaction (PCR) based assay to amplify Ehrlichia-specific cDNA derived from a biological sample, wherein at least one of the oligonucleotide primers is specific for a DNA molecule encoding a polypeptide of the present invention. The presence of the amplified cDNA is then detected using techniques well known in the art, such as gel electrophoresis. Similarly, oligonucleotide probes specific for a DNA molecule encoding a polypeptide of the present invention may be used in a hybridization assay to detect the presence of an inventive polypeptide in a biological sample.

As used herein, the term "oligonucleotide primer/probe specific for a DNA molecule" means an oligonucleotide sequence that has at least about 80%, preferably at least about 90% and more preferably at least about 95%, identity to the DNA molecule in question. Oligonucleotide primers and/or probes which may be usefully employed in the inventive diagnostic methods preferably have at least about 10–40 nucleotides. In a preferred embodiment, the oligonucleotide primers comprise at least about 10 contiguous nucleotides of a DNA molecule encoding one of the polypeptides disclosed herein. Preferably, oligonucleotide probes for use in the inventive diagnostic methods comprise at least about 15 contiguous oligonucleotides of a DNA molecule encoding one of the polypeptides disclosed herein. Techniques for both PCR based assays and hybridization assays are well known in the art (see, for example, Mullis et al. *Ibid;* Ehrlich, *Ibid*). Primers or probes may thus be used to detect Ehrlichia-specific sequences in biological samples. DNA probes or primers comprising oligonucleotide sequences described above may be used alone or in combination with each other.

In another aspect, the present invention provides methods for using one or more of the above polypeptides, antigenic epitopes or fusion proteins (or DNA molecules encoding such polypeptides) to induce protective immunity against Ehrlichia infection in a patient. As used herein, a "patient" refers to any warm-blooded animal, preferably a human. A patient may be afflicted with a disease, or may be free of detectable disease and/or infection. In other words, protective immunity may be induced to prevent or treat Ehrlichia infection, specifically HGE.

In this aspect, the polypeptide, antigenic epitope, fusion protein or DNA molecule is generally present within a pharmaceutical composition or a vaccine. Pharmaceutical compositions may comprise one or more polypeptides, each of which may contain one or more of the above sequences (or variants thereof), and a physiologically acceptable carrier. Vaccines may comprise one or more of the above polypeptides and a non-specific immune response enhancer, such as an adjuvant or a liposome (into which the polypeptide is incorporated). Such pharmaceutical compositions and vaccines may also contain other Ehrlichia antigens, either incorporated into a combination polypeptide or present within a separate polypeptide.

Alternatively, a vaccine may contain DNA encoding one or more polypeptides, antigenic epitopes or fusion proteins as described above, such that the polypeptide is generated in situ. In such vaccines, the DNA may be present within any of a variety of delivery systems known to those of ordinary skill in the art, including nucleic acid expression systems, bacterial and viral expression systems. Appropriate nucleic acid expression systems contain the necessary DNA sequences for expression in the patient (such as a suitable promoter and terminating signal). Bacterial delivery systems involve the administration of a bacterium (such as Bacillus-Calmette-Guerrin) that expresses an immunogenic portion of the polypeptide on its cell surface. In a preferred embodiment, the DNA may be introduced using a viral expression system (e.g., vaccinia or other pox virus, retrovirus, or adenovirus), which may involve the use of a non-pathogenic (defective), virus. Techniques for incorporating DNA into such expression systems are well known to those of ordinary skill in the art. The DNA may also be "naked," as described, for example, in Ulmer et al., *Science* 259:1745–1749, 1993 and reviewed by Cohen, *Science* 259:1691–1692, 1993. The uptake of naked DNA may be increased by coating the DNA onto biodegradable beads, which are efficiently transported into the cells.

In a related aspect, a DNA vaccine as described above may be administered simultaneously with or sequentially to either a polypeptide of the present invention or a known Ehrlichia antigen. For example, administration of DNA encoding a polypeptide of the present invention, either "naked" or in a delivery system as described above, may be followed by administration of an antigen in order to enhance the protective immune effect of the vaccine.

Routes and frequency of administration, as well as dosage, will vary from individual to individual. In general, the pharmaceutical compositions and vaccines may be administered by injection (e.g., intracutaneous, intramuscular, intravenous or subcutaneous), intranasally (e.g., by aspiration) or orally. Between 1 and 3 doses may be administered for a 1–36 week period. Preferably, 3 doses are administered, at intervals of 3–4 months, and booster vaccinations may be given periodically thereafter. Alternate protocols may be appropriate for individual patients. A suitable dose is an amount of polypeptide or DNA that, when administered as described above, is capable of raising an immune response in an immunized patient sufficient to protect the patient from HGE for at least 1–2 years. In general, the amount of polypeptide present in a dose (or produced in situ by the DNA in a dose) ranges from about 1 pg to about 100 mg per kg of host, typically from about 10 pg to about 1 mg, and preferably from about 100 pg to about 1 μg. Suitable dose sizes will vary with the size of the patient, but will typically range from about 0.1 mL to about 5 mL.

While any suitable carrier known to those of ordinary skill in the art may be employed in the pharmaceutical compositions of this invention, the type of carrier will vary depending on the mode of administration. For parenteral administration, such as subcutaneous injection, the carrier preferably comprises water, saline, alcohol, a fat, a wax or a buffer. For oral administration, any of the above carriers or a solid carrier, such as mannitol, lactose, starch, magnesium stearate, sodium saccharine, talcum, cellulose, glucose, sucrose, and magnesium carbonate, may be employed. Biodegradable microspheres (e.g., polylactic galactide) may also be employed as carriers for the pharmaceutical compositions of this invention. Suitable biodegradable microspheres are disclosed, for example, in U.S. Pat. Nos. 4,897,268 and 5,075,109.

Any of a variety of adjuvants may be employed in the vaccines of this invention to nonspecifically enhance the immune response. Most adjuvants contain a substance designed to protect the antigen from rapid catabolism, such as aluminum hydroxide or mineral oil, and a nonspecific stimulator of immune responses, such as lipid A, *Bortadella pertussis* or *Mycobacterium tuberculosis*. Suitable adjuvants are commercially available as, for example, Freund's Incomplete Adjuvant and Freund's Complete Adjuvant (Difco Laboratories, Detroit, Mich.) and Merck Adjuvant 65 (Merck and Company, Inc., Rahway, N,J.). Other suitable adjuvants include alum, biodegradable microspheres, monophosphoryl lipid A and quil A.

The following Examples are offered by way of illustration and not by way of limitation.

EXAMPLE 1

Isolation of DNA Sequences Encoding Ehrilichia Antigens

This example illustrates the preparation of DNA sequences encoding Ehrlichia antigens by screening an Ehrlichia genomic expression library, prepared using genomic DNA from the Ehrlichia species that is the causative agent of HGE, with sera obtained from mice infected with the HGE agent.

Ehrlichia genomic DNA was isolated from infected human HL60 cells and sheared by sonication. The resulting randomly sheared DNA was used to construct an Ehrlichia genomic expression library (approximately 0.5–4.0 kbp inserts) with EcoRI adaptors and a Lambda ZAP II/EcoRI/ CIAP vector (Stratagene, La Jolla, Calif.). The unamplified library ($6.5 \times 10^6$/ml) was screened with an *E. coli* lysate-absorbed Ehrlichia mouse serum pool, as described in Sambrook et al., *Molecular Cloning: A Laboratory Manual*, Cold Spring Harbor Laboratories, Cold Spring Harbor, N.Y., 1989. Positive plaques were visualized and purified with goat-anti-mouse alkaline phosphatase. Phagemid from the plaques was rescued and DNA sequence for positive clones was obtained using forward, reverse, and specific internal primers on a Perkin Elmer/Applied Biosystems Inc. Automated Sequencer Model 373A Roster City, Calif.).

Of the eighteen antigens isolated using this technique, seven (hereinafter referred to as HGE-1, HGE-3, HGE-6, HGE-7, HGE-12, HGE-23 and HGE-24) were found to be related. The determined DNA sequences for HGE-1, HGE-3, HGE-6, HGE-12, HGE-23 and HGE-24 are shown in SEQ ID NO: 1–3 and 5–7, respectively, with the 5' DNA sequence for HGE-7 being provided in SEQ ID NO: 4. The deduced amino acid sequences for HGE-1, HGE-3, HGE-6, HGE-7, HGE-12, HGE-23 and HGE-24 are provided in SEQ ID NO: 8–14, respectively. Comparison of these sequences with known sequences in the gene bank using the DNA STAR system, revealed some degree of homology to the *Anaplasma marginale* major surface protein.

Of the remaining eleven isolated antigens, no significant homologies were found to HGE-2, HGE-9, HGE-14, HGE-15, HGE-16, HGE-17, HGE-18 and HGE-25. The determined full-length DNA sequences for HGE-9 and HGE-14 are provided in SEQ ID NO: 16 and 17, respectively, with the determined 5' DNA sequences for HGE-2, HGE-15, HGE-16, HGE-17, HGE-18 and HGE-25 being shown in SEQ ID NO: 15, and 18–22, respectively. The corresponding predicted amino acid sequences for HGE-2, HGE-9, HGE-14 and HGE-18 are provided in SEQ ID NO: 23–26, respectively. The reverse complements of HGE-14, HGE-15 and HGE-18 were found to contain open reading frames which encode the amino acid sequences shown in SEQ ID NO: 27, 28 and 29, respectively. The predicted amino acid sequence from the reverse complement strand of HGE-14 (SEQ ID NO: 27) was found to contain a 41 amino acid repeat, provided in SEQ ID NO: 30.

The determined DNA sequence for the isolated antigen HGE-11 is provided in SEQ ID NO: 31, with the predicted amino acid sequences being provided in SEQ ID NO: 32 and 33. Comparison of these sequences with known sequence in the gene bank, revealed some homology between the amino acid sequence of SEQ ID NO: 32 and that of bacterial DNA-directed RNA polymerase beta subunit rpoB (Monastyrskaya, G. S. et al., 1990, *Bioorg. Khim.* 6:1106–1109), and further between the amino acid sequence of SEQ ID NO: 33 and that of bacterial DNA-directed RNA polymerase beta' subunit rpoC (Borodin A. M. et al, 1988 *Bioorg. Khim.* 14:1179–1182).

The determined 5' DNA sequence for the antigen HGE-13 is provided in SEQ ID NO: 34. The opposite strand for HGE-13 was found to contain an open reading frame which encodes the amino acid sequence provided in SEQ ID NO: 35. This sequence was found to have some homology to bacterial 2,3-biphosphoglycerate-independent phosphoglycerate mutase (Leyva-Vazquez, M. A. and Setlow, P., 1994 *J. Bacteriol.* 176:3903–3910).

The determined partial nucleotide sequence for the isolated antigen HGE-8 (SEQ ID NO: 36) was found to include, on the reverse complement of the 5' end, two open reading frames encoding the amino acid sequences provided in SEQ ID NO: 37 and 38. The amino acid sequences of SEQ ID NO: 37 and 38 were found to show some homology to prokaryotic and eukaryotic dihydrolipamide succinyltransferase (Fleischmann R. D. et al, 1995 *Science* 269:496–512) and methionine aminopeptidase (Chang, Y. H., 1992 *J. Biol. Chem.* 267:8007–8011), respectively.

Subsequent studies resulted in the determination of extended DNA sequences for HGE-2, HGE-7, HGE-8, HGE-11, HGE-14, HGE-15, HGE-16, HGE-18, HGE-23 and HGE-25 (SEQ ID NO: 39–48, respectively) and in the determination of the 3' sequence for HGE-17 (SEQ ID NO: 49). The complement of the extended HGE-2 DNA sequence was found to contain an open reading frame which encodes for a 61.4 kDa protein (SEQ ID NO: 50) having three copies of a 125 amino acid repeat (SEQ ID NO: 51). The extended DNA sequence of HGE-7 was found to contain two open reading frames encoding for the amino acid sequences shown in SEQ ID NO: 52 and 53. The extended DNA sequence of HGE-8 was found to contain four open reading frames encoding the proteins of SEQ ID NO: 54–57. Each of these four proteins was found to show some similarity to known proteins, however, to the best of the inventors' knowledge, none have previously been identified in Ehrlichia.

The extended DNA sequence of HGE-11 was found to contain two open reading frames encoding for the amino acid sequences provided in SEQ ID NO: 58 and 59. These two proteins were found to show some homology to the bacterial DNA-directed RNA polymerase beta subunits ipoB and rpo C, respectively. The reverse complement of the extended DNA sequence of HGE-14 was found to contain two open reading frames, with one encoding the amino acid sequence provided in SEQ ID NO: 60. The second open reading frame encodes the amino acid sequence provided in SEQ ID NO: 61, which contains the amino acid sequence provided in SEQ ID NO: 27. The extended DNA sequence of HGE-15 was found to contain two open reading frames encoding for the sequences provided in SEQ ID NO: 62 and 63, with a third open reading frame encoding the sequence of SEQ ID NO: 64 being located on the reverse complement. The extended DNA sequence of HGE-16 was found to contain an open reading frame encoding the amino acid sequence of SEQ ID NO: 65. The reverse complement of the 3' DNA sequence of HGE-17 was found to contain two open reading frames encoding the amino acid sequences of SEQ ID NO: 66 and 67.

The reverse complement of the extended DNA sequence of HGE-18 was found to contain three open reading frames encoding the amino acid sequences of SEQ ID NO: 68–70. The sequence of SEQ ID NO: 70 was found to show some homology to bacterial DNA helicase. The extended DNA sequence of HGE-23 was found to contain two open reading frames encoding for the sequences of SEQ ID NO:71 and 72. Both of these sequences, together with those of SEQ ID NO:52 and 53, were found to share some homology with the Anaplasma marginale major surface protein. The predicted amino acid sequence for the extended DNA sequence of HGE-25 is provided in SEQ ID NO:73. This sequence was found to show some similarity to that of SEQ ID NO:64 (HGE-15). No significant homologies were found to the sequences of HGE-2, HGE-14, HGE-15, HGE-16, HGE-17 and HGE-25 (SEQ ID NO: 50, 60–67 and 73).

EXAMPLE 2

Use of Representative Antigens for Serodiagnosis of HGE Infection

The diagnostic properties of representative Ehrlichia antigens were determined by Western blot analysis as follows.

Antigens were induced as pBluescript SK- constructs (Stratagene), with 2 mM IPTG for three hours (T3), after which the resulting proteins from time 0 (T0) and T3 were separated by SDS-PAGE on 15% gels. Separated proteins were then transferred to nitrocellulose and blocked for 1 hr in 1% BSA in 0.1% Tween 20™/PBS. Blots were then washed 3 times in 0.1% Tween 20™/PBS and incubated with either an HGE patient serum pool (1:200) or an Ehrlichia-infected mouse serum pool for a period of 2 hours. After washing in 0.1% Tween 20™/PBS 3 times, blots were incubated with a second antibody (goat-anti-human IgG conjugated to alkaline phosphatase (AP) or goat-anti-mouse IgG-AP, respectively) for 1 hour. Immunocomplexes were visualized with NBT/BCIP (Gibco BRL) after washing with Tween 20™/PBS three times and AP buffer (100 mM Tris-HCl, 100 mM Na Cl, 5 mM $MgCl_2$, pH 9.5) two times.

As shown in FIG. 1, resulting bands of reactivity with serum antibody were seen at 37 kDa for HGE-1 and HGE-3 for both the mouse serum pool and the human serum pool. Protein size standards, in kDa (Gibco BRL, Gaithersburg, Md.), are shown to the left of the blots.

Western blots were performed on partially purified HGE-1 and HGE-3 recombinant antigen with a series of patient sera from HGE patients, patients with Lyme disease, babesiosis patients or from normal donors. Specifically, purified antigen (4 μg) was separated by SDS-PAGE on 12% gels. Protein was then transferred to nitrocellulose membrane for immunoblot analysis. The membrane was first blocked with PBS containing 1% Tween 20™ for 2 hours. Membranes were then cut into strips and incubated with individual sera (1/500) for two hours. The strips were washed 3 times in PBS/0.1% Tween 20™ containing 0.5 M NaCl prior to incubating with Protein A-horseradish peroxidase conjugate (1/20,000) in PBS/0.1% Tween 20™/0.5 M NaCl for 45 minutes. After further washing three times in PBS/0.1% Tween 20™/0.5 M NaCl, ECL chemiluminescent substrate (Amersham, Arlington Heights, Ill.) was added for 1 min. Strips were then reassembled and exposed to Hyperfilm ECL (Amersham) for 5–30 seconds.

Figure 2A:
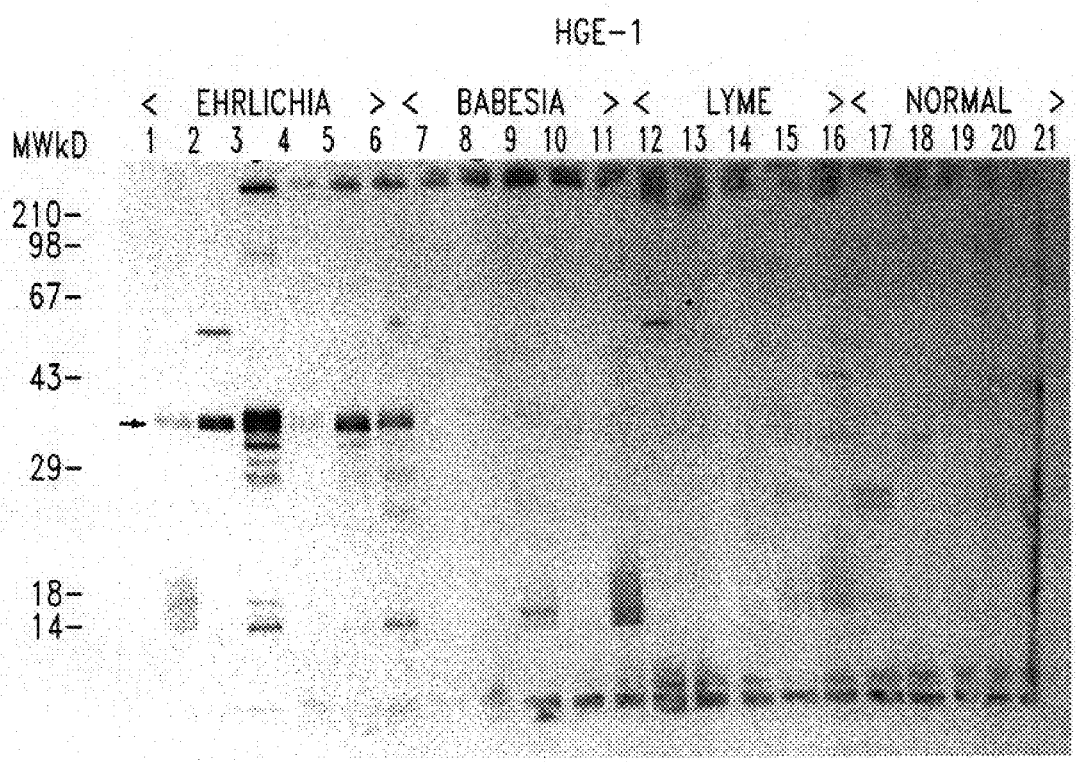
FIGS. 2A and B show the reactivity of purified recombinant Ehrlichia antigens HGE-1 and HGE-3, respectively, with sera from HGE-infected patients, babesiosis-infected patients, Lyme-disease infected patients and normal donors as determined by Western blot analysis.
Figure 2B:
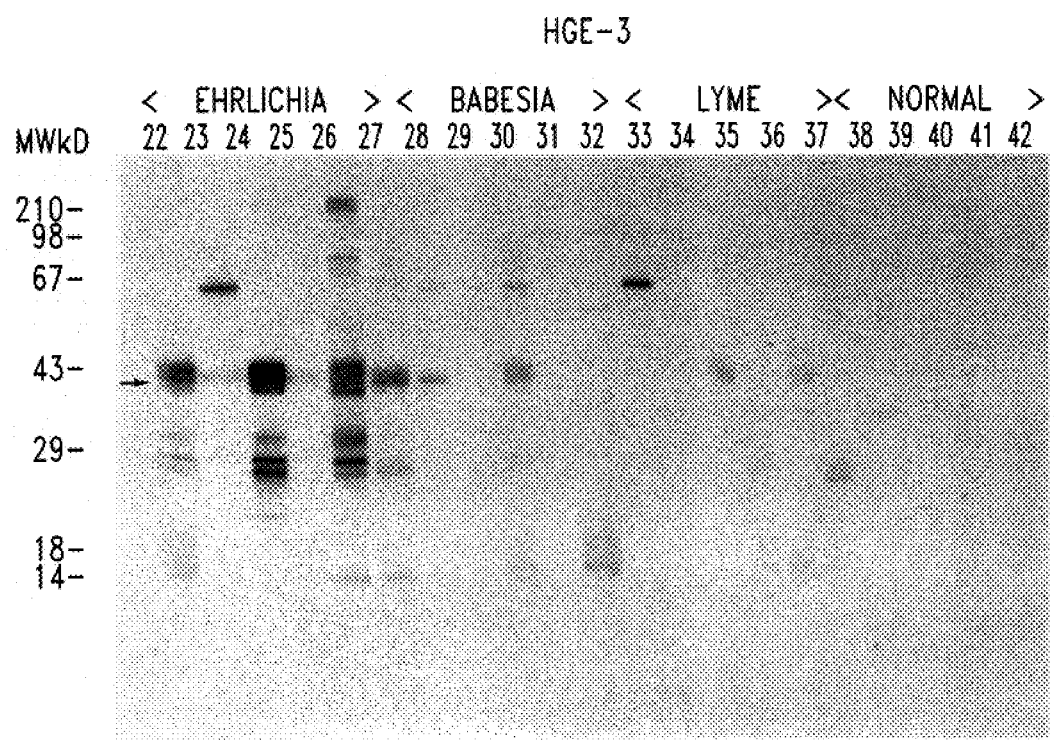

Lanes 1–6 of FIG. 2A show the reactivity of purified recombinant HGE-1 (MW 37 kD) with sera from six HGE-infected patients, of which all were clearly positive. In contrast, no immunoreactivity with HGE-1 was seen with sera from patients with either babesiosis (lanes 7–11), or Lyme disease (lanes 12–16), or with sera from normal individuals (lanes 17–21). As shown in FIG. 2B, HGE-3 (MW 37 kD) was found to react with sera from all six HGE patients (lanes 22–27), while cross-reactivity was seen with sera from two of the five babesiosis patients and weak cross-reactivity was seen with sera from two of the five Lyme disease patients. This apparent cross-reactivity may represent the ability of the antigen HGE-3 to detect low antibody titer in patients co-infected with HGE. No immunoreactivity of HGE-3 was seen with sera from normal patients.

EXAMPLE 3

Synthesis of Synthetic Polypeptides

Polypeptides may be synthesized on a Millipore 9050 peptide synthesizer using FMOC chemistry with HPTU (O-Benzotriazole-N,N,N',N'-tetramethyluronium hexafluorophosphate) activation. A Gly-Cys-Gly sequence may be attached to the amino terminus of the peptide to provide a method of conjugating or labeling of the peptide. Cleavage of the peptides from the solid support may be carried out using the following cleavage mixture: trifluoroacetic acid:ethanedithiol:thioanisole:water:phenol (40:1:2:2:3). After cleaving for 2 hours, the peptides may be precipitated in cold methyl-t-butyl-ether. The peptide pellets may then be dissolved in water containing 0.1% trifluoroacetic acid (TFA) and lyophilized prior to purification by C18 reverse phase HPLC. A gradient of 0–60% acetonitrile (containing 0.1% TFA) in water (containing 0.1% TFA) may be used to elute the peptides. Following lyophilization of the pure fractions, the peptides may be characterized using electrospray mass spectrometry and by amino acid analysis.

Although the present invention has been described in some detail by way of illustration and example for purposes of clarity of understanding, changes and modifications can be carried out without departing from the scope of the invention which is intended to be limited only by the scope of the appended claims.

What is claimed is:

1. An isolated polypeptide comprising an Ehrlichia antigen, wherein said antigen comprises an amino acid sequence encoded by a DNA sequence selected from the group consisting of SEQ ID NO: 1, the complements of said sequence, and DNA sequences that hybridize to SEQ ID NO:1 or a complement thereof under moderately stringent conditions.

2. A pharmaceutical composition comprising at least one polypeptide according to claim 1 and a physiologically acceptable carrier.

3. An isolated polypeptide comprising an amino acid sequence of SEQ ID NO: 8.

* * * * *

SEQUENCE LISTING (1) GENERAL INFORMATION:

(iii) NUMBER OF SEQUENCES: 73

(2) INFORMATION FOR SEQ ID NO:1:

(i) SEQUENCE CHARACTERISTICS:
        (A) LENGTH: 1345 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: Ehrlichia (xi) SEQUENCE DESCRIPTION: SEQ ID NO:1:

```
TTGAGCTTGA GATTGGTTAC GAGCGCTTCA AGACCAAGGG TATTAGAGAT AGTGGTAGTA      60

AGGAAGATGA AGCTGATACA GTATATCTAC TAGCTAAGGA GTTAGCTTAT GATGTTGTTA     120

CTGGTCAGAC TGATAACCTT GCCGCTGCTC TTGCCAAAAC CTCCGGTAAG GATATTGTTC     180

AGTTTGCTAA GGCGGTGGAG ATTTCTCATT CCGAGATTGA TGGCAAGGTT TGTAAGACGA     240

AGTCGGCGGG AACTGGAAAA AATCCGTGTG ATCATAGCCA AAAGCCGTGT AGTACGAATG     300

CGTATTATGC GAGGAGAACG CAGAAGAGTA GGAGTTCGGG AAAAACGTCT TTATGCGGGG     360

ACAGTGGGTA TAGCGGGCAG GAGCTAATAA CGGGTGGGCA TTATAGCAGT CCAAGCGTAT     420

TCCGGAATTT TGTCAAAGAC ACACTACAAG GAAATGGTAG TGAGAACTGG CCTACATCTA     480

CTGGAGAAGG AAGTGAGAGT AACGACAACG CCATAGCCGT TGCTAAGGAC CTAGTAAATG     540

AACTTACTCC TGAAGAACGA ACCATAGTGG CTGGGTTACT TGCTAAAATT ATTGAAGGAA     600

GCGAGGTTAT TGAGATTAGG GCCATCTCTT CGACTTCAGT TACAATGAAT ATTTGCTCAG     660

ATATCACGAT AAGTAATATC TTAATGCCGT ATGTTTGTGT TGGTCCAGGG ATGAGCTTTG     720

TTAGTGTTGT TGATGGTCAC ACTGCTGCAA AGTTTGCATA TCGGTTAAAG GCAGGTCTGA     780

GTTATAAATT TTCGAAAGAA GTTACAGCTT TTGCAGGTGG TTTTTACCAT CACGTTATAG     840

GAGATGGTGT TTATGATGAT CTGCCATTGC GGCATTTATC TGATGATATT AGTCCTGTGA     900

AACATGCTAA GGAAACCGCC ATTGCTAGAT TCGTCATGAG GTACTTTGGC GGGGAATTTG     960

GTGTTAGGCT CGCTTTTTAA GGTTGCGACC TAAAAGCACT TAGCTCGCCT TCACTCCCCC    1020
```

```
TTAAGCAATA TGATGCACAT TTGTTGCCCT ACAAATCTAA TATAAGGTTT GTTGCCTATA    1080

CTCGTGCCGA ATTCGGCACG AGGAGGAAGC TGAACTCACC CATCAGTCTC TCTCATCCGT    1140

TGGCCACCTG CTGTCCCCAC CCACCCACCA AACTGGTGCT TTTAATGGAA TCAGCTTTAA    1200

AAAGAAAAAA ATCCTCCAAG TAACAAAGCA CCCTATAATT ATTCCGCAGC TCCTTGTCCT    1260

CGGTAATTTT AGGCTTGTGC TGCTATCATT ACACATTACA TGGAGTTAGG GAGTCATAGC    1320

TCTTGTGTGG CCAATCAGTG ATACA                                         1345
```

(2) INFORMATION FOR SEQ ID NO:2:

(i) SEQUENCE CHARACTERISTICS:
        (A) LENGTH: 1132 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: Ehrlichia (xi) SEQUENCE DESCRIPTION: SEQ ID NO:2:

```
ATTTCTATAT TGGTTTGGAT TACAGTCCAG CGTTTAGCAA GATAAGAGAT TTTAGTATAA      60

GGGAGAGTAA CGGAGAGACA AAGGCAGTAT ATCCATACTT AAAGGATGGA AAGAGTGTAA     120

AGCTAGAGTC ACACAAGTTT GACTGGAACA CACCTGATCC TCGGATTGGG TTTAAGGACA     180

ACATGCTTGT AGCTATGGAA GGTAGTGTTG GTTATGGTAT TGGTGGTGCC AGGGTTGAGC     240

TTGAGATTGG TTACGAGCGC TTCAAGACCA AGGGTATTAG AGATAGTGGT AGTAAGGAAG     300

ATGAAGCTGA TACAGTATAT CTACTAGCTA AGGAGTTAGC TTATGATGTT GTTACTGGAC     360

AGACTGATAA CCTTGCTGCT GCTCTTGCTA AGACCTCGGG GAAAGACATC GTTCAGTTTG     420

CTAAGGCGGT TGGGGTTTCT CATCCTAGTA TTGATGGGAA GGTTTGTAAG ACGAAGGCGG     480

ATAGCTCGAA GAAATTTCCG TTATATAGTG ACGAAACGCA CACGAAGGGG GCAAATGAGG     540

GGAGAACGTC TTTGTGCGGT GACAATGGTA GTTCTACGAT AACAACCAGT GGTACGAATG     600

TAAGTGAAAC TGGGCAGGTT TTTAGGGATT TTATCAGGGC AACGCTGAAA GAGGATGGTA     660

GTAAAAACTG GCCAATTTCA AGCGGCACGG GAACTCCAAA ACCTGTCACG AACGACAACG     720

CCAAAGCCGT AGGTAAAGAC CTAGTACAGG AGCTAACCCC TGAAGAAAAA ACCATAGTAG     780

CAGGGTTACT AGCTAAGACT ATTGAAGGGG GTGAAGTTGT TGAGATCAGG GCGGTTTCTT     840

CTACTTCCGT AATGGTCAAT GCTTGTTATG ATCTTCTTAG TGAAGGTTTA GGTGTTGTTC     900

CTTATGCTTG TGTTGGTCTC GGTGGTAACT TCGTGGGCGT GGTTGATGGA ATTCATTACA     960

CAAACCATCT TTAACTCTGA ATACCCTAGT TAAGGTAAGT GAAGTAACTA GGCAAATTAG    1020

TGCTGCACCA CTCGTGAAAC AAACTACGAT CAGCGATTCA CCATACTTAG TAGGTCCGTA    1080

CAGTGGCTTT ACGCTCTTAC CCATCATGAA AAATACTTGC TATCTAGGAA TC           1132
```

(2) INFORMATION FOR SEQ ID NO:3:

(i) SEQUENCE CHARACTERISTICS:
        (A) LENGTH: 554 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:

(A) ORGANISM: Ehrlichia (xi) SEQUENCE DESCRIPTION: SEQ ID NO:3:

```
CTACTAGCTA AGGAGTTAGC TTATGATGTT GTTACTGGGC AGACTGATAA CCTTGCTGCT      60
GCTCTTGCCA AGACTTCTGG TAAAGATATT GTTCAGTTTG CTAAGACTCT TAATATTTCT     120
CACTCTAATA TCGATGGGAA GGTTTGTAGG AGGGAAAAGC ATGGGAGTCA AGGTTTGACT     180
GGAACCAAAG CAGGTTCGTG TGATAGTCAG CCACAAACGG CGGGTTTCGA TTCCATGAAA     240
CAAGGTTTGA TGGCAGCTTT AGGCGAACAA GGCGCTGAAA AGTGGCCCAA AATTAACAAT     300
GGTGGCCACG CAACAATTTA TAGTAGTAGC GCAGGTCCAG GAAATGCGTA TGCTAGAGAT     360
GCATCTACTA CGGTAGCTAC AGACCTAACA AAGCTCACTA CTGAAGAAAA AACCATAGTA     420
GCAGGGTTAC TAGCTAGAAC TATTGAAGGG GGTGAAGTTG TTGAGATTAG GGCAGTTTCT     480
TCTACTTCTG TGATGGTTAA TGCTTGTTAT GATCTTCTTA GTGAAGGTTT AGGTGTTGTA     540
CCTTATGCTT GTGT                                                      554
```

(2) INFORMATION FOR SEQ ID NO:4:

(i) SEQUENCE CHARACTERISTICS:
        (A) LENGTH: 559 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: Ehrlichia (xi) SEQUENCE DESCRIPTION: SEQ ID NO:4:

```
ATGCTGTGAA AATTACTAAC TCCACTATCG ATGGGAAGGT TTGTAATGGT AGTAGAGAGA      60
AGGGAATAG TGCTGGGAAC AACAACAGTG CTGTGGCTAC CTACGCGCAG ACTCACACAG     120
CGAATACATC AACGTCACAG TGTAGCGGTC TAGGGACCAC TGTTGTCAAA CAAGGTTATG     180
GAAGTTTGAA TAAGTTTGTT AGCCTGACGG GGGTTGGTGA AGGTAAAAAT TGGCCTACAG     240
GTAAGATACA CGACGGTAGT AGTGGTGTCA AAGATGGTGA ACAGAACGGG AATGCCAAAG     300
CCGTAGCTAA AGACCTAGTA GATCTTAATC GTGACGAAAA AACCATAGTA GCAGGATTAC     360
TAGCTAAAAC TATTGAAGGG GGTGAAGTTG TTGAGATCAG GGCGGTTTCT TCTACTTCTG     420
TGATGGTTAA TGCTTGTTAT GATCTTCTTA GTGAAGGTTT AGGCGTTGTT CCTTACGCTT     480
GTGTCGGTCT CGGAGGTAAC TTCGTGGGCG TTGTTGATGG GCATATCACT CCTAAGCTTG     540
CTTATAGATT AAAGGCTGG                                                 559
```

(2) INFORMATION FOR SEQ ID NO:5:

(i) SEQUENCE CHARACTERISTICS:
        (A) LENGTH: 201 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: Ehrlichia (xi) SEQUENCE DESCRIPTION: SEQ ID NO:5:

```
AGCGCTTCAA GACCAAGGGT ATTAGAGATA GTGGTAGTAA GGAAGATGAA GCTGATACAG      60
TATATCTACT AGCTAAGGAG TTAGCTTATG ATGTTGTTAC TGGACAGACT GATAACCTTG     120
```

```
CCGCTGCTCT TGCTAAAACC TCGGGGAAAG ACTTTGTTCA GTTTGCTAAG GCCGTGGAGA      180

TTTCTAATTC TACGATTGGG G                                                201

(2) INFORMATION FOR SEQ ID NO:6:

(i) SEQUENCE CHARACTERISTICS:
        (A) LENGTH: 467 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: Ehrlichia (xi) SEQUENCE DESCRIPTION: SEQ ID NO:6:

GGTATATCGA TAGCCTACGT AGTCACTCCT TATTATTAAA AAGGAAGACC AAGGGTATTA       60

GAGATAGTGG AAGTAAGGAA GATGAAGCAG ATACAGTATA TCTACTAGCT AAGGAGTTAG      120

CTTATGATGT TGTTACTGGG CAGACTGATA ACCTTGCCGC TGCTCTTGCC AAAACCTCCG      180

GTAAGGACTT TGTTAAATTT GCCAATGCTG TTGTTGGAAT TTCTCACCCC GATGTTAATA      240

AGAAGGTTTG TGCGACGAGG AAGGACAGTG GTGGTACTAG ATATGCGAAG TATGCTGCCA      300

CGACTAATAA GAGCAGCAAC CCTGAAACCT CACTGTGTGG AGACGAAGGT GGCTCGAGCG      360

GCACGAATAA TACACAAGAG TTTCTTAAGG AATTTGTAGC CCAAACCCTA GTAGAAAATG      420

AAAGTAAAAA CTGGCCTACT TCAAGCGGGA CTGGGTTGAA GACTAAC                   467

(2) INFORMATION FOR SEQ ID NO:7:

(i) SEQUENCE CHARACTERISTICS:
        (A) LENGTH: 530 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: Ehrlichia (xi) SEQUENCE DESCRIPTION: SEQ ID NO:7:

AAGATGAAGC TGATACAGTA TATCTACTGG CTAAGGAGTT AGCTTATGAT GTTGTTACTG       60

GACAGACTGA TAAGCTTACT GCTGCTCTTG CTAAGACCTC CGGGAAGGAC TTTGTTCAGT      120

TTGCTAAGGC GGTTGGGGTT TCTCATCCTA ATATCGATGG GAAGGTTTGT AAGACTACGC      180

TAGGGCACAC GAGTGCGGAT AGCTACGGTG TGTATGGGGA GTTAACAGGC CAGGCGAGTG      240

CGAGTGAGAC ATCGTTATGT GGTGGTAAGG GTAAAAATAG TAGTGGTGGT GGAGCTGCTC      300

CCGAAGTTTT AAGGGACTTT GTAAAGAAAT CTCTGAAAGA TGGGGGCCAA AACTGGCCAA      360

CATCTAGGGC GACCGAGAGT TCACCTAAGA CTAAATCTGA AACTAACGAC AATGCAAAAG      420

CTGTCGCTAA AGACCTAGTA GACCTTAATC CTGAAGAAAA AACCATAGTA GCAGGGTTAC      480

TAGCTAAAAC TATTGAAGGT GGGGAAGTTG TAGAAATCAG AGCAGTTTCT                 530

(2) INFORMATION FOR SEQ ID NO:8:

(i) SEQUENCE CHARACTERISTICS:
        (A) LENGTH: 325 amino acids
        (B) TYPE: amino acid
        (C) STRANDEDNESS: single
        (D) TOPOLOGY: linear
```

(ii) MOLECULE TYPE: protein (vi) ORIGINAL SOURCE:
    (A) ORGANISM: Ehrlichia (xi) SEQUENCE DESCRIPTION: SEQ ID NO:8:

```
Glu Leu Glu Ile Gly Tyr Glu Arg Phe Lys Thr Lys Gly Ile Arg Asp
1               5                   10                  15

Ser Gly Ser Lys Glu Asp Glu Ala Asp Thr Val Tyr Leu Leu Ala Lys
            20                  25                  30

Glu Leu Ala Tyr Asp Val Val Thr Gly Gln Thr Asp Asn Leu Ala Ala
        35                  40                  45

Ala Leu Ala Lys Thr Ser Gly Lys Asp Ile Val Gln Phe Ala Lys Ala
    50                  55                  60

Val Glu Ile Ser His Ser Glu Ile Asp Gly Lys Val Cys Lys Thr Lys
65                  70                  75                  80

Ser Ala Gly Thr Gly Lys Asn Pro Cys Asp His Ser Gln Lys Pro Cys
                85                  90                  95

Ser Thr Asn Ala Tyr Tyr Ala Arg Arg Thr Gln Lys Ser Arg Ser Ser
            100                 105                 110

Gly Lys Thr Ser Leu Cys Gly Asp Ser Gly Tyr Ser Gly Gln Glu Leu
        115                 120                 125

Ile Thr Gly Gly His Tyr Ser Ser Pro Ser Val Phe Arg Asn Phe Val
    130                 135                 140

Lys Asp Thr Leu Gln Gly Asn Gly Ser Glu Asn Trp Pro Thr Ser Thr
145                 150                 155                 160

Gly Glu Gly Ser Glu Ser Asn Asp Asn Ala Ile Ala Val Ala Lys Asp
                165                 170                 175

Leu Val Asn Glu Leu Thr Pro Glu Glu Arg Thr Ile Val Ala Gly Leu
            180                 185                 190

Leu Ala Lys Ile Ile Glu Gly Ser Glu Val Ile Glu Ile Arg Ala Ile
        195                 200                 205

Ser Ser Thr Ser Val Thr Met Asn Ile Cys Ser Asp Ile Thr Ile Ser
    210                 215                 220

Asn Ile Leu Met Pro Tyr Val Cys Val Gly Pro Gly Met Ser Phe Val
225                 230                 235                 240

Ser Val Val Asp Gly His Thr Ala Ala Lys Phe Ala Tyr Arg Leu Lys
                245                 250                 255

Ala Gly Leu Ser Tyr Lys Phe Ser Lys Glu Val Thr Ala Phe Ala Gly
            260                 265                 270

Gly Phe Tyr His His Val Ile Gly Asp Gly Val Tyr Asp Asp Leu Pro
        275                 280                 285

Leu Arg His Leu Ser Asp Asp Ile Ser Pro Val Lys His Ala Lys Glu
    290                 295                 300

Thr Ala Ile Ala Arg Phe Val Met Arg Tyr Phe Gly Gly Glu Phe Gly
305                 310                 315                 320

Val Arg Leu Ala Phe
                325
```

(2) INFORMATION FOR SEQ ID NO:9:

(i) SEQUENCE CHARACTERISTICS:
        (A) LENGTH: 323 amino acids
        (B) TYPE: amino acid
        (C) STRANDEDNESS: single
        (D) TOPOLOGY: linear (ii) MOLECULE TYPE: protein (vi) ORIGINAL SOURCE:
    (A) ORGANISM: Ehrlichia (xi) SEQUENCE DESCRIPTION: SEQ ID NO:9:

```
Phe Tyr Ile Gly Leu Asp Tyr Ser Pro Ala Phe Ser Lys Ile Arg Asp
1               5                   10                  15

Phe Ser Ile Arg Glu Ser Asn Gly Glu Thr Lys Ala Val Tyr Pro Tyr
            20                  25                  30

Leu Lys Asp Gly Lys Ser Val Lys Leu Glu Ser His Lys Phe Asp Trp
            35                  40                  45

Asn Thr Pro Asp Pro Arg Ile Gly Phe Lys Asp Asn Met Leu Val Ala
        50                  55                  60

Met Glu Gly Ser Val Gly Tyr Gly Ile Gly Gly Ala Arg Val Glu Leu
65                  70                  75                  80

Glu Ile Gly Tyr Glu Arg Phe Lys Thr Lys Gly Ile Arg Asp Ser Gly
                85                  90                  95

Ser Lys Glu Asp Glu Ala Asp Thr Val Tyr Leu Leu Ala Lys Glu Leu
                100                 105                 110

Ala Tyr Asp Val Val Thr Gly Gln Thr Asp Asn Leu Ala Ala Ala Leu
            115                 120                 125

Ala Lys Thr Ser Gly Lys Asp Ile Val Gln Phe Ala Lys Ala Val Gly
130                 135                 140

Val Ser His Pro Ser Ile Asp Gly Lys Val Cys Lys Thr Lys Ala Asp
145                 150                 155                 160

Ser Ser Lys Lys Phe Pro Leu Tyr Ser Asp Glu Thr His Thr Lys Gly
                165                 170                 175

Ala Asn Glu Gly Arg Thr Ser Leu Cys Gly Asp Asn Gly Ser Ser Thr
            180                 185                 190

Ile Thr Thr Ser Gly Thr Asn Val Ser Glu Thr Gly Gln Val Phe Arg
        195                 200                 205

Asp Phe Ile Arg Ala Thr Leu Lys Glu Asp Gly Ser Lys Asn Trp Pro
210                 215                 220

Ile Ser Ser Gly Thr Gly Thr Pro Lys Pro Val Thr Asn Asp Asn Ala
225                 230                 235                 240

Lys Ala Val Gly Lys Asp Leu Val Gln Glu Leu Thr Pro Glu Glu Lys
                245                 250                 255

Thr Ile Val Ala Gly Leu Leu Ala Lys Thr Ile Glu Gly Gly Glu Val
            260                 265                 270

Val Glu Ile Arg Ala Val Ser Ser Thr Ser Val Met Val Asn Ala Cys
        275                 280                 285

Tyr Asp Leu Leu Ser Glu Gly Leu Gly Val Val Pro Tyr Ala Cys Val
    290                 295                 300

Gly Leu Gly Gly Asn Phe Val Gly Val Val Asp Gly Ile His Tyr Thr
305                 310                 315                 320

Asn His Leu
```

(2) INFORMATION FOR SEQ ID NO:10:

(i) SEQUENCE CHARACTERISTICS:
        (A) LENGTH: 185 amino acids
        (B) TYPE: amino acid
        (C) STRANDEDNESS: single
        (D) TOPOLOGY: linear (ii) MOLECULE TYPE: protein (vi) ORIGINAL SOURCE:
    (A) ORGANISM: Ehrlichia (xi) SEQUENCE DESCRIPTION: SEQ ID NO:10:

```
Leu Leu Ala Lys Glu Leu Ala Tyr Asp Val Val Thr Gly Gln Thr Asp
1               5                   10                  15

Asn Leu Ala Ala Ala Leu Ala Lys Thr Ser Gly Lys Asp Ile Val Gln
            20                  25                  30

Phe Ala Lys Thr Leu Asn Ile Ser His Ser Asn Ile Asp Gly Lys Val
        35                  40                  45

Cys Arg Arg Glu Lys His Gly Ser Gln Gly Leu Thr Gly Thr Lys Ala
50                  55                  60

Gly Ser Cys Asp Ser Gln Pro Gln Thr Ala Gly Phe Asp Ser Met Lys
65                  70                  75                  80

Gln Gly Leu Met Ala Ala Leu Gly Glu Gln Gly Ala Glu Lys Trp Pro
                85                  90                  95

Lys Ile Asn Asn Gly Gly His Ala Thr Ile Tyr Ser Ser Ser Ala Gly
            100                 105                 110

Pro Gly Asn Ala Tyr Ala Arg Asp Ala Ser Thr Thr Val Ala Thr Asp
        115                 120                 125

Leu Thr Lys Leu Thr Thr Glu Glu Lys Thr Ile Val Ala Gly Leu Leu
130                 135                 140

Ala Arg Thr Ile Glu Gly Gly Glu Val Val Glu Ile Arg Ala Val Ser
145                 150                 155                 160

Ser Thr Ser Val Met Val Asn Ala Cys Tyr Asp Leu Leu Ser Glu Gly
                165                 170                 175

Leu Gly Val Val Pro Tyr Ala Cys Val
            180                 185
```

(2) INFORMATION FOR SEQ ID NO:11:

(i) SEQUENCE CHARACTERISTICS:
        (A) LENGTH: 185 amino acids
        (B) TYPE: amino acid
        (C) STRANDEDNESS: single
        (D) TOPOLOGY: linear (ii) MOLECULE TYPE: protein (vi) ORIGINAL SOURCE:
        (A) ORGANISM: Ehrlichia (xi) SEQUENCE DESCRIPTION: SEQ ID NO:11:

```
Ala Val Lys Ile Thr Asn Ser Thr Ile Asp Gly Lys Val Cys Asn Gly
1               5                   10                  15

Ser Arg Glu Lys Gly Asn Ser Ala Gly Asn Asn Ser Ala Val Ala
            20                  25                  30

Thr Tyr Ala Gln Thr His Thr Ala Asn Thr Ser Thr Ser Gln Cys Ser
        35                  40                  45

Gly Leu Gly Thr Thr Val Val Lys Gln Gly Tyr Gly Ser Leu Asn Lys
50                  55                  60

Phe Val Ser Leu Thr Gly Val Gly Glu Gly Lys Asn Trp Pro Thr Gly
65                  70                  75                  80

Lys Ile His Asp Gly Ser Ser Gly Val Lys Asp Gly Glu Gln Asn Gly
                85                  90                  95

Asn Ala Lys Ala Val Ala Lys Asp Leu Val Asp Leu Asn Arg Asp Glu
            100                 105                 110
```

```
Lys Thr Ile Val Ala Gly Leu Leu Ala Lys Thr Ile Glu Gly Gly Glu
        115                 120                 125

Val Val Glu Ile Arg Ala Val Ser Ser Thr Ser Val Met Val Asn Ala
        130                 135                 140

Cys Tyr Asp Leu Leu Ser Glu Gly Leu Gly Val Val Pro Tyr Ala Cys
145                 150                 155                 160

Val Gly Leu Gly Gly Asn Phe Val Gly Val Asp Gly His Ile Thr
                    165                 170                 175

Pro Lys Leu Ala Tyr Arg Leu Lys Ala
            180                 185

(2) INFORMATION FOR SEQ ID NO:12:

(i) SEQUENCE CHARACTERISTICS:
        (A) LENGTH: 66 amino acids
        (B) TYPE: amino acid
        (C) STRANDEDNESS: single
        (D) TOPOLOGY: linear (ii) MOLECULE TYPE: protein (vi) ORIGINAL SOURCE:
        (A) ORGANISM: Ehrlichia (xi) SEQUENCE DESCRIPTION: SEQ ID NO:12:

Arg Phe Lys Thr Lys Gly Ile Arg Asp Ser Gly Ser Lys Glu Asp Glu
1               5                   10                  15

Ala Asp Thr Val Tyr Leu Leu Ala Lys Glu Leu Ala Tyr Asp Val Val
                20                  25                  30

Thr Gly Gln Thr Asp Asn Leu Ala Ala Ala Leu Ala Lys Thr Ser Gly
            35                  40                  45

Lys Asp Phe Val Gln Phe Ala Lys Ala Val Glu Ile Ser Asn Ser Thr
    50                  55                  60

Ile Gly
65

(2) INFORMATION FOR SEQ ID NO:13:

(i) SEQUENCE CHARACTERISTICS:
        (A) LENGTH: 155 amino acids
        (B) TYPE: amino acid
        (C) STRANDEDNESS: single
        (D) TOPOLOGY: linear (ii) MOLECULE TYPE: protein (vi) ORIGINAL SOURCE:
        (A) ORGANISM: Ehrlichia (xi) SEQUENCE DESCRIPTION: SEQ ID NO:13:

Tyr Ile Asp Ser Leu Arg Ser His Ser Leu Leu Leu Lys Arg Lys Thr
1               5                   10                  15

Lys Gly Ile Arg Asp Ser Gly Ser Lys Glu Asp Glu Ala Asp Thr Val
                20                  25                  30

Tyr Leu Leu Ala Lys Glu Leu Ala Tyr Asp Val Val Thr Gly Gln Thr
            35                  40                  45

Asp Asn Leu Ala Ala Ala Leu Ala Lys Thr Ser Gly Lys Asp Phe Val
    50                  55                  60

Lys Phe Ala Asn Ala Val Val Gly Ile Ser His Pro Asp Val Asn Lys
65                  70                  75                  80

Lys Val Cys Ala Thr Arg Lys Asp Ser Gly Gly Thr Arg Tyr Ala Lys
```

-continued

```
                85                  90                  95
Tyr Ala Ala Thr Thr Asn Lys Ser Ser Asn Pro Glu Thr Ser Leu Cys
                    100                 105                 110
Gly Asp Glu Gly Gly Ser Ser Gly Thr Asn Asn Thr Gln Glu Phe Leu
                    115                 120                 125
Lys Glu Phe Val Ala Gln Thr Leu Val Glu Asn Glu Ser Lys Asn Trp
                130                 135                 140
Pro Thr Ser Ser Gly Thr Gly Leu Lys Thr Asn
145                 150                 155
```

(2) INFORMATION FOR SEQ ID NO:14:

(i) SEQUENCE CHARACTERISTICS:
        (A) LENGTH: 176 amino acids
        (B) TYPE: amino acid
        (C) STRANDEDNESS: single
        (D) TOPOLOGY: linear (ii) MOLECULE TYPE: protein (vi) ORIGINAL SOURCE:
        (A) ORGANISM: Ehrlichia (xi) SEQUENCE DESCRIPTION: SEQ ID NO:14:

```
Asp Glu Ala Asp Thr Val Tyr Leu Leu Ala Lys Glu Leu Ala Tyr Asp
1               5                   10                  15
Val Val Thr Gly Gln Thr Asp Lys Leu Thr Ala Ala Leu Ala Lys Thr
                20                  25                  30
Ser Gly Lys Asp Phe Val Gln Phe Ala Lys Ala Val Gly Val Ser His
                35                  40                  45
Pro Asn Ile Asp Gly Lys Val Cys Lys Thr Thr Leu Gly His Thr Ser
            50                  55                  60
Ala Asp Ser Tyr Gly Val Tyr Gly Glu Leu Thr Gly Gln Ala Ser Ala
65                  70                  75                  80
Ser Glu Thr Ser Leu Cys Gly Gly Lys Gly Lys Asn Ser Ser Gly Gly
                85                  90                  95
Gly Ala Ala Pro Glu Val Leu Arg Asp Phe Val Lys Lys Ser Leu Lys
                    100                 105                 110
Asp Gly Gly Gln Asn Trp Pro Thr Ser Arg Ala Thr Glu Ser Ser Pro
                115                 120                 125
Lys Thr Lys Ser Glu Thr Asn Asp Asn Ala Lys Ala Val Ala Lys Asp
                130                 135                 140
Leu Val Asp Leu Asn Pro Glu Glu Lys Thr Ile Val Ala Gly Leu Leu
145                 150                 155                 160
Ala Lys Thr Ile Glu Gly Gly Glu Val Val Glu Ile Arg Ala Val Ser
                    165                 170                 175
```

(2) INFORMATION FOR SEQ ID NO:15:

(i) SEQUENCE CHARACTERISTICS:
        (A) LENGTH: 1185 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: Ehrlichia (xi) SEQUENCE DESCRIPTION: SEQ ID NO:15:

```
GAAACAGCAT TGCTAGATTT CGTTGAACAA TTTGCTAATT TGCAACTAAA GCACTCATGA        60

TAAAGCTTGA TAGTATTTTA GAGGATAGTA GGCAATATGG TTTAGGGGAT TTCTTCGCAT       120

ACTTGTTATC ATCGTCCTTA TTTGTGCTTA GTTGGTCGGA TATTTGTGCA AGTTGTTGTA       180

AAATATGCAT ATTGTATGTA TAGGTGTGCA AGATATCATC TCTTTAGGTG TATCGTGTAG       240

CACTTAAACA AATGCTGGTG AACGTAGAGG GATTAAAGGA GGATTTGCGT ATATGTATGG       300

TATAGATATA GAGCTAAGTG ATTACAGAAT TGGTAGTGAA ACCATTTCCA GTGGAGATGA       360

TGGCTACTAC GAAGGATGTG CTTGTGACAA AGATGCCAGC ACTAATGCGT ACTCGTATGA       420

CAAGTGTAGG GTAGTACGGG AACGTGGAG ACCGAGCGAA CTGGTTTTAT ATGTTGGTGA        480

TGAGCATGTG GCATGTAGAG ATGTTGCTTC GGGTATGCAT CATGGTAATT TGCCAGGGGA       540

AGGTGTATTT TATAGAGGCA GAAGCGGGCA GAGCTGCTAC TGCTGAAGGT GGTGTTTATA       600

CTACCGTTGT GGAGGCATTA TCGCTGGTGC AAGAGGAAGA GGGTACAGGT ATGTACTTGA       660

TAAACGCACC AGAAAAAGCG GTCGTAAGGT TTTTCAAGAT AGAAAAGAGT GCAGCAGAGG       720

AACCTCAAAC AGTAGATCCT AGTGTAGTTG AGTCAGCAAC AGGGTCGGGT GTAGATACGC       780

AAGAAGAACA AGAAATAGAT CAAGAAGCAC CAGCAATTGA AGAAGTTGAG ACAGAAGAGC       840

AAGAAGTTAT TCTGGAAGAA GGTACTTTGA TAGATCTTGA GCAACCTGTA GCGCAAGTAC       900

CTGTAGTAGC TGAAGCAGAA TTACCTGGTG TTGAAGCTGC AGAAGCGATT GTACCATCAC       960

TAGAAGAAAA TAAGCTTCAA GAAGTGGTAG TTGCTCCAGA AGCGCAACAA CTAGAATCAG      1020

CTCCTGAAGT TTCTGCGCCA GCACAACCTG AGTCTACAGT TCTTGGTGTT GCTGAAGGTG      1080

ATCTAAAGTC TGAAGTATCT GTAGAAGCTA ATGCTGATGT ACGCAAAAAG AAGTAATCTC      1140

TGGTCCACRA GAGCAAGAAA TTGCAGAAGC ACTAGAGGGA ACTGA                      1185

(2) INFORMATION FOR SEQ ID NO:16:

(i) SEQUENCE CHARACTERISTICS:
        (A) LENGTH: 1131 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: Ehrlichia (xi) SEQUENCE DESCRIPTION: SEQ ID NO:16:

ATAAAGGGGC TCCAGCAACG CAGAGAGATG CTTATGGTAA GACGGCTTTA CATATAGCAG        60

CTGCTAATGG TGACGGTAAG CTATATAAGT TAATTGCGAA AAAATGCCCA GATAGCTGTC       120

AAGCACTCCT TTCTCATATG GGAGATACAG CGTTACATGA GGCTTTATAT TCTGATAAGG       180

TTACAGAAAA ATGCTTTTTA AAGATGCTTA AAGAGTCTCG AAAGCATTTG TCAAACTCAT       240

CTTTCGGAGA CTTGCTTAAT ACTCCTCAAG AAGCAAATGG TGACACGTTA CTGCATCTGG       300

CTGCATCGCG TGGTTTCGGT AAAGCATGTA AAATACTACT AAAGTCTGGG GCGTCAGTAT       360

CAGTCGTGAA TGTAGAGGGA AAAACACCGG TAGATGTTGC GGATCCATCA TTGAAAACTC       420

GTCCGTGGTT TTTTGGAAAG TCCGTTGTCA CAATGATGGC TGAACGTGTT CAAGTTCCTG       480

AAGGGGGATT CCCACCATAT CTGCCGCCTG AAAGTCCAAC TCCTTCTTTA GGATCTATTT       540

CAAGTTTTGA GAGTGTCTCT GCGCTATCAT CCTTGGGTAG TGGCCTAGAT ACTGCAGGAG       600

CTGAGGAGTC TATCTACGAA GAAATTAAGG ATACAGCAAA AGGTACAACG GAAGTTGAAA       660

GCACATATAC AACTGTAGGA GCTGAGGAGT CTATCTACGA AGAAATTAAG GATACAGCAA       720
```

```
AAGGTACAAC GGAAGTTGAA AGCACATATA CAACTGTAGG AGCTGAAGGT CCGAGAACAC      780

CAGAAGGTGA AGATCTGTAT GCTACTGTGG GAGCTGCAAT TACTTCCGAG GCGCAAGCAT      840

CAGATGCGGC GTCATCTAAG GGAGAAAGGC CGGAATCCAT TTATGCTGAT CCATTTGATA      900

TAGTGAAACC TAGGCAGGAA AGGCCTGAAT CTATCTATGC TGACCCATTT GCTGCGGAAC      960

GAACATCTTC TGGAGTAACG ACATTTGGCC CTAAGGAAGA GCCGATTTAT GCAACAGTGA     1020

AAAAGGGTCC TAAGAAGAGT GATACTTCTC AAAAAGAAGG AACAGCTTCT GAAAAAGTCG     1080

GCTCAACAAT AACTGTGATT AAGAAGAAAG TGAAACCTCA GGTTCCAGCT A              1131

(2) INFORMATION FOR SEQ ID NO:17:

(i) SEQUENCE CHARACTERISTICS:
        (A) LENGTH: 800 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: Ehrlichia (xi) SEQUENCE DESCRIPTION: SEQ ID NO:17:

AATGCGCTCC ACATAACTAG CATAACGTTT TCAGCAACGG CAGATCTTCA TATATAAGCA       60

CTGAACACCT ACGTTCCAAG ATCATGCTCT TCGCGCCTGT TTACTTGGTG GCTCAGAGTC      120

ATCATCACTA GGAGTTCGTG GTCTGTGAGA GCTAACTTGT GCTTCTTCCA GCGTATAACT      180

AGCACCTCCC AATCCTGATG CTGAAGGTTG ATCCCACGAA TAAGGCATAA TCCCTTGATC      240

CTGAGGTGGC ACATAGGGAG CTTGTGATCT TCCCATTCCA GTACTAGTAC CTCCTAGCCC      300

AGATGTTGAG AATTGGCTAG ATGGATAAGG AACATTCTCT AGGACACGTA GTATAATATG      360

AGGGGGGGGG GGAACGAGTT GAGCTCCCTG TCCGGCAGTA CCTCCCAATC CTGATGTTGA      420

GGGTTGATCC CATGATGTTG AGGGTTGATC CCACGATGTT GAAGGTTGTG CATACGAATA      480

GGGCATCATC CCTGGATCAT GTGGTGGAAT ATGCGAAGCT TGTTGACTTC CCATTCCAGC      540

GGCACTTCCT AACCCTGATG TTGAGGGTTG ATCCCACGAT GTTGAATGTT GTGCATACGA      600

ATAGGGCATC ATCCCTGGAT CATGTGGTGG AATATGCGAA GCTTGTTGAC TTCCCATTCC      660

AGCGGCACTT CCTAACCCTG ATGTTGAGGG TTGATCCCAC GATGTTGAAG GTTGTGCATA      720

CGAATAGGGC ATCATCCCTG GATCATGTGG TGGAATATGC GAAGCTTGTT GACTTCCCGT      780

TCCAGCGGCA CTTCCTAACC                                                  800

(2) INFORMATION FOR SEQ ID NO:18:

(i) SEQUENCE CHARACTERISTICS:
        (A) LENGTH: 1011 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: Ehrlichia (xi) SEQUENCE DESCRIPTION: SEQ ID NO:18:

AATGTATACA GTCTCAGATT CAGAATCTAT AACTTCTTTC GTTACTCCAC CAATGTTAAT       60

GGCGAATATC TCATCGACTA AGCGTTCAGG ATACTTGCTA TCATTGTCGG TAGAGCCATC      120
```

| | |
|---|---|
| TGACTTTTTT ACCGTGACAT TCTTTTTAAA AGAAACTCCA TTTACAACGG ACAATTCAGT | 180 |
| GCCATTTTGT AGCTTCGAGC GCAACTCCAC AGCAAATTCA CGTATTTTCT TCATACGTAA | 240 |
| TGCACTCTTC CATTCTTCAG TAAGAATAGA CCTGCTTTCT TCAAGTGTCC TTGGTCTTGG | 300 |
| AGGCACTACT TCAGTAACAA GAACGCCGAA ATAAGCGTCA CCATTGCTAA CCAGATGAGA | 360 |
| CGGTTTTCCT ACGGCAGATG AAAACGCCAA AGTAGTAAAG GCGTTTATAC CAAGCTGCAA | 420 |
| CGGAAAGTCT TTCACTAAGT TGCCAGATTT ATCGAGCCCA TGCATATCAA AATTCGTCAA | 480 |
| AACACCACTG ATCCGCGCAC CAAACATATC CTTTAGTTCA TTCAGCAATG CCCCGCGGCT | 540 |
| GATCATATCG TTTGCTTTTT TCACATTGCT AACTAGCAAC TCACCTGCCT TTTGCCTTCT | 600 |
| AATATTTGAA GATATCTTCT CTTTCAGCTT TTCTAGGTCT TCCTTAGTGA TCTCATGCTT | 660 |
| CCTTATTACC TTCATGATAT GCCAGCCGAC AACGCTACGG AACATTTCAC TGACTTCTCC | 720 |
| TTCATTTAGT GCAAACACCA CATTTCGCAC ACCTACCGGA AGAACATCCT TAGAGATATT | 780 |
| ATTGAGTGCA ATATCCTCTA TGGTGTAGCC AGCATCACTA ACCAATTCCT CAAAAGACTT | 840 |
| ACCCTCTTGG TAAGCTTTGT AAGCTAGCTC AGCTTCATTT TTGTCTGTAA ATACTAAATT | 900 |
| TAGAACATCT CTTTGATCAT GTAGTTCACT GTTTTTAATC TCAACGTCTA CCTTCTTGAT | 960 |
| CCGAAACAAT GACATCAGCA AGCAAGTCGT CTTCTGCCAT GATTATATGA T | 1011 |

(2) INFORMATION FOR SEQ ID NO:19:

(i) SEQUENCE CHARACTERISTICS:
        (A) LENGTH: 513 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: Ehrlichia (xi) SEQUENCE DESCRIPTION: SEQ ID NO:19:

| | |
|---|---|
| GCAAATATTT TTCTTGGTGC CGCCCTAAAA GCCTGAAAAA TTTAAAGAAA TGTTACTGCT | 60 |
| CTAGTCATTC ATAAAATGCA AATAGCCTAC AGAAGGAGTA TTTACTGCTA TAGGCTTGAA | 120 |
| AGTGCAATCG TTATTTACTA TTTTTTATAC ATATCGCAGT ACAGAGATTT TACGCGCTAC | 180 |
| GCCTGTGCAT CATAGCCGTA TTGCATCAAT AAATTGTCGT TGCTACGCGG GAAAGCTGCT | 240 |
| TAGCGCTTGA CCATTTTTCA TACACATTGT ACCATCATAG CGAGTGTGGT GCTCATGAGA | 300 |
| GTGCGTAGTG TTGCCGCCGG TTTCTCATGT TATAATCTTG CTGCCGTTTT GTGCAGAAGG | 360 |
| AGGAGTAGTC TCGTTTTTTT CCAAAAGACA ATGTGCTGGA GTGTCCCGGT GAGCCTCAAG | 420 |
| GTTCTTGTGG GATTTGTGTG GGCTGTTGTA TAAATACCAC GTTCGAAGCT GTCCTAGTGT | 480 |
| ATTCAGCATA TGTTGAGGAA GTTGTTGCTA TGA | 513 |

(2) INFORMATION FOR SEQ ID NO:20:

(i) SEQUENCE CHARACTERISTICS:
        (A) LENGTH: 464 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: Ehrlichia (xi) SEQUENCE DESCRIPTION: SEQ ID NO:20:

```
AGTCATTGAG TCGAGGGTAG TCTTGTGGAT CCCTGATAAA TGTTCTAAAA TTTAAAACAA      60

CACTAGAGTT TTGATCACAT GTTGGTTGTC AGAAAAAAAA TGTCAAAAAA TTTACCAGGG     120

CTTTTTGAAA TGCCTAGATT TTCCATTTCT CAATGAAACT TGTTTGATCA TGACTATTCC     180

AGCTAATGGA GCAGTGTGAT GTAGAGGAAG GAGCCACTGA GGGTATGTGG GGTGTTAGAC     240

TGGATCATCA TTCTTCAAGG CGTGTTCCTT GGAATGCCTG GGAGGAGAGC AATTTTCTAT     300

TAAAATTTAA TTCGCCTCCT TCCAAATATG GTTCCCTGGA CGATTTAGCA AATAGCATTC     360

CTTTTTTGGA GATTCAAAAA GCACATTAGC ATTGAGGATT GCTACAGTAA AGAAATCTGC     420

CTAACTTTGT TTTATCCAGT ATTGCCTAAA ATTATTGGAC CACT                     464

(2) INFORMATION FOR SEQ ID NO:21:

(i) SEQUENCE CHARACTERISTICS:
        (A) LENGTH: 527 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: Ehrlichia (xi) SEQUENCE DESCRIPTION: SEQ ID NO:21:

CCTATGGCAG CTCTAAACTC GGCACGACTG GTTTCTACAA GAGATTGGTC GACATTAAAC      60

CATGCGAAAT CATTGCGATC AATTCTTCCT TCTTTTTCCT GTATAGCACT ACAGACTTCC     120

TCTGCACTAG AAGCCACTCG TGTCCCGATG CGTACGTCAC GGATGCAAAG CCCCAGGTCT     180

TTTACGCTGC CGGGTGTGTC TATATCTTCC ACAACATAAT CAACGCAAGC GTGAATATGG     240

ATACCAGAAA CAGAGGTAAC CCTGTATACT AAATGCTCTT CCAAAACATG TTGATTAACA     300

GGTAAGCGCC TAGCACTATC ACCATTATCA GCAACAACGC CTTCATGCGC AACGTAATGA     360

GCAGCGAGCT CAACTGGCAG AGATGACCCA CTACTGTTAC TCAAGATACT AGATAAGAGT     420

ACCCGGAGAT TTTCTGTGTT TACACCAGTT TTCTCCACAA TATTTGCAGC ATGCTTCGGC     480

TGTGACCTTA AGATTTCACG TATTTCATCG GAGTGTTGTA TGAAAAT                  527

(2) INFORMATION FOR SEQ ID NO:22:

(i) SEQUENCE CHARACTERISTICS:
        (A) LENGTH: 464 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: Ehrlichia (xi) SEQUENCE DESCRIPTION: SEQ ID NO:22:

TTCACCTGGC CAAATCTTAT TGGATCTTCA GGACAAAGAC CAAGAATCTG CTTCTCCAAG      60

AAGCATTCTC TGACCCCCAC CTACCTATCT GACTCTTAGC TTAGATTCCT AATGGTGTGA     120

GTGTGTCAGA GCCTTTACTT AGTCTAAGCG TAACTGTAAA AACATCTTTT CAAAAGTCTC     180

TGCATGACTG TCTAGGTCTC ACCTATCACA CTGTAAGCAT CTGGAAAACA AAGCCACTGA     240

GTCTTCCTTT TACCAAAAAG GCCTAGCCTT GTTTTTGACA AATGGCAAGA ACACATTAGA     300

TGTTTGTTGA GAGAACAAAA GGAGAGAACT CATTATGAAA CTCTGGACAA CATTTATATA     360
```

```
CCTCTCTACA TTTTTTGTGT TGGAGGTTAG TTTTCTTTTC TAATAATTTG ATTTCTTTGG      420

ATACATCGAG GCAATACACT TAAGAAGCAA GAAGATTGGG GGCC                      464
```

(2) INFORMATION FOR SEQ ID NO:23:

(i) SEQUENCE CHARACTERISTICS:
        (A) LENGTH: 233 amino acids
        (B) TYPE: amino acid
        (C) STRANDEDNESS: single
        (D) TOPOLOGY: linear (ii) MOLECULE TYPE: protein (vi) ORIGINAL SOURCE:
        (A) ORGANISM: Ehrlichia (xi) SEQUENCE DESCRIPTION: SEQ ID NO:23:

```
Tyr Gly Glu Arg Gly Asp Arg Ala Asn Trp Phe Tyr Met Leu Val Met
1               5                   10                  15

Ser Met Trp His Val Glu Met Leu Leu Arg Val Cys Ile Met Val Ile
            20                  25                  30

Cys Gln Gly Lys Val Tyr Phe Ile Glu Ala Glu Ala Gly Arg Ala Ala
        35                  40                  45

Thr Ala Glu Gly Gly Val Tyr Thr Thr Val Val Glu Ala Leu Ser Leu
    50                  55                  60

Val Gln Glu Glu Glu Gly Thr Gly Met Tyr Leu Ile Asn Ala Pro Glu
65                  70                  75                  80

Lys Ala Val Val Arg Phe Phe Lys Ile Glu Lys Ser Ala Ala Glu Glu
                85                  90                  95

Pro Gln Thr Val Asp Pro Ser Val Val Glu Ser Ala Thr Gly Ser Gly
            100                 105                 110

Val Asp Thr Gln Glu Glu Gln Glu Ile Asp Gln Glu Ala Pro Ala Ile
        115                 120                 125

Glu Glu Val Glu Thr Glu Glu Gln Glu Val Ile Leu Glu Glu Gly Thr
    130                 135                 140

Leu Ile Asp Leu Glu Gln Pro Val Ala Gln Val Pro Val Val Ala Glu
145                 150                 155                 160

Ala Glu Leu Pro Gly Val Glu Ala Ala Glu Ala Ile Val Pro Ser Leu
                165                 170                 175

Glu Glu Asn Lys Leu Gln Glu Val Val Val Ala Pro Glu Ala Gln Gln
            180                 185                 190

Leu Glu Ser Ala Pro Glu Val Ser Ala Pro Ala Gln Pro Glu Ser Thr
        195                 200                 205

Val Leu Gly Val Ala Glu Gly Asp Leu Lys Ser Glu Val Ser Val Glu
    210                 215                 220

Ala Asn Ala Asp Val Arg Lys Lys Lys
225                 230
```

(2) INFORMATION FOR SEQ ID NO:24:

(i) SEQUENCE CHARACTERISTICS:
        (A) LENGTH: 376 amino acids
        (B) TYPE: amino acid
        (C) STRANDEDNESS: single
        (D) TOPOLOGY: linear (ii) MOLECULE TYPE: protein (vi) ORIGINAL SOURCE:
        (A) ORGANISM: Ehrlichia (xi) SEQUENCE DESCRIPTION: SEQ ID NO:24:

```
Lys Gly Ala Pro Ala Thr Gln Arg Asp Ala Tyr Gly Lys Thr Ala Leu
1               5                   10                  15

His Ile Ala Ala Ala Asn Gly Asp Gly Lys Leu Tyr Lys Leu Ile Ala
            20                  25                  30

Lys Lys Cys Pro Asp Ser Cys Gln Ala Leu Leu Ser His Met Gly Asp
            35                  40                  45

Thr Ala Leu His Glu Ala Leu Tyr Ser Asp Lys Val Thr Glu Lys Cys
        50                  55                  60

Phe Leu Lys Met Leu Lys Glu Ser Arg Lys His Leu Ser Asn Ser Ser
65                  70                  75                  80

Phe Gly Asp Leu Leu Asn Thr Pro Gln Glu Ala Asn Gly Asp Thr Leu
                85                  90                  95

Leu His Leu Ala Ala Ser Arg Gly Phe Gly Lys Ala Cys Lys Ile Leu
                100                 105                 110

Leu Lys Ser Gly Ala Ser Val Ser Val Asn Val Glu Gly Lys Thr
            115                 120                 125

Pro Val Asp Val Ala Asp Pro Ser Leu Lys Thr Arg Pro Trp Phe Phe
            130                 135                 140

Gly Lys Ser Val Val Thr Met Met Ala Glu Arg Val Gln Val Pro Glu
145                 150                 155                 160

Gly Gly Phe Pro Pro Tyr Leu Pro Pro Glu Ser Pro Thr Pro Ser Leu
                165                 170                 175

Gly Ser Ile Ser Ser Phe Glu Ser Val Ser Ala Leu Ser Ser Leu Gly
                180                 185                 190

Ser Gly Leu Asp Thr Ala Gly Ala Glu Glu Ser Ile Tyr Glu Glu Ile
            195                 200                 205

Lys Asp Thr Ala Lys Gly Thr Thr Glu Val Glu Ser Thr Tyr Thr Thr
    210                 215                 220

Val Gly Ala Glu Glu Ser Ile Tyr Glu Glu Ile Lys Asp Thr Ala Lys
225                 230                 235                 240

Gly Thr Thr Glu Val Glu Ser Thr Tyr Thr Thr Val Gly Ala Glu Gly
                245                 250                 255

Pro Arg Thr Pro Glu Gly Glu Asp Leu Tyr Ala Thr Val Gly Ala Ala
            260                 265                 270

Ile Thr Ser Glu Ala Gln Ala Ser Asp Ala Ala Ser Ser Lys Gly Glu
        275                 280                 285

Arg Pro Glu Ser Ile Tyr Ala Asp Pro Phe Asp Ile Val Lys Pro Arg
    290                 295                 300

Gln Glu Arg Pro Glu Ser Ile Tyr Ala Asp Pro Phe Ala Ala Glu Arg
305                 310                 315                 320

Thr Ser Ser Gly Val Thr Thr Phe Gly Pro Lys Glu Glu Pro Ile Tyr
                325                 330                 335

Ala Thr Val Lys Lys Gly Pro Lys Lys Ser Asp Thr Ser Gln Lys Glu
            340                 345                 350

Gly Thr Ala Ser Glu Lys Val Gly Ser Thr Ile Thr Val Ile Lys Lys
            355                 360                 365

Lys Val Lys Pro Gln Val Pro Ala
370                 375
```

(2) INFORMATION FOR SEQ ID NO:25:

(i) SEQUENCE CHARACTERISTICS:
        (A) LENGTH: 148 amino acids (B) TYPE: amino acid
          (C) STRANDEDNESS: single
          (D) TOPOLOGY: linear (ii) MOLECULE TYPE: protein (vi) ORIGINAL SOURCE:
          (A) ORGANISM: Ehrlichia (xi) SEQUENCE DESCRIPTION: SEQ ID NO:25:

Tyr Glu Gly Gly Gly Glu Arg Val Glu Leu Pro Val Arg Gln Tyr Leu
1               5                   10                  15

Pro Ile Leu Met Leu Arg Val Asp Pro Met Met Leu Arg Val Asp Pro
                20                  25                  30

Thr Met Leu Lys Val Val His Thr Asn Arg Ala Ser Ser Leu Asp His
            35                  40                  45

Val Val Glu Tyr Ala Lys Leu Val Asp Phe Pro Phe Gln Arg His Phe
        50                  55                  60

Leu Thr Leu Met Leu Arg Val Asp Pro Thr Met Leu Lys Val Val His
65                  70                  75                  80

Thr Asn Arg Ala Ser Ser Leu Asp His Val Val Glu Tyr Ala Lys Leu
                85                  90                  95

Val Asp Phe Pro Phe Gln Arg His Phe Leu Thr Leu Met Leu Arg Val
            100                 105                 110

Asp Pro Thr Met Leu Lys Val Val His Thr Asn Arg Ala Ser Ser Leu
        115                 120                 125

Asp His Val Val Glu Tyr Ala Lys Leu Val Asp Phe Pro Phe Gln Arg
    130                 135                 140

His Phe Leu Thr
145

(2) INFORMATION FOR SEQ ID NO:26:

(i) SEQUENCE CHARACTERISTICS:
          (A) LENGTH: 89 amino acids
          (B) TYPE: amino acid
          (C) STRANDEDNESS: single
          (D) TOPOLOGY: linear (ii) MOLECULE TYPE: protein (vi) ORIGINAL SOURCE:
          (A) ORGANISM: Ehrlichia (xi) SEQUENCE DESCRIPTION: SEQ ID NO:26:

Tyr Gly Ser Ser Lys Leu Gly Thr Thr Gly Phe Tyr Lys Arg Leu Val
1               5                   10                  15

Asp Ile Lys Pro Cys Glu Ile Ile Ala Ile Asn Ser Ser Phe Phe Phe
                20                  25                  30

Leu Tyr Ser Thr Thr Asp Phe Leu Cys Thr Arg Ser His Ser Cys Pro
            35                  40                  45

Asp Ala Tyr Val Thr Asp Ala Lys Pro Gln Val Phe Tyr Ala Ala Gly
        50                  55                  60

Cys Val Tyr Ile Phe His Asn Ile Ile Asn Ala Ser Val Asn Met Asp
65                  70                  75                  80

Thr Arg Asn Arg Gly Asn Pro Val Tyr
                85

(2) INFORMATION FOR SEQ ID NO:27:

(i) SEQUENCE CHARACTERISTICS:

```
            (A) LENGTH: 238 amino acids
            (B) TYPE: amino acid
            (C) STRANDEDNESS: single
            (D) TOPOLOGY: linear (ii) MOLECULE TYPE: protein (vi) ORIGINAL SOURCE:
            (A) ORGANISM: Ehrlichia (xi) SEQUENCE DESCRIPTION: SEQ ID NO:27:

Leu Gly Ser Ala Ala Gly Thr Gly Ser Gln Gln Ala Ser His Ile Pro
1               5                   10                  15

Pro His Asp Pro Gly Met Met Pro Tyr Ser Tyr Ala Gln Pro Ser Thr
            20                  25                  30

Ser Trp Asp Gln Pro Ser Thr Ser Gly Leu Gly Ser Ala Ala Gly Met
        35                  40                  45

Gly Ser Gln Gln Ala Ser His Ile Pro Pro His Asp Pro Gly Met Met
    50                  55                  60

Pro Tyr Ser Tyr Ala Gln Pro Ser Thr Ser Trp Asp Gln Pro Ser Thr
65                  70                  75                  80

Ser Gly Leu Gly Ser Ala Ala Gly Met Gly Ser Gln Gln Ala Ser His
                85                  90                  95

Ile Pro Pro His Asp Pro Gly Met Met Pro Tyr Ser Tyr Ala Gln Pro
            100                 105                 110

Ser Thr Ser Trp Asp Gln Pro Ser Thr Ser Trp Asp Gln Pro Ser Thr
        115                 120                 125

Ser Gly Leu Gly Gly Thr Ala Gly Gln Gly Ala Gln Leu Val Pro Pro
    130                 135                 140

Pro Pro His Ile Ile Leu Arg Val Leu Glu Asn Val Pro Tyr Pro Ser
145                 150                 155                 160

Ser Gln Phe Ser Thr Ser Gly Leu Gly Gly Thr Ser Thr Gly Met Gly
                165                 170                 175

Arg Ser Gln Ala Pro Tyr Val Pro Pro Gln Asp Gln Gly Ile Met Pro
            180                 185                 190

Tyr Ser Trp Asp Gln Pro Ser Ala Ser Gly Leu Gly Gly Ala Ser Tyr
        195                 200                 205

Thr Leu Glu Glu Ala Gln Val Ser Ser His Arg Pro Arg Thr Pro Ser
    210                 215                 220

Asp Asp Asp Ser Glu Pro Pro Ser Lys Gln Ala Arg Arg Ala
225                 230                 235

(2) INFORMATION FOR SEQ ID NO:28:

(i) SEQUENCE CHARACTERISTICS:
            (A) LENGTH: 334 amino acids
            (B) TYPE: amino acid
            (C) STRANDEDNESS: single
            (D) TOPOLOGY: linear (ii) MOLECULE TYPE: protein (vi) ORIGINAL SOURCE:
            (A) ORGANISM: Ehrlichia (xi) SEQUENCE DESCRIPTION: SEQ ID NO:28:

Ser Trp Gln Lys Thr Thr Cys Leu Leu Met Ser Leu Phe Arg Ile Lys
1               5                   10                  15

Lys Val Asp Val Glu Ile Lys Asn Ser Glu Leu His Asp Gln Arg Asp
            20                  25                  30
```

-continued

```
Val Leu Asn Leu Val Phe Thr Asp Lys Asn Glu Ala Glu Leu Ala Tyr
            35                  40                  45
Lys Ala Tyr Gln Glu Gly Lys Ser Phe Glu Glu Leu Val Ser Asp Ala
 50                  55                  60
Gly Tyr Thr Ile Glu Asp Ile Ala Leu Asn Asn Ile Ser Lys Asp Val
 65                      70                  75                  80
Leu Pro Val Gly Val Arg Asn Val Val Phe Ala Leu Asn Glu Gly Glu
                 85                  90                  95
Val Ser Glu Met Phe Arg Ser Val Gly Trp His Ile Met Lys Val
                100                 105                 110
Ile Arg Lys His Glu Ile Thr Lys Glu Asp Leu Glu Lys Leu Lys Glu
            115                 120                 125
Lys Ile Ser Ser Asn Ile Arg Arg Gln Lys Ala Gly Glu Leu Leu Val
    130                 135                 140
Ser Asn Val Lys Lys Ala Asn Asp Met Ile Ser Arg Gly Ala Leu Leu
145                 150                 155                 160
Asn Glu Leu Lys Asp Met Phe Gly Ala Arg Ile Ser Gly Val Leu Thr
                165                 170                 175
Asn Phe Asp Met His Gly Leu Asp Lys Ser Gly Asn Leu Val Lys Asp
                180                 185                 190
Phe Pro Leu Gln Leu Gly Ile Asn Ala Phe Thr Thr Leu Ala Phe Ser
        195                 200                 205
Ser Ala Val Gly Lys Pro Ser His Leu Val Ser Asn Gly Asp Ala Tyr
    210                 215                 220
Phe Gly Val Leu Val Thr Glu Val Val Pro Arg Pro Arg Thr Leu
225                 230                 235                 240
Glu Glu Ser Arg Ser Ile Leu Thr Glu Glu Trp Lys Ser Ala Leu Arg
                245                 250                 255
Met Lys Lys Ile Arg Glu Phe Ala Val Glu Leu Arg Ser Lys Leu Gln
                260                 265                 270
Asn Gly Thr Glu Leu Ser Val Val Asn Gly Val Ser Phe Lys Lys Asn
        275                 280                 285
Val Thr Val Lys Lys Ser Asp Gly Ser Thr Asp Asn Asp Ser Lys Tyr
290                 295                 300
Pro Glu Arg Leu Val Asp Glu Ile Phe Ala Ile Asn Ile Gly Gly Val
305                 310                 315                 320
Thr Lys Glu Val Ile Asp Ser Glu Ser Glu Thr Val Tyr Ile
                325                 330
```

(2) INFORMATION FOR SEQ ID NO:29:

(i) SEQUENCE CHARACTERISTICS:
        (A) LENGTH: 175 amino acids
        (B) TYPE: amino acid
        (C) STRANDEDNESS: single
        (D) TOPOLOGY: linear (ii) MOLECULE TYPE: protein (vi) ORIGINAL SOURCE:
        (A) ORGANISM: Ehrlichia (xi) SEQUENCE DESCRIPTION: SEQ ID NO:29:

```
Ile Phe Ile Gln His Ser Asp Glu Ile Arg Glu Ile Leu Arg Ser Gln
 1               5                  10                  15
Pro Lys His Ala Ala Asn Ile Val Glu Lys Thr Gly Val Asn Thr Glu
            20                  25                  30
```

```
Asn Leu Arg Val Leu Leu Ser Ser Ile Leu Ser Asn Ser Ser Gly Ser
            35                  40                  45

Ser Leu Pro Val Glu Leu Ala Ala His Tyr Val Ala His Glu Gly Val
        50                  55                  60

Val Ala Asp Asn Gly Asp Ser Ala Arg Arg Leu Pro Val Asn Gln His
65                  70                  75                  80

Val Leu Glu Glu His Leu Val Tyr Arg Val Thr Ser Val Ser Gly Ile
                85                  90                  95

His Ile His Ala Cys Val Asp Tyr Val Val Glu Asp Ile Asp Thr Pro
            100                 105                 110

Gly Ser Val Lys Asp Leu Gly Leu Cys Ile Arg Asp Val Arg Ile Gly
        115                 120                 125

Thr Arg Val Ala Ser Ser Ala Glu Glu Val Cys Ser Ala Ile Gln Glu
130                 135                 140

Lys Glu Gly Arg Ile Asp Arg Asn Asp Phe Ala Trp Phe Asn Val Asp
145                 150                 155                 160

Gln Ser Leu Val Glu Thr Ser Arg Ala Glu Phe Arg Ala Ala Ile
                165                 170                 175
```

(2) INFORMATION FOR SEQ ID NO:30:

(i) SEQUENCE CHARACTERISTICS:
        (A) LENGTH: 41 amino acids
        (B) TYPE: amino acid
        (C) STRANDEDNESS: single
        (D) TOPOLOGY: linear (ii) MOLECULE TYPE: peptide (vi) ORIGINAL SOURCE:
        (A) ORGANISM: Ehrlichia (ix) FEATURE:
        (A) NAME/KEY: Modified-site
        (B) LOCATION: 7
        (D) OTHER INFORMATION: /note= "Where Xaa is either a Met
            or Thr"

(xi) SEQUENCE DESCRIPTION: SEQ ID NO:30:

```
Leu Gly Ser Ala Ala Gly Xaa Gly Ser Gln Gln Ala Ser His Ile Pro
1               5                   10                  15

Pro His Asp Pro Gly Met Met Pro Tyr Ser Tyr Ala Gln Pro Ser Thr
            20                  25                  30

Ser Trp Asp Gln Pro Ser Thr Ser Gly
        35                  40
```

(2) INFORMATION FOR SEQ ID NO:31:

(i) SEQUENCE CHARACTERISTICS:
        (A) LENGTH: 860 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: Ehrlichia (xi) SEQUENCE DESCRIPTION: SEQ ID NO:31:

```
AAAAGCTTAA GGAAGATGTG GCTTCTATGT CGGATGAGGC TTTGCTGAAG TTTGCCAATA      60

GGCTCAGAAG AGGTGTTCCT ATGGCTGCTC CGGTGTTTGA GGGTCCGAAG GATGCGCAGA     120

TTTCCCGGCT TTTGGAATTA GCGGATGTTG ATCCGTCTGG GCAGGTGGAT CTTTATGATG     180
```

```
GGCGTTCAGG GCAGAAGTTT GATCGCAAGG TAACTGTTGG ATACATTTAC ATGTTGAAGC      240

TCCATCACTT GGTGGATGAC AAGATACATG CTAGGTCTGT TGGTCCGTAT GGTCTGGTTA      300

CTCAGCAACC TCTTGGAGGA AAGTCGCACT TTGGTGGGCA GAGATTTGGG GAAATGGAAT      360

GCTGGGCATT GCAGGCCTAT GGTGCTGCTT ATACTTTGCA GGAAATGCTA ACTGTCAAAT      420

CTGACGATAT CGTAGGTAGG GTAACAATCT ATGAATCCAT AATTAAGGGG GATAGCAACT      480

TCGAGTGTGG TATTCCTGAG TCGTTTAATG TCATGGTCAA GGAGTTACGC TCGCTGTGCC      540

TTGATGTTGT TCTAAAGCAG GATAAAGAGT TTACTAGTAG CAAGGTGGAG TAGGGATTTA      600

CAATTATGAA GACGTTGGAT TTGTATGGCT ATACCAGTAT AGCACAGTCG TTCGATAACA      660

TTTGCATATC CATATCTAGT CCACAAAGTA TAAGGGCTAT GTCCTATGGA GAAATCAAGG      720

ATATCTCTAC TACTATCTAT CGTACCTTTA AGGTGGAGAA GGGGGGGCTA TTCTGTCCTA      780

AGATCTTTGG TCCGGTTAAT GATGACGAGT GTCTTTGTGG TAAGTATAGG AAAAAGCGCT      840

ACAGGGGCAT TGTCTGTGAA                                                   860
```

(2) INFORMATION FOR SEQ ID NO:32:

(i) SEQUENCE CHARACTERISTICS:
        (A) LENGTH: 196 amino acids
        (B) TYPE: amino acid
        (C) STRANDEDNESS: single
        (D) TOPOLOGY: linear (ii) MOLECULE TYPE: protein (vi) ORIGINAL SOURCE:
        (A) ORGANISM: Ehrlichia (xi) SEQUENCE DESCRIPTION: SEQ ID NO:32:

```
Lys Leu Lys Glu Asp Val Ala Ser Met Ser Asp Glu Ala Leu Leu Lys
 1               5                  10                  15

Phe Ala Asn Arg Leu Arg Arg Gly Val Pro Met Ala Ala Pro Val Phe
                20                  25                  30

Glu Gly Pro Lys Asp Ala Gln Ile Ser Arg Leu Leu Glu Leu Ala Asp
            35                  40                  45

Val Asp Pro Ser Gly Gln Val Asp Leu Tyr Asp Gly Arg Ser Gly Gln
50                  55                  60

Lys Phe Asp Arg Lys Val Thr Val Gly Tyr Ile Tyr Met Leu Lys Leu
65                  70                  75                  80

His His Leu Val Asp Asp Lys Ile His Ala Arg Ser Val Gly Pro Tyr
                85                  90                  95

Gly Leu Val Thr Gln Gln Pro Leu Gly Gly Lys Ser His Phe Gly Gly
            100                 105                 110

Gln Arg Phe Gly Glu Met Glu Cys Trp Ala Leu Gln Ala Tyr Gly Ala
        115                 120                 125

Ala Tyr Thr Leu Gln Glu Met Leu Thr Val Lys Ser Asp Asp Ile Val
    130                 135                 140

Gly Arg Val Thr Ile Tyr Glu Ser Ile Ile Lys Gly Asp Ser Asn Phe
145                 150                 155                 160

Glu Cys Gly Ile Pro Glu Ser Phe Asn Val Met Val Lys Glu Leu Arg
                165                 170                 175

Ser Leu Cys Leu Asp Val Val Leu Lys Gln Asp Lys Glu Phe Thr Ser
            180                 185                 190

Ser Lys Val Glu
        195
```

(2) INFORMATION FOR SEQ ID NO:33:

(i) SEQUENCE CHARACTERISTICS:
        (A) LENGTH: 89 amino acids
        (B) TYPE: amino acid
        (C) STRANDEDNESS: single
        (D) TOPOLOGY: linear (ii) MOLECULE TYPE: protein (vi) ORIGINAL SOURCE:
        (A) ORGANISM: Ehrlichia (xi) SEQUENCE DESCRIPTION: SEQ ID NO:33:

```
Gly Phe Thr Ile Met Lys Thr Leu Asp Leu Tyr Gly Tyr Thr Ser Ile
  1               5                  10                  15

Ala Gln Ser Phe Asp Asn Ile Cys Ile Ser Ile Ser Ser Pro Gln Ser
             20                  25                  30

Ile Arg Ala Met Ser Tyr Gly Glu Ile Lys Asp Ile Ser Thr Thr Ile
         35                  40                  45

Tyr Arg Thr Phe Lys Val Glu Lys Gly Gly Leu Phe Cys Pro Lys Ile
 50                  55                  60

Phe Gly Pro Val Asn Asp Asp Glu Cys Leu Cys Gly Lys Tyr Arg Lys
 65                  70                  75                  80

Lys Arg Tyr Arg Gly Ile Val Cys Glu
                 85
```

(2) INFORMATION FOR SEQ ID NO:34:

(i) SEQUENCE CHARACTERISTICS:
        (A) LENGTH: 484 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: Ehrlichia (xi) SEQUENCE DESCRIPTION: SEQ ID NO:34:

```
ATCATAAGCT TTACATGTCC TATCCAGGCG ATTATCCCTA TCCATAGCAT AGTAACGCCC    60
TGCAACAGTA GCAATTTCGG CATTTAAGTG CTCAATTTTA GCGTTCAGCA TACCGATATA   120
CTTCTCAGCA GAACGCGGTG AACATCCCT ACCATCTAGA ATTACATGTA TAAAAACCTT    180
GATGCCAAAT CCGGTGATAA CCTCAATAAT GGTTTCCATG TGCGCCTGAA GAGAATGCAC   240
TCCACCATCA GAAAGCAGAC CAATCATGTG GCATACCCCA CCCTTCGCCT GTATATCGCG   300
CACAAAGTCC AACAATTTAG GATTCTTGTG AACCTCATTA ATCTCAAGAT TAATTCTCAA   360
CAGATCCTGA AGCACTATCC TGCCGCATCC TATACTTATG TGCCCTACTT CTGAATTCCC   420
GAACTGACCT GAAGGCAATC CGACATCCGT TCCACTAGCA GACAAACTAC TCATAGGACA   480
GCAT                                                                484
```

(2) INFORMATION FOR SEQ ID NO:35:

(i) SEQUENCE CHARACTERISTICS:
        (A) LENGTH: 161 amino acids
        (B) TYPE: amino acid
        (C) STRANDEDNESS: single
        (D) TOPOLOGY: linear (ii) MOLECULE TYPE: protein (vi) ORIGINAL SOURCE:
    (A) ORGANISM: Ehrlichia (xi) SEQUENCE DESCRIPTION: SEQ ID NO:35:

```
Cys Cys Pro Met Ser Ser Leu Ser Ala Ser Gly Thr Asp Val Gly Leu
1               5                   10                  15

Pro Ser Gly Gln Phe Gly Asn Ser Glu Val Gly His Ile Ser Ile Gly
            20                  25                  30

Cys Gly Arg Ile Val Leu Gln Asp Leu Leu Arg Ile Asn Leu Glu Ile
        35                  40                  45

Asn Glu Val His Lys Asn Pro Lys Leu Leu Asp Phe Val Arg Asp Ile
50                  55                  60

Gln Ala Lys Gly Gly Val Cys His Met Ile Gly Leu Leu Ser Asp Gly
65                  70                  75                  80

Gly Val His Ser Leu Gln Ala His Met Glu Thr Ile Ile Glu Val Ile
                85                  90                  95

Thr Gly Phe Gly Ile Lys Val Phe Ile His Val Ile Leu Asp Gly Arg
            100                 105                 110

Asp Val Pro Pro Arg Ser Ala Glu Lys Tyr Ile Gly Met Leu Asn Ala
        115                 120                 125

Lys Ile Glu His Leu Asn Ala Glu Ile Ala Thr Val Ala Gly Arg Tyr
130                 135                 140

Tyr Ala Met Asp Arg Asp Asn Arg Leu Asp Arg Thr Cys Lys Ala Tyr
145                 150                 155                 160

Asp
```

(2) INFORMATION FOR SEQ ID NO:36:

(i) SEQUENCE CHARACTERISTICS:
        (A) LENGTH: 1039 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: Ehrlichia (xi) SEQUENCE DESCRIPTION: SEQ ID NO:36:

| | | | | | |
|---|---|---|---|---|---|
| TTAATCAGAG | CGGTTGTGCT | AGTCCTTTCC | GAAATTCCTG | TGCTGAATGC | GGAGATTTCA | 60 |
| GGCGATGATA | TAGTCTACAG | GGACTATTGT | AACATTGGAG | TCGCGGTAGG | TACCGATAAG | 120 |
| GGGTTAGTGG | TGCCTGTTAT | CAGAAGAGCG | GAAACTATGT | CACTTGCTGA | AATGGAGCAA | 180 |
| GCACTTGTTG | ACTTAAGTAC | AAAAGCAAGA | AGTGGCAAGC | TCTCTGTTTC | TGATATGTCT | 240 |
| GGTGCAACCT | TTACTATTAC | CAATGGTGGT | GTGTATGGGT | CGCTATTGTC | TACCCCTATA | 300 |
| ATCAACCCTC | CTCAATCTGG | AATCTTGGGT | ATGCATGCTA | TACAGCAGCG | TCCTGTGGCA | 360 |
| GTAGATGGTA | AGGTAGAGAT | AAGGCCTATG | ATGTATTTGG | CGCTATCATA | TGATCATAGA | 420 |
| ATAGTTGACG | GGCAAGGTGC | TGTGACGTTT | TTGGTAAGAG | TGAAGCAGTA | CATAGAAGAT | 480 |
| CCTAACAGAT | TGGCTCTAGG | AATTTAGGGG | GTTTTTATGG | GGCGGGGTAC | AATAACCATC | 540 |
| CACTCCAAAG | AGGATTTTGC | CTGTATGAGA | AGGGCTGGGA | TGCTTGCAGC | TAAGGTGCTT | 600 |
| GATTTTATAA | CGCCGCATGT | TGTTCCTGGT | GTGACTACTA | ATGCTCTGAA | TGATCTATGT | 660 |
| CACGATTTCA | TCATTTCTGC | CGGGGCTATT | CCAGCGCCTT | TGGGCTATAG | AGGGTATCCT | 720 |
| AAGTCTATTT | GTACTTCGAA | GAATTTTGTG | GTTTGCCATG | GCATTCCAGA | TGATATTGCA | 780 |

```
TTAAAAAACG GCGATATAGT TAACATAGAC GTTACTGTGA TCCTCGATGG TTGGCACGGG        840

GATACTAATA GGATGTATTG GGTTGGTGAT AACGTCTCTA TTAAGGCTAA GCGCATTTGT        900

GAGGCAAGTT ATAAGGCATT GATGGCGGCG ATTGGTGTAA TACAGCCAGG TAAGAAGCTC        960

AATAGCATAG GGTTAGCTAT AGAGGAAGAA ATCAGAGGTT ATGGATACTC CATTGTTAGA       1020

GATTACTGCG GACATGGGA                                                    1039
```

(2) INFORMATION FOR SEQ ID NO:37:

(i) SEQUENCE CHARACTERISTICS:
        (A) LENGTH: 168 amino acids
        (B) TYPE: amino acid
        (C) STRANDEDNESS: single
        (D) TOPOLOGY: linear (ii) MOLECULE TYPE: protein (vi) ORIGINAL SOURCE:
        (A) ORGANISM: Ehrlichia (xi) SEQUENCE DESCRIPTION: SEQ ID NO:37:

```
Leu Ile Arg Ala Val Val Leu Val Leu Ser Glu Ile Pro Val Leu Asn
1               5                   10                  15

Ala Glu Ile Ser Gly Asp Asp Ile Val Tyr Arg Asp Tyr Cys Asn Ile
            20                  25                  30

Gly Val Ala Val Gly Thr Asp Lys Gly Leu Val Val Pro Val Ile Arg
        35                  40                  45

Arg Ala Glu Thr Met Ser Leu Ala Glu Met Glu Gln Ala Leu Val Asp
    50                  55                  60

Leu Ser Thr Lys Ala Arg Ser Gly Lys Leu Ser Val Ser Asp Met Ser
65                  70                  75                  80

Gly Ala Thr Phe Thr Ile Thr Asn Gly Gly Val Tyr Gly Ser Leu Leu
                85                  90                  95

Ser Thr Pro Ile Ile Asn Pro Pro Gln Ser Gly Ile Leu Gly Met His
            100                 105                 110

Ala Ile Gln Gln Arg Pro Val Ala Val Asp Gly Lys Val Glu Ile Arg
        115                 120                 125

Pro Met Met Tyr Leu Ala Leu Ser Tyr Asp His Arg Ile Val Asp Gly
    130                 135                 140

Gln Gly Ala Val Thr Phe Leu Val Arg Val Lys Gln Tyr Ile Glu Asp
145                 150                 155                 160

Pro Asn Arg Leu Ala Leu Gly Ile
                165
```

(2) INFORMATION FOR SEQ ID NO:38:

(i) SEQUENCE CHARACTERISTICS:
        (A) LENGTH: 177 amino acids
        (B) TYPE: amino acid
        (C) STRANDEDNESS: single
        (D) TOPOLOGY: linear (ii) MOLECULE TYPE: protein (vi) ORIGINAL SOURCE:
        (A) ORGANISM: Ehrlichia (xi) SEQUENCE DESCRIPTION: SEQ ID NO:38:

```
Gly Val Phe Met Gly Arg Gly Thr Ile Thr Ile His Ser Lys Glu Asp
1               5                   10                  15
```

```
Phe Ala Cys Met Arg Arg Ala Gly Met Leu Ala Ala Lys Val Leu Asp
            20                  25                  30

Phe Ile Thr Pro His Val Val Pro Gly Val Thr Thr Asn Ala Leu Asn
        35                  40                  45

Asp Leu Cys His Asp Phe Ile Ile Ser Ala Gly Ala Ile Pro Ala Pro
    50                  55                  60

Leu Gly Tyr Arg Gly Tyr Pro Lys Ser Ile Cys Thr Ser Lys Asn Phe
65                  70                  75                  80

Val Val Cys His Gly Ile Pro Asp Asp Ile Ala Leu Lys Asn Gly Asp
                85                  90                  95

Ile Val Asn Ile Asp Val Thr Val Ile Leu Asp Gly Trp His Gly Asp
            100                 105                 110

Thr Asn Arg Met Tyr Trp Val Gly Asp Asn Val Ser Ile Lys Ala Lys
        115                 120                 125

Arg Ile Cys Glu Ala Ser Tyr Lys Ala Leu Met Ala Ala Ile Gly Val
    130                 135                 140

Ile Gln Pro Gly Lys Lys Leu Asn Ser Ile Gly Leu Ala Ile Glu Glu
145                 150                 155                 160

Glu Ile Arg Gly Tyr Gly Tyr Ser Ile Val Arg Asp Tyr Cys Gly His
                165                 170                 175

Gly
```

(2) INFORMATION FOR SEQ ID NO:39:

(i) SEQUENCE CHARACTERISTICS:
        (A) LENGTH: 2129 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:39:

```
TTTACCTCTT TTTGAAGAAA TCTTAAAGAA AAAGCATGGG GCACGGTCCA ACACATCGAA      60

CCTTCCCCAT ACTTTTCACG AGAAAGATAT CCTAATAACT TAGAACATCT TCATCGTCAG     120

GATCCTTTAA CGGCAAAGCA GTCGGAACAT CTACTAACTC TTGCTGCATA CCAGCATCAG     180

CTTCTACAGA TACTTCAACC TTCTCAACTT CTTCAGTTGC TTGTGTCTCT TGATCAGAGA     240

TTCCTGCTTC TTGCTGCATA CCAGCATCAG CTTCTACAGA TACTTCAGAC TTCAGATCAC     300

CTTCAGTAAC ACCAAGAACT GTAGACTCAG GTTGTACTGG CGCAGAAACT TCAGGAGCTG     360

ATTCTAGTTG TTGCGCTTCT GGAGCAACTA CCACTTCTTG AAGCTTATTT TCTTCTAGTG     420

ATGGTACAAT CGCTTCTGCA GCTTCAACAC CAGGTAATTC TGCTTCAGCT ACTACAGGTA     480

CTTGCGCTAC AGGTTGCTCA AGATCTATCA AGTACCTTC TTCTAGAATA ACTTCTGGCT      540

CTTCCGTTTT TGTTTCTACA GATACTTCAA CCTTTTCAAC TTCTTCAGTT GCTTGTGTCT     600

CTTGATCAGA GATTCCTGCT TCTTGCTGCA TACCAGCATC AGCTTCTACA GATACTTCAG     660

ACTTCAGATC ACCTTCAGTA ACACCAAGAA CTGTAGACTC AGGTTGTGCT GGTGCAGAAA     720

CTTCAGGAGC TGATTCTAGT TGTTGCGCTT CTGGAGCAAC TACCACTTCT TGAAGCTTAT     780

TTTCTTCTAG TGATGGTACA ATCGCTTCTG CAGCTTCAAC ACCAGGTAAT TCTGCTTCAG     840

CTACTACAGG TACTTGTGCT ACAGGTTGCT CAAGATCTAT CAAAGTATCT TCCTTTAGAA     900

GAACTTCTGT TTCTTCTTTT ACTTCTACAG GAGCTTCAGT TCCCTCTAGT GCTTCTGCAA     960

TTTCTTGCTC TTGTTGACCA GAGATTACTT CTTTTTGCGC TACATCAGCA TTAGCTTCTA    1020
```

```
CAGATACTTC AGACTTTAGA TCACCTTCAG CAACACCAAG AACTGTAGAC TCAGGTTGTG    1080

CTGGCGCAGA AACTTCAGGA GCTGATTCTA GTTGTTGCGC TTCTGGAGCA ACTACCACTT    1140

CTTGAAGCTT ATTTTCTTCT AGTGATGGTA CAATCGCTTC TGCAGCTTCA ACACCAGGTA    1200

ATTCTGCTTC AGCTACTACA GGTACTTGCG CTACAGGTTG CTCAAGATCT ATCAAAGTAC    1260

CTTCTTCCAG AATAACTTCT TGCTCTTCTG TCTCAACTTC TTCAATTGCT GGTGCTTCTT    1320

GATCTATTTC TTGTTCTTCT TGCGTATCTA CACCCGACCC TGTTGCTGAC TCAACTACAC    1380

TAGGATCTAC TGTTTGAGGT TCCTCTGCTG CACTCTTTTC TATCTTGAAA AACCTTACGA    1440

CCGCTTTTTC TGGTGCGTTT ATCAAGTACA TACCTGTACC CTCTTCCTCT TGCACCAGCG    1500

ATAATGCCTC CACAACGGTA GTATAAACAC CACCTTCAGC AGTAGCAGCT CTGCCCGCTT    1560

CTGCCTCTAT AAAATACACC TTCCCTGGCA AATTACCATG ATGCATACCC GAAGCAACAT    1620

CTCTACATGC CACATGCTCA TCACCAACAT ATAAAACCAG TTCGCTCGGT CTCCACGTTC    1680

CCCGTACTAC CCTACACTTG TCATACGAGT ACGCATTAGT GCTGGCATCT TTGTCACAAG    1740

CACATCCTTC GTAGTAGCCA TCATCTCCAC TGGAAATGGT TTCACTACCA ATTCTGTAAT    1800

CACTTAGCTC TATATCTATA CCATACATAT ACGCAAATCC TCCTTTAATC CCTCTACGTT    1860

CACCAGCATT TGTTTAAGTG CTACACGATA CACCTAAAGA GATGATATCT TGCACACCTA    1920

TACATACAAT ATGCATATTT TACAACAACT TGCACAAATA TCCGACCAAC TAAGCACAAA    1980

TAAGGACGAT GATAACAAGT ATGCGAAGAA ATCCCCTAAA CCATATTGCC TACTATCCTC    2040

TAAAATACTA TCAAGCTTTA TCATGAGTGC TTTAGTTGCA AATTAGCAAA TTGTTCAACG    2100

AAATCTAGCA ATGCTGTTTC CTCGTGCCG                                     2129

(2) INFORMATION FOR SEQ ID NO:40:

(i) SEQUENCE CHARACTERISTICS:
        (A) LENGTH: 1919 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:40:

ATGCTGTGAA AATTACTAAC TCCACTATCG ATGGGAAGGT TTGTAATGGT AGTAGAGAGA      60

AGGGGAATAG TGCTGGGAAC AACAACAGTG CTGTGGCTAC CTACGCGCAG ACTCACACAG     120

CGAATACATC AACGTCACAG TGTAGCGGTC TAGGGACCAC TGTTGTCAAA CAAGGTTATG     180

GAAGTTTGAA TAAGTTTGTT AGCCTGACGG GGGTTGGTGA AGGTAAAAAT TGGCCTACAG     240

GTAAGATACA CGACGGTAGT AGTGGTGTCA AAGATGGTGA ACAGAACGGG AATGCCAAAG     300

CCGTAGCTAA AGACCTAGTA GATCTTAATC GTGACGAAAA AACCATAGTA GCAGGATTAC     360

TAGCTAAAAC TATTGAAGGG GGTGAAGTTG TTGAGATCAG GGCGGTTTCT TCTACTTCTG     420

TGATGGTTAA TGCTTGTTAT GATCTTCTTA GTGAAGGTTT AGGCGTTGTT CCTTACGCTT     480

GTGTCGGTCT CGGAGGTAAC TTCGTGGGCG TTGTTGATGG GCATATCACT CCTAAGCTTG     540

CTTATAGATT AAAGGCTGGC TTGAGTTATC AGCTCTCTCC TGAAATCTCT GCTTTTGCTG     600

GGGGTTTCTA CCATCGTGTT GTGGGAGATG GTGTTTATGA TGATCTGCCA GCTCAACGTC     660

TTGTAGATGA TACTAGTCCG GCGGGCCGTA CTAAGGATAC TGCTGTTGCT AACTTCTCCA     720

TGGCTTATGT CGGTGGGGAA TTTGGTGTTA GGTTTGCTTT TTAAGGTGGT TTGTTGGAAG     780

CGGGGTAAGT CAAACTTACC CCGCTTCTAT TAGGGAGTTA GTATATGAGA TCTAGAAGTA     840
```

-continued

```
AGCTATTATT AGGAAGCGTA ATGATGTCGA TGGCTATAGT CATGGCTGGG AATGATGTCA    900

GGGCTCATGA TGACGTTAGC GCTTTGGAGA CTGGTGGTGC GGGATATTTC TATGTTGGTT    960

TGGATTACAG TCCAGCGTTT AGCAAGATAA GAGATTTTAG TATAAGGGAG AGTAACGGAG   1020

AGACTAAGGC AGTATATCCA TACTTAAAGG ATGGAAAGAG TGTAAAGCTA GAGTCACACA   1080

AGTTTGACTG GAACACTCCT GATCCTCGGA TTGGGTTTAA GGACAACATG CTTGTAGCTA   1140

TGGAAGGCAG TGTTGGTTAT GGTATTGGTG GTGCCAGGGT TGAGCTTGAG ATTGGTTACG   1200

AGCGCTTCAA GACCAAGGGT ATTAGAGATA GTGGTAGTAA GGAAGATGAA GCTGATACAG   1260

TATATCTACT AGCTAAGGAG TTAGCTTATG ATGTTGTTAC TGGACAGACT GATAACCTTG   1320

CTGCTGCTCT TGCCAAGACC TCTGGAAAAG ATATCGTTCA GTTTGCCAAT GCTGTTAAAA   1380

TTACTAACTC CGCTATCGAT GGGAAGATTT GTAATAGGGG TAAGGCTAGT GGCGGCAGCA   1440

AAGGCCTGTC TAGTAGCAAA GCAGGTTCAT GTGATAGCAT AGATAAGCAG AGTGGAAGCT   1500

TGGAACAGAG TTTAACAGCG GCTTTAGGTG ATAAAGGTGC TGAAAAGTGG CCTAAAATTA   1560

ATAATGGCAC TAGCGACACG ACACTGAATG GAAACGACAC TAGTAGTACA CCGTACACTA   1620

AAGATGCCTC TGCTACTGTA GCTAAAGACC TCGTAGCTCT TAATCATGAC GAAAAAACCA   1680

TAGTAGCAGG GTTACTAGCT AAAACTATTG AAGGGGGTGA GGTTGTTGAG ATTAGGGCGG   1740

TTTCTTCTAC TTCTGTAATG GTCAATGCTT GTTATGATCT TCTTAGTGAA GGTCTAGGCG   1800

TTGTTCCTTA CGCTTGTGTC GGTCTTGGAG GTAACTTCGT GGGCGTTGTT GATGGGCATA   1860

TCACTCCTAA GCTTGCTTAT AGATTAAAGG CTGGCTTGAG TTATCAGCTC TCTCCTGAA    1919
```

(2) INFORMATION FOR SEQ ID NO:41:

(i) SEQUENCE CHARACTERISTICS:
  (A) LENGTH: 3073 base pairs
  (B) TYPE: nucleic acid
  (C) STRANDEDNESS: single
  (D) TOPOLOGY: linear (ii) MOLECULE TYPE: DNA (genomic)

(xi) SEQUENCE DESCRIPTION: SEQ ID NO:41:

```
TCCCATGTCC GCAGTAATCT CTAACAATGG AGTATCCATA ACCTCTGATT TCTTCCTCTA     60

TAGCTAACCC TATGCTATTG AGCTTCTTAC CTGGCTGTAT TACACCAATC GCCGCCATCA    120

ATGCCTTATA ACTTGCCTCA CAAATGCGCT TAGCCTTAAT AGAGACGTTA TCACCAACCC    180

AATACATCCT ATTAGTATCC CCGTGCCAAC CATCGAGGAT CACAGTAACG TCTATGTTAA    240

CTATATCGCC GTTTTTTAAT GCAATATCAT CTGGAATGCC ATGGCAAACC ACAAAATTCT    300

TCGAAGTACA AATAGACTTA GGATACCCTC TATAGCCCAA AGGCGCTGGA ATAGCCCCGG    360

CAGAAATGAT GAAATCGTGA CATAGATCAT TCAGAGCATT AGTAGTCACA CCAGGAACAA    420

CATGCGGCGT TATAAAATCA AGCACCTTAG CTGCAAGCAT CCCAGCCCTT CTCATACAGG    480

CAAAATCCTC TTTGGAGTGG ATGGTTATTG TACCCCGCCC CATAAAAACC CCCTAAATTC    540

CTAGAGCCAA TCTGTTAGGA TCTTCTATGT ACTGCTTCAC TCTTACCAAA AACGTCACAG    600

CACCTTGCCC GTCAACTATT CTATGATCAT ATGATAGCGC CAAATACATC ATAGGCCTTA    660

TCTCTACCTT ACCATCTACT GCCACAGGAC GCTGCTGTAT AGCATGCATA CCCAAGATTC    720

CAGATTGAGG AGGGTTGATT ATAGGGGTAG ACAATAGCGA CCCATACACA CCACCATTGG    780

TAATAGTAAA GGTTGCACCA GACATATCAG AAACAGAGAG CTTGCCACTT CTTGCTTTTG    840

TACTTAAGTC AACAAGTGCT TGCTCCATTT CAGCAAGTGA CATAGTTTCC GCTCTTCTGA    900
```

```
TAACAGGCAC CACTAACCCC TTATCGGTAC CTACCGCGAC TCCAATGTTA CAATAGTCCC     960

TGTAGACTAT ATCATCGCCT GAAATCTCCG CATTCAGCAC AGGAATTTCG GAAAGGACTA    1020

GCACAACCGC TCTGATAAAG AAGGACATAA ACCCAAGCTT AACATCATAC CTCTTCACAA    1080

AGGCATCTTT GTACTTAGCT CTGAGCTCCA TCACTTTGCT CATATCAACT TCATTAAAGG    1140

TGCTGAGTGT AGCAGAGGTA TTTTGTGACT CCTTAAGCCT AGCAGCTATA ACTTGGCGGA    1200

TTTTGCTCAT CTTCACGCGT CTTTCACCCA CCACGTCGCC ATGGCAACTC ATCAGATCCT    1260

TAGACGGCTG GCTAGCAACT ATCTTCTTGT CTTGTTCACT CTTAGCACTC ATACCCAAAG    1320

CTCTAGAAGT AGGAGTTGTG TTGATTCCTG CAACAAAATC TTCTACAGTA GGAGTTACTA    1380

GACCTTTGCC TTCAATAATT GTCTTTTCCT GCGGTTTTTG AGTGCTCACT GCCTGTGCAA    1440

CAACGGGTTG AGCAAGCACC TCCTCCTTGC TCTCTGGCTC CTTATTAACA CCCTCTGCAG    1500

TAGCCTCACC CTGTGGCCGT ATGATAGCCA AGACCTGCCC TTGGTAATCA CTTCTTCATC    1560

TGCAACTCTC AACTCTGTGA GAACACCAGC AACAGGGCT GATATTTCAA GAGAAGTCTT     1620

GTCTGTTTCA ACAATGAAGA GCACATCTTC TGCAGATACA GTATCTCCCA CCTTTTTCAT    1680

TACCCGAATC GGAGCTTCTA GAATGGATTC GCCACCAAGA TTCTCAGCCC TAACTTCTAC    1740

AGCATCACCC ATAAATACAA ACCAGAACTA AAACAAAAAA CACAGATTGA AAGGCAGTGT    1800

AATCACCAAA AGACACTAAT GTCAAACCAT AGATGAATAC CTTGTTATAA GTATCCACGC    1860

GATAACGCTA TGTAATTTTC AGCAGATTTT TGTAGGTATA AAATCTCCTC TTCAGTCATC    1920

ATACGTAGAA ATTTTGCAGG CCTACCTGCC CATAACTCTC CAGATTTTAC AATCTTACCC    1980

CTAGTGAGCA GTGAACCTGC AGCTAACATG CTGCCCTCTT CCATCACTGC ACGATCCATA    2040

ACGATTGATC CCATACCCAC AAAGGCGTTA TTCCCAAGAG TACAAGCATG CAATATGCAG    2100

CTATGGCCAA TAGTAACGAA TTTACCTATT ACAGTATCAC CATGCATGCT ATCTGTATGT    2160

ACTACTGTAT TATCTTGAAT GTTTGTACCT TCACCCACTT CAATTTTATC CACATCGCCC    2220

CTGAGTACGG TTCCATACCA TATGCTGGCA TTCTTACCTA TACAAACATC TCCTATGATA    2280

CGGGCATAAC CTGCGATAAA TGCAGTGCTA TCTACAGACG GTGATACTCC TGCATAAGGC    2340

ACCAGAACTT CCCTCATAAC TTCACAACCT CCAGTGTTCT TTAAACGGCA CAGCATGATA    2400

GTGTTTTTAG CACACCATAA CGGAGTACAC CACCACTCTT AACAGATTTG GCTCTGGCAC    2460

ACTAGATGCA CACATATCTT GTATAGGACT TATATATTGT TGTTCATGAA ACGTGCGTAA    2520

TGCTATGGGA GATTACTATT CTTATGTATG TAAATTAAGC AAATTTAGCA CGTGCTACTG    2580

CACCCAGCAT GTTCTCATTT TCTTTAAAAG GCAGACCTTC CTTTTTCGAA ATAGCCTTTT    2640

CTTTAGGAAG CGTAATGATG TCTATGGCTA TAGTCATGGC TGGGAATGAT GTCAGGGCTC    2700

ATGATGACGT TAGCGCTTTG GAGACTGGTG GTGCGGGATA TTTCTATGTT GGTTTGGATT    2760

ACAGTCCAGC GTTTAGCAAG ATAAGAGATT TTAGTATAAG GGAGAGTAAC GGAGAGACTA    2820

AGGCAGTATA TCCATACTTA AAGGATGGAA AGAGTGTAAA GCTAGAGTCT AACAAGTTTG    2880

ACTGGAACAC TCCTGATCCT CGGATTGGGT TTAAGGACAA CATGCTTGTA GCTATGGAAG    2940

GCAGTGTTGG TTATGGTATT GGTGGTGCCA GGGTTGAGCT TGAGATTGGT TACGAGCGCT    3000

TCAAGACCAA GGGTATTAGA GATAGTGGTA GTAAGGAAGA TGAAGCTGAT ACAGTATATC    3060

TACTAGCTAA GGA                                                      3073
```

(2) INFORMATION FOR SEQ ID NO:42:

(i) SEQUENCE CHARACTERISTICS:
        (A) LENGTH: 3786 base pairs (B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:42:

| | | | | | |
|---|---|---|---|---|---|
| AAAAGCTTAA | GGAAGATGTG | GCTTCTATGT | CGGATGAGGC | TTTGCTGAAG | TTTGCCAATA | 60 |
| GGCTCAGAAG | AGGTGTTCCT | ATGGCTGCTC | CGGTGTTTGA | GGGTCCGAAG | GATGCGCAGA | 120 |
| TTTCCCGGCT | TTTGGAATTA | GCGGATGTTG | ATCCGTCTGG | GCAGGTGGAT | CTTTATGATG | 180 |
| GGCGTTCAGG | GCAGAAGTTT | GATCGCAAGG | TAACTGTTGG | ATACATTTAC | ATGTTGAAGC | 240 |
| TCCATCACTT | GGTGGATGAC | AAGATACATG | CTAGGTCTGT | TGGTCCGTAT | GGTCTGGTTA | 300 |
| CTCAGCAACC | TCTTGGAGGA | AAGTCGCACT | TGGTGGGCA | GAGATTTGGG | GAAATGGAAT | 360 |
| GCTGGGCATT | GCAGGCCTAT | GGTGCTGCTT | ATACTTTGCA | GGAAATGCTA | ACTGTCAAAT | 420 |
| CTGACGATAT | CGTAGGTAGG | GTAACAATCT | ATGAATCCAT | AATTAAGGGG | GATAGCAACT | 480 |
| TCGAGTGTGG | TATTCCTGAG | TCGTTTAATG | TCATGGTCAA | GGAGTTACGC | TCGCTGTGCC | 540 |
| TTGATGTTGT | TCTAAAGCAG | GATAAAGAGT | TTACTAGTAG | CAAGGTGGAG | TAGGGATTTA | 600 |
| CAATTATGAA | GACGTTGGAT | TTGTATGGCT | ATACCAGTAG | AGCACAGTCG | TTCGATAACA | 660 |
| TTTGCATATC | CATATCTAGT | CCACAAAGTA | TAAGGGCTAT | GTCCTATGGA | GAAATCAAGG | 720 |
| ATATCTCTAC | TACTATCTAT | CGTACCTTTA | AGGTGGAGAA | GGGGGGGCTA | TTCTGTCCTA | 780 |
| AGATCTTTGG | TCCGGTTAAT | GATGACGAGT | GTCTTTGTGG | TAAGTATAGG | AAAAAGCGCT | 840 |
| ACAGGGGCAT | TGTCTGTGAG | AAATGCGGAG | TGGAGGTAAC | TTCTTCTAAA | GTTAGAAGAG | 900 |
| AGAGAATGGG | GCACATAGAG | TTGGTCTCAC | CTGTTGCTCA | TATTTGGTTT | CTTAAATCCC | 960 |
| TGCCGTCACG | TATAGGTGCT | CTGCTAGACA | TGCCTTTAAA | GGCTATAGAG | AATATACTAT | 1020 |
| ATAGTGGAGA | TTTTGTAGTA | ATTGATCCGG | TAGCTACTCC | TTTTGCTAAG | GGGGAAGTAA | 1080 |
| TCAGTGAGGT | AGTTTATAAT | CAGGCGCGGG | ATGCCTATGG | TGAGGATGGA | TTTTTTGCGC | 1140 |
| TCACTGGTGT | TGAAGCTATA | AAGGAGTTGC | TAACTCGCCT | TGATTTGGAG | GCTATCAGGG | 1200 |
| CTACTTTGAG | GAATGAGCTT | GAGTCAACTT | CTTCGGAAAT | GAAGCGTAAG | AAGGTTGTTA | 1260 |
| AGAGGCTCAG | GCTTGTTGAG | AATTTTATTA | AGTCTGGTAA | TAGGCCGGAG | TGGATGATCT | 1320 |
| TGACTGTAAT | TCCTGTTCTT | CCACCGGATT | TGAGGCCGTT | GGTATCACTG | GAAAATGGTA | 1380 |
| GACCTGCGGT | ATCAGATTTA | AATCACCATT | ACAGGACTAT | AATAAACCGT | AATAACAGAT | 1440 |
| TGGAAAAGCT | ACTCAAGCTG | AATCCTCCTG | CGATCATGAT | ACGCAATGAA | AAGAGGATGT | 1500 |
| TGCAAGAAGC | GGTAGATGCT | CTGTTTGACA | GCAGTCGGCG | TAGTTACGTT | TCCAGTAGAG | 1560 |
| TTGGAAGCAT | GGGCTATAAG | AAGTCTCTTA | GCGACATGCT | AAAGGGTAAG | CAGGGTAGGT | 1620 |
| TTAGGCAGAA | CTTGCTTGGT | AAAAGGGTTG | ACTATTCTGG | TAGGTCAGTA | ATAGTTGTGG | 1680 |
| GCCCTAGTTT | GAAGCTGCAT | CAGTGTGGTT | TGCCCAAGAA | GATGGCTCTT | GAGCTGTTCA | 1740 |
| AGCCGTTCAT | TTGTTCTAAG | CTGAAGATGT | ACGGTATTGC | TCCGACTGTG | AAGTTGGCTA | 1800 |
| ACAAGATGAT | TCAGAGTGAG | AAGCCTGATG | TTTGGGATGT | TTTGGATGAA | GTGATTAAAG | 1860 |
| AGCATCCTAT | TCTCCTTAAT | AGGGCTCCTA | CACTGCATAG | ATTGGGTCTT | CAGGCGTTTG | 1920 |
| ATCCTGTATT | GATAGAAGGT | AAGGCAATAC | AGTTGCATCC | GTTGGTATGT | AGTGCGTTTA | 1980 |
| ATGCCGATTT | CGATGGTGAT | CAGATGGCGG | TACACGTGCC | ATTGTCTCAA | GAGGCGCAGC | 2040 |
| TTGAGGCGCG | CGTGTTGATG | ATGTCTACAA | ATAACATCTT | GAGTCCTTCT | AACGGTAGGC | 2100 |
| CAATTATAGT | TCCGTCTAAG | GATATCGTTC | TTGGGATATA | CTATTTAACG | TTGTTGGAAG | 2160 |

| | |
|---|---:|
| AAGATCCTGA AGTGCGTGAA GTGCAGACTT TTGCGGAGTT CAGCCACGTG GAGTACGCAT | 2220 |
| TGCATGAGGG GATTGTGCAT ACGTGCTCAA GGATAAAGTA CAGAATGCAG AAGAGTGCAG | 2280 |
| CTGATGGTAC TGTATCTAGC GAAATAGTTG AGACTACGCC TGGTAGGTTG ATATTGTGGC | 2340 |
| AGATATTCCC GCAGCATAAG GATTTGACTT TTGACTTGAT CAACCAAGTG CTTACGGTTA | 2400 |
| AGGAAATCAC CTCCATTGTG GATCTTGTCT ATAGAAGTTG TGGTCAGAGG GAGACGGTAG | 2460 |
| AGTTCTCTGA CAAACTGATG TATTGGGGAT TCAAGTATGC TTCGCAATCA GGTATTTCTT | 2520 |
| TTGGTTGTAA GGATATGATT ATTCCTGATA CTAAGGCTGC GCACGTTGAA GATGCTAGCG | 2580 |
| AAAAGATCAG GGAATTCTCT ATACAGTATC AGGATGGTTT GATAACCAAG AGCGAGCGCT | 2640 |
| ATAACAAAGT GGTTGATGAG TGGTCTAAGT GTACCGATTT GATTGCTAGG GATATGATGA | 2700 |
| AGGCTATATC TTTATGTGAT GAGCCAGCGC GTTCAGGCGC TCCTGATACG TAACCTTGTC | 2760 |
| GCCAAGTGCA ACTTTTCCTA AACTAAAGCC TCAAATCTTT ATTATATTCT GTTAATGACT | 2820 |
| CAGTGGACTT TTGGCAGAAA GAGCTAGTTT CCTTTGGTAC AAACACTTTT ATAGAGGGTT | 2880 |
| CTGATTAATC TATCCGATGG TCTAAAATCA AAATAACATA TGCAATCGTT GGCTGAAAAA | 2940 |
| GCTCACCCGT GGTGTTATAA CAATAATTCC TCTCCTTGTT TTCATATATA ACCTTTTGGA | 3000 |
| AACATTCCTG TTGGAGCCAA AATTTCTATA TTTTGGAAAC TTGGCATATG GATGGATGAT | 3060 |
| GGCTGAAGTA TGCCATTTAT TTTCCTTTTG GGGAGGACTA GAGAAAGCAG AATAGTTGTT | 3120 |
| ACACTACTTT TGAAAGTAAA GTTTGTAGGA CAACCCAGTT TAATGTGGAA TAAAGCCCTG | 3180 |
| TTCTTTAGTT TTCATGTCAT AACACATATT CATTTCTAAA CATTTTTCCT GACCACCCAA | 3240 |
| TTTAAAGTAG TTGACATCCC CAGAAGTCAC TTTCTCTAAC AGAGGTCAAC ACACTTTTCT | 3300 |
| GTGTACTGCC AGACAGTAAA CATTTTGGAC TTTGTATGTT ATATGGTCTC TTTCTGTTGC | 3360 |
| AACTACTGAA CTCTTCCATT GTAGCACGAA GGCGGCTGCA GACAATATGT AAACAGATGA | 3420 |
| GCATGACTCT GATCCATTAC AGCTCTATTT ATGGACACTG AAATTTAAAT TTGCTAAAAT | 3480 |
| TTTCACATCA CAAAATATTA TCCTACTTTT GATATTTTTC TAACACTTAA AAAATGTAAA | 3540 |
| AAACAATTCC TAACTCACAG ACCAAACACA ACCAGGCAGT AGACAGAATT TGACCAGTGA | 3600 |
| GCTATCATTT GAGACCCTCA GTTCCACATT ACTTTTAGAG AGGTTTTTTA AATGTCACTT | 3660 |
| CTTAGCATCT AAACAAATCT ATTTACATAT TTATATTACT TCTATAGTGT CATGTGCTAA | 3720 |
| AATTTAAGCT CTTGTATTAG TCCGTTCTCA CACTGCTATA AAGACATACC TGAGACTGGG | 3780 |
| TTTCAC | 3786 |

(2) INFORMATION FOR SEQ ID NO:43:

(i) SEQUENCE CHARACTERISTICS:
        (A) LENGTH: 3735 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:43:

| | |
|---|---:|
| AATGCGCTCC ACATAACTAG CATAACGTTT TCAGCAACGG CAGATCTTCA TATATAAGCA | 60 |
| CTGAACACCT ACGTTCCAAG ATCATGCTCT TCGCGCCTGT TTACTTGGTG GCTCAGAGTC | 120 |
| ATCATCACTA GGAGTTCGTG GTCTGTGAGA GCTAACTTGT GCTTCTTCCA GCGTATAACT | 180 |
| AGCACCTCCC AATCCTGATG CTGAAGGTTG ATCCCACGAA TAAGGCATAA TCCCTTGATC | 240 |
| CTGAGGTGGC ACATAGGGAG CTTGTGATCT TCCCATTCCA GTACTAGTAC CTCCTAGCCC | 300 |

```
AGATGTTGAG AATTGGCTAG ATGGATAAGG AACATTCTCT AGGACACGTA GTATAATATG    360

AGGGGGGGGG GGAACGAGTT GAGCTCCCTG TCCGGCAGTA CCTCCCAATC CTGATGTTGA    420

GGGTTGATCC CATGATGTTG AGGGTTGATC CCACGATGTT GAAGGTTGTG CATACGAATA    480

GGGCATCATC CCTGGATCAT GTGGTGGAAT ATGCGAAGCT TGTTGACTTC CCATTCCAGC    540

GGCACTTCCT AACCCTGATG TTGAGGGTTG ATCCCACGAT GTTGAAGGTT GTGCATACGA    600

ATAGGGCATC ATCCCTGGAT CATGTGGTGG AATATGCGAA GCTTGTTGAC TTCCCATTCC    660

AGCGGCACTT CCTAACCCTG ATGTTGAGGG TTGATCCCAC GATGTTGAAG GTTGTGCATA    720

CGAATAGGGC ATCATCCCTG GATCATGTGG TGGAATATGC GAAGCTTGTT GACTTCCCGT    780

TCCAGCGGCA CTTCCTAACC CTGATGTTGA GGGTTGATCC CACAATGTTG AAGGTTGTGC    840

ATACGAATAG GCATCATCC CTGGATCATG TGGTGGAATA TGCGAAGCTT GTTGACTTCC    900

CGTTCCAGCA GTACCCCCA TTCCTGATGT TGAGGGTTGA TCCCACGGCG CACCATAGGG    960

TATGGGTATA CGCTCAAGAA CACGTAGTGG GACACTGATA GCTTGTGCTC CTTCCACTCC    1020

AGCACTAGTA CTCCCTAATC CTGATGTCGA GGGTTGACTA GGTGCAGCAC CGGTCTGCTC    1080

AACAGCATTG AAATATCTTC CGTATTTCTT GTCACAAATA TTCATCATTA CTGAAAGATA    1140

CCGCAATGCT GTATTGCGCC ACTTGACTTC TATCTGTGGA ATTAATAGCG CATCTTCCGT    1200

AATATGCTCA TTGATCTCCT CATAGACATG GCACATGTCT AAAAATGATT TGCGAGCCCT    1260

GTATGCCCCG AGCTCCCTTC TTCTGCTATA TAAAGCACAC AAAATCTGGA GACAATGCCC    1320

AATCCTACCT GCAACAACAT GATCTACATT ACCGGTGGAA GCGTATACTC TATACATCAA    1380

GAACAAACCA CCTACTGCAT GCACTAAAGC ACCACCCCGA TACCTTTCTC GCTTGAGTCG    1440

TAAATCAAAA CTGTGAACTC CTAAACCTTC AACATATGCC TCTAAATAGT AGAGAAAATT    1500

TGCCATCGCT CTTCTAGAGA GTCCTAGACG CAGGCGTGCA CTTTCATTAT TACGTACCAT    1560

CGCTTCACAT GCAGCTGCAC TAGTCTCAAT AGCATCAATA ACACTGTCCA AGCAAGCCTC    1620

TGTACGATGA CGGAAAAAAC GCGGTGTATT AGGCTCAACT AACTCAGCAA CCTTACTGCA    1680

AAGCTCTATG TTATGCCGCA CTACGCGCAA ATCGCCTTT ATATTCTCTG TTTCCTCAGA    1740

ATCCAAAGAA GAATTTAAGC ATCTACTTAA GGCTGAAAAT TTTACATAGC AGTATGCACT    1800

TAAAGCTGTC ACTGTATGAG ATGCACTACC ATCTCTACGC TCACTACTCA CTGCACCAGT    1860

AAACCTCGTG GCAATAGTTC TGGCACAGCA GTTCACTATA GCAATAACAT TCACTATGAT    1920

AGCACATGCC TTGCCTATTT GTAGGTGTGC CTTACGCTTA ATAAAGTCTT GATCCATGAA    1980

CAGCGGCACT TCTTTGTTGC ACTGCGCCGT GATGCAGTCC TGCAACGCGT CGTACAACCG    2040

ATTGATCAAA CTATACAACA CCCCCGGTTC TGCGCTTGAA GCACCTTCTG CAGCAGTTAT    2100

ACAGCTGTTA ATACTGTCTA TCTTATCAGC TGCCGCAAAC ACGACATCTA CACCCCGGAG    2160

CTTGACAAAC GTATCGCGCA ATTCCAGCAT ACATTGACGT ATAGCCTGCA GGCATGCAGC    2220

ATATGGCCTG GAATTAGTCA TTATTGAATT ACATACAGTT TCTTTATATT CCGCAGAAGA    2280

GCAACCACTG TAGGCATATC CAGACATAAC TGGAGTAGTG AATATACGAG GCATATGCAT    2340

CTAATTAACC ACTGGAACAA CTTCACACCT TGAAAGTGTA GCATACCGGT GTGACGCAGC    2400

TCAATATTAA AGATTATGCA CTTCGTGATC GTCTACTAGG AGGCTCAAGT TCATCATCAC    2460

TAGGAGTTTG TGATCTAGGA GAGACTACCT GTGCTCCTTC CAGCGTAGAA CTAGCACCTC    2520

CTAATCCTGA TGTTGAGGGT TGTGCATACG AATAATCTTG CAACGGACCA CAAGGTGCCT    2580

GAGCTTGCAG TGCTCCCTGT CCAGCAGGAT TACCTCCCAA TCCCGATGTT GAGGGTTGAC    2640
```

-continued

```
TAGGTGAAGA GGGCATATGC CCTGGATCAT GAGGTAGCGT ATAGGAAGCT TGTGATCCTC    2700

CTATTCCAGC CCCAGCACTT CCTAGTCTAG ATGTTGAGGG TTGACTAGGC GAACCCTCAG    2760

TCTGCCTAAT ATTATTGAAA TATCTCTCGT ACTTCTTTTC CCAAATACCA ATCATTGCCG    2820

AAAGATACCC CAACATAGCA CTACAGAACC CAACTTCTGT CTGGGGATTT AATAGTAGAC    2880

CTCGCGTAAC GCATTCCTGA ATCTCATCAT AGACAGTACA CATGTCCAAA TATAATTCTT    2940

GTGCCGTATA TTCTGAAGCT CCCGCTCTTC TGACCTTATA TTTATAGAGA GTAAGCAACA    3000

TTTGAAGACA ATGCTCAATT TTACTCGCAA CAACATGCCC TGTATTACCC GTGGAAGCAT    3060

ATACTCTGTG CATTGAGAAT AAACTACCAA TTGCATACAC TAAAGCTTGC ACATACTTGT    3120

CATGCCTGAA ACTTTTAAAA GCAACGCTCA GTCCTAAACT TTTATATGTC TTGAAATGGT    3180

GTAAAAAACC TGTTCTCGCT TTTTTAGCGA GAGCTAGGCG GTTCTTTGCA CTATCGTTAT    3240

CACTCACCAT CTCTTCGCAT TCAGCCGAGG TAGACCCAAC TGCATCAAGC ATACTGTTTA    3300

AGCAACTCAC CGTACGATCA CGGAAACAAT ATGGAATCTC CGGATCAACT AGCTCAGCAA    3360

CCTTATTACA AAGCTCTATG TTATGCCTCA CCACACGTAG AATAGCCTTT CTACGCTTAG    3420

TTTCCTCAGG ACCCGGAGAA TAATTTAAAC ATCTGCTTAA AGCTGAAAAT TTTGCATTTA    3480

CGTATGCACT TAAAGCCATG TTGGCATGAT ACGCACTATG CTCATCAGCC TCACCTATTG    3540

CACTGTCAGA CGCCTCGGTT AAGGTTGTGA CAAAGCAGCT TGCCATGGTA ATAGCATTCA    3600

CCAGGATAGC ACATACCTTA GCGATTTGTA GGTGTACTTC ACGCCTCGTG AAGTCTGGAT    3660

CCATGAACCG CGGCACTTCT TTGTTGCACT GCGCCGTGGC ACAGTCATGC AGCATATTAT    3720

ATGCACTATG GATTA                                                    3735
```

(2) INFORMATION FOR SEQ ID NO:44:

(i) SEQUENCE CHARACTERISTICS:
        (A) LENGTH: 2322 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:44:

```
AATGTATACA GTCTCAGATT CAGAATCTAT AACTTCTTTC GTTACTCCAC CAATGTTAAT      60

GGCGAATATC TCATCGACTA AGCGTTCAGG ATACTTGCTA TCATTGTCGG TAGAGCCATC     120

TGACTTTTTT ACCGTGACAT TCTTTTTAAA AGAAACTCCA TTTACAACGG ACAATTCAGT     180

GCCATTTTGT AGCTTCGAGC GCAACTCCAC AGCAAATTCA CGTATTTTCT TCATACGTAA     240

TGCACTCTTC CATTCTTCAG TAAGAATAGA CCTGCTTTCT TCAAGTGTCC TTGGTCTTGG     300

AGGCACTACT TCAGTAACAA GAACGCCGAA ATAAGCGTCA CCATTGCTAA CCAGATGAGA     360

CGGTTTTCCT ACGGCAGATG AAAACGCCAA AGTAGTAAAG GCGTTTATAC CAAGCTGCAA     420

CGGAAAGTCT TTCACTAAGT TGCCAGATTT ATCGAGCCCA TGCATATCAA AATTCGTCAA     480

AACACCACTG ATCCGCGCAC CAAACATATC CTTTAGTTCA TTCAGCAATG CCCCGCGGCT     540

GATCATATCG TTTGCTTTTT TCACATTGCT AACTAGCAAC TCACCTGCCT TTTGCCTTCT     600

AATATTTGAA GATATCTTCT CTTTCAGCTT TTCTAGGTCT TCCTTAGTGA TCTCATGCTT     660

CCTTATTACC TTCATGATAT GCCAGCCGAC AACGCTACGG AACATTTCAC TGACTTCTCC     720

TTCATTTAGT GCAAACACCA CATTTCGCAC ACCTACCGGA AGAACATCCT TAGAGATATT     780

ATTGAGTGCA ATATCCTCTA TGGTGTAGCC AGCATCACTA ACCAATTCCT CAAAAGACTT     840
```

```
ACCCTCTTGG TAAGCTTTGT AAGCTAGCTC AGCTTCATTT TTGTCTGTAA ATACTAAATT    900

TAGAACATCT CTTTGATCAT GTAGTTCACT GTTTTTAATC TCAACGTCTA CCTCTTGATC    960

CGAAACAATG ACATCAGCAA GCAAGTCGTC TTCTGCCATG ATTATATAAT CAGCACTGCG   1020

ATATTCAGGG AAATTTAGAG AATTCTTGTA CTGCTCCTCA AACAATTTTT GCAATTCATC   1080

ATCAGATATA TCACTTCCTG AAATGTCTAC GGCATCAGAA GATATTTCCA CTATGTCTGC   1140

CACACGATGC TGCAGCAATC CCAACACAAC ATCTTTTGCT AATGCATCAT AATAAGGAAT   1200

ATGTAATTCC GCCCTATTAG GGAATAAACA CTCCATTAGA ATAGTAGAAG GTAAAGCATT   1260

GCGAATTTTA TTCACATAGG ACGACTCAGT CATTCCGCTG TCAGCCAATA CGGCTTCATA   1320

TCTCTCCTGG TCGAAGACAC CATTAGCATC CTGAAATATT CTTATATTTT TGATCAGACT   1380

CCGTAAGCTA TTTGAGCCAA CACGTATGCC TAAGTCATGA GCAAACTTTT CAACGACCAT   1440

GTCGGCTATC ATGTTCTTGA GGACAACTTC CTTAATACCA AACTGATTAA TTTGAGCATC   1500

AGACAATTTG TGTTGTAACA TCTTCTCTAG TTCTGCCAAC TCGTTGCGGT ACATTATACG   1560

GTAATCCCGC AATGGTAGAC ATTTATTACC CAACATTGCA ACGCACTGTC CGTTGCCAGA   1620

ATTAGACAAC TTACCCATTG GTATCATGCT TCCAAAAGTG ACAAAAGCCA TGGCACCTAA   1680

AACCGTTGCC ATGACCACCC AAACATAAAT CTTCCTTGAT CGCATAACAG AACGCCCATA   1740

GCTGGTCAGA TTCCCGAAGG AATATAGTAA TCAGAAAAAA TCTGCAAGAC TTTTTCTAGT   1800

TGTTTATGGG CAATATTCTG AATTTTGCAT AGTAGCCATT ACGTAATGTA TGGATAGACC   1860

CGTATTAATT TGTTTCGGTA CGATATATGA AGTTCTAAAA AGCTATAGAA CCTTGCCATG   1920

CAAAGCTTAA GAGCCCTTAC CCATCCCATA TACATCCGTG TTAATGAAAG CACCATTCTG   1980

CTGCTTGTGC AGAATTCTAC ATAAGCATCT CGTGCCGCTC GTGCCGAATT CGGCACGAGG   2040

AATTAGATTT AATAGCAGAA GAGCAGAGGC ACTGTGGTGA CTGAAGCAGC AATTAAAGTA   2100

ATGTGGCCAC AGCTAAGTAA TATCAGCAGA CACTGAAGTG GGGGAAGGAA GGAACAGATT   2160

GTTACCTGGG CATGATCAAA TTTCTGGATT CAGAAAAGTG TGGATGAAAT CCTGGCTTTA   2220

TTATTGATCA GTGCTGTGTG ATACAGCACC TAGTCCTCAA ACTCTTTCTT CTTAAGCATC   2280

CACACTTGCA AAATGTGCAA CTTCCAATAT CCATCTCTAA GG                      2322
```

(2) INFORMATION FOR SEQ ID NO:45:

(i) SEQUENCE CHARACTERISTICS:
        (A) LENGTH: 2373 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:45:

```
GCAAATATTT TCTTGGTGC CGCCCTAAAA GCCTGAAAAA TTTAAAGAAA TGTTACTGCT     60

CTAGTCATTC ATAAAATGCA AATAGCCTAC AGAAGGAGTA TTTACTGCTA TAGGCTTGAA   120

AGTGCAATCG TTATTTACTA TTTTTTATAC ATATCGCAGT ACAGAGATTT TACGCGCTAC   180

GCCTGTGCAT CATAGCCGTA TTGCATCAAT AAATTGTCGT TGCTACGCGG GAAAGCTGCT   240

TAGCGCTTGA CCATTTTTCA TACACATTGT ACCATCATAG CGAGTGTGGT GCTCATGAGA   300

GTGCGTAGTG TTGCCGCCGG TTTCTCATGT TATAATCTTG CTGCCGTTTT GTGCAGAAGG   360

AGGAGTAGTC TCGTTTTTTT CCAAAAGACA ATGTGCTGGA GTGTCCCGGT GAGCCTCAAG   420

GTTCTTGTGG GATTTGTGTG GGCTGTTGTA TAAATACCAC GTTCGAAGCT GTCCTAGTGT   480
```

-continued

```
AATTCAGCAT ATGTTGAGGA AGTTGTTGCT ATGAGGTTGA TGGTATGGCG AAAAGATTCT      540

TAAACGACAC AGAAAAGAAA TTACTATCTC TGCTCAAGTC GGTAATGCAG CATTATAAGC      600

CTCGTACCGG TTTTGTCAGG GCTTTGCTAA GTGCCCTGCG TTCTATAAGT GTAGGGAATC      660

CGAGACAAAC AGCACATGAT CTATCTGTGT TGGTTACACA GGATTTCCTT GTCGAGGTTA      720

TTGGCTCTTT CAGTACGCAA GCTATCGCTC CTTCCTTCCT CAACATCATG GCCCTGGTAG      780

ATGAGGAGGC ATTAAATCAC TACGACCGCC CTGGGCGTGC TCCAATGTTT GCAGACATGT      840

TGAGGTATGC GCAAGAGCAA ATTCGTAGAG GTAATCTGCT TCAGCATAGA TGGAATGAGG      900

AGACATTTGC ATCTTTTGCG GATAGTTACC TCAGGAGAAG GCACGAGCGT GTCAGTGCGG      960

AGCATCTTCG CCAGGCGATG CAGATCTTGC ATGCACCGGC TAGTTATCGC GTCCTGTCTA     1020

CAAATTGGTT TTTGCTGCGT TTGATTGCTG CAGGGTACGT GAGGAATGCA GTTGATGTGG     1080

TCGATGCGGA AAGTGCAGGG CTTACTTCTC CTCGGAGCTC CAGTGAGCGT ACTGCTATTG     1140

AATCGCTCCT GAAGGATTAT GATGAAGAGG GTCTCAGCGA GATGCTCGAG ACCGAAAAAG     1200

GTGTCATGAC GAGCCTCTTC GGTACTGTGT TACTCTCGTG CCGAATTCGG CACGAGTTGA     1260

AAAGCAGCCT TTTTAAGGTA GACATCCTGT ATATGATTTA AGTCTCACCT CCCAATGGAA     1320

TCATGAAACA GTTAGAAAAA TAATGAACTA CGTCTTATAT AATCTTTATC GCTACTTTAA     1380

AAATGAGTAA TATATTCAGA TTTAGTAGAA ACATCCCTGA GGAACAATTT GTTTTCACAA     1440

ATTACATTGG TTCCTCACAT GCAAGATTAT TAAGCATTAA GGAGGAGGAT ATTGGACATT     1500

GTATACCCTG TAGGAATAGT TTTTTATTTT CAGAAATAAG CTCAGCTTAC TGATTGATGG     1560

CAAAGATAGT TGATGATAAA ATAGAAAAAA ACAAAGTTAC TCTTCTTAAT TTTGTACTCT     1620

TCTTACCTCC TTTCATTTTT AATTGGTTAT AAGTAGGTGA AAGTTAAAAC TTGGCAATGT     1680

TTGCTTTAGG AGTTATTACA ATTACTCAGG TTAGTAGTAT AGTTATACGG TCATCTTTAG     1740

TAAAACATCA TTCGGAGTCA TAGTCACACT TATGAATATC ACAGAATGGA TATGTGACTT     1800

TGGGGTTTTT TTGTGGGATA TTTTTTGAGA TATTTAAGGC AGAAGTGCCA CCTTTACTTC     1860

ATTTATTTTT ATCCGCCCCC CCCCCACCCC ACCGTTTCTC AGAAAGGATA AGGTTTTCAC     1920

AGTACCAGAG ACATTTATCT ACTAAAACTT TGAACTAATT AAAATATATA GGGCCGGGTG     1980

CAGTGGCTCA CGCCTGTAAT CCCAGCACTT TGGGAGGCCG AGGCGGGCGG ATCACGAGGT     2040

CCGGAGATGG AGACCATCCT GGCTAACACG GTGAAACCCC GTCTCTACTA AAACACAAA      2100

AAATTAGCCG GGCGAGGTGG CGGGCACCTG GGGTCCCAGC TACTGGGGAG GCTGAGGCAG     2160

AAGAATGGCG TGAACCCAGG AGGCGGATCT TGCAGTGAGC CAAGATCGCG CCACTGCACT     2220

CCAGCCTGGG CGACAGAACA AGACTCCATC TCAATAAATA AATAAATAAA TAAAATATTA     2280

TTTAATTTAA GAGAGTTGAA ATCATTGAAT TGATTCATTT AAACAAGGTA ATTTGCAATG     2340

GGTCTATTTT TAGGCTATTT TCTTTATAGT AGT                                  2373
```

(2) INFORMATION FOR SEQ ID NO:46:

(i) SEQUENCE CHARACTERISTICS:
        (A) LENGTH: 7091 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:46:

```
CCTATGGCAG CTCTAAACTC GGCACGACTG GTTTCTACAA GAGATTGGTC GACATTAAAC       60
```

-continued

```
CATGCGAAAT CATTGCGATC AATTCTTCCT TCTTTTTCCT GTATAGCACT ACAGACTTCC      120

TCTGCACTAG AAGCCACTCG TGTCCCGATG CGTACGTCAC GGATGCAAAG CCCCAGGTCT      180

TTTACGCTGC CGGGTGTGTC TATATCTTCC ACAACATAAT CAACGCAAGC GTGAATATGG      240

ATACCAGAAA CAGAGGTAAC CCTGTATACT AAATGCTCTT CCAAAACATG TTGATTAACA      300

GGTAAGCGCC TAGCACTATC ACCATTATCA GCAACAACGC CTTCATGCGC AACGTAATGA      360

GCAGCGAGCT CAACTGGCAG AGATGACCCA CTACTGTTAC TCAAGATACT AGATAAGAGT      420

ACCCGGAGAT TTTCTGTGTT TACACCAGTT TTCTCCACAA TATTTGCAGC ATGCTTCGGC      480

TGTGACCTTA AGATTTCACG TATTTCATCG GAGTGTTGTA TGAAAATACC ACAGTCCCCA      540

CGCACAGGTA CAGAGTGAGA TGCCCAGCGA TGGCGCTTCC CCAGATCTTC CCATAGCGAA      600

AGGCCGTGAG CTACTATTTC CTCAGCAAGA TTGAAAATGT GGCCTCCGGC AAAATCTGTA      660

TCTTTTGCAC TGCCAGCGAG GAAATCTCTA AGTGATATAC CGCCTCCAAG TGTAAGTACA      720

TTGCCAAATG TATTCACAGT TACCGCCACA TGACGGAGAA TAGTGGCGCA TGCATCGTGC      780

GCCTGAGAGG CCACAAAGGA CATGCAGACC CCCATTTTGG ATACAGCATC CCTGCCATGA      840

GAAACAGCGC CCTGCTGTAC TACACTAGAT TTATCGTATC CTACCAGACC AACAACGCCT      900

CGTACAACTA CTCGGAATAC ACCGCTCGCT TCTTGACTGA TTACTGTATT ACAAAAAGAA      960

AGCTCTAGGA CTTCTAGCGG CATACCGCTA ATAACGCTGT AAGCTCTTAG GATGCATTCA     1020

TCAATATCGC TTACATCGTA AAAAACCCTA CGAGCCATGT AACGTGGGTT ATGCCTCTGC     1080

AGATTACACG CGCTGTACAA TACATGAGTA GGCTTCTCAG GGACTCTCAC ATAGTGTTTT     1140

GCCAGAGCTT TGGGAATATT GTGCCAAGAA CATACAGATC CAGGCTCGCC TTGCCTAACG     1200

TCGCGGCAAT CTCTCTCAGT AAGCACGAGC TTTACTTTTT TCACAGCTGT ACGGTAAACA     1260

CCCTCCGCCT TTGTCGATGG AGCAATGTCA TACTCTACCC ACATCTTAAC TTTGGCTATG     1320

GGTACACCAC TGTTGTCCTG AATACTAAAT ATGCATGATT CGTGTACTGT CAGAGCACCG     1380

TTCTTGTAGC TACTAGGTGC TGAAGCCAAT AAAGAATGCA CCCTGGAGAA AGTAGTATAA     1440

CTCTGAACTT CAAATGTGGT AGAGTCCTCT TCTCTGACTA TTGTCATATC TTCAGACACC     1500

CCATCCAGGC ATCCAAGAAC AAAATTAGTT AAATCCTCTT CCTGGTTTTT TCCTGGCAAG     1560

CTGTTATAGG CAAGTGCAAG GGCATGCCAC AGCTGGAAAG GTACTTGTTG GAAGGCAGTA     1620

CTGTTACTCG CTGTCTTATG CAGAGCTCTT GCTAATAAAT CTGGGGAAGT TAGATTCTCA     1680

TGTATGAGTG CAGGAGGTAC CGCACTGCCC TCACGTAGAG TAAACCCCTC TGCTAAGAGT     1740

ATGACCATTC TGCGTCGTGC AGGATGACTG TTCCGATCAC GACATAAAAA GAAATCTATC     1800

GCGCTACCAA GCAGTGCAAC GGACGCTTTC GATGGGTTTT GCTTAAGCAG CAGAGTCATG     1860

GGTGCCTCAT CTTAGTTACT TCTAGTGACA AAGCGGTACT TTTATTCCTG TAAGGACAGA     1920

AAGGCCTGTT TTTTTCCAGA AATCTACGCC TTACATGTAT GGAAACCTGC GCATCCAGCT     1980

ATAGATATCG CAAGGCATAG TGTGCAGAAT ACGGAGCTGT AGCAGGCGCT CTTACCCCCC     2040

AGCAAAGTAC GCAAACCTAG CGACGACTCG TTCTCACACG TTGTGAACAT ACGTAGTAAC     2100

ACACCTTGAC GTACCTAGCC TACACCACTA GACATATAGT GTAAACAAA AAGTACCAGA     2160

TCCCCGTCTC AGGGGTTGTA AAAGTAGCAC ATTGGAAACG GACTGTTAAG TATTTATATT     2220

ACTACTTAGG TTCAGAATAA ACATTCGAAT TGTAATGCAC CATAGGTTAG TAATGCACTA     2280

TGAGTGAGAA ATTACGCGAA TTGGTACTGT GCGATGATCT TGAAATTTAC AGTTGTAGAC     2340

ACGGCGCATG CGGAAGATAT AACCTCTCAA ACCCTGCAGA GGTTTTACTA ATCATATGTT     2400

TTGTCTAATA CCTGCCCACA AAAAACATAT GAAAGCCTTC GTAGCTCAGG TCGGTTCTCT     2460
```

```
GGCTGTTTTC ATCTCTAGGT TTTAATTCCC AAGAATTCGA CTTTTCGCGC TACCTAAGCA    2520

TTTTTAATCA CCGTTGACTA TTAGAGACGA TATAATAAGC TACATTGATT ATCTGAAATA    2580

TGTGATCCTT CTAAAAATCT TTAGGTGCTT TAGAAGAAGT ACATATTACC CTCTATGGCA    2640

ACAACATTGA TAATTTAGGT GAAGTGTCAC AGCGTTTCAT TATGAAAAAA AGGGATACTT    2700

ATTTATGGGG AATGGCACCT TATGCAATAT GAGCCTTAGG GATTGCCACA GTGTTTTGGT    2760

TTCACAGCAT GAGTAAGGAC GTGGTTTTTT AGCAAGTATT TATTGTGCTA TGTGTGTAAA    2820

AAGTAACATA TGAAGATCGC TAAAGAATTC ACACTAGAAA TAAGTTGATA CCTGATGATG    2880

TAGTATAAAG GTTGAGCAAT AGTCTTTTTT TGACTGTAAA TCCCGCATGC AGCTTTATGT    2940

GTGTTTATCG CAAAAAGTGG GCGTTTGTTG CAATAAAAAT TGAAATGCCA ACTATTATTG    3000

CACATACCGT GCTCATACCC TTAATCTTGT AGATGCGCTG TAATCACAAT TCGCATGTGC    3060

AGCAAAACTG TAATAGATAG CTTAGCACAG GGACGAATAA TCCCTAGATT CTACGCTGCG    3120

GGCTAGTGCT TTTTTTAGCA TCTATACGGG AGTATCTTTG ATATGATAAA CACACAACAG    3180

CATGATGCTG TGCTTATATA GCATTGGTAT ATATTCTGCG ATGCGGACTA ATCAATGTTG    3240

TAATCAAGTA AAAAATGCTT TTTTGAACCG TATATTGTTC GTAAGGCATG TATTACTCAG    3300

TTGTCGTACT ACAAATTCCT CTTCCTCTAG AGCATGCAAG TATGAATACA GCTTATGTGT    3360

GCGATGCGTA GATTACTAAT GCATGATTAG TGTAGGGTAT GCTGTATTTT TTGCATGCGT    3420

TTTAGATATG TTACGCAACA CATGTTTTTC AAGGACGCTG TGGCTATCAC GGATATGATA    3480

GCCACAATGC GCTGCTCTTA GGTCAACTAG GATGGGCTGT GGGTTTATGC ATATTAAGCA    3540

GTGGCTCCTG CATTCAAAGC TATTCTTTGT TGTGGTTAAC AATCAAAAAT AGAGAGTAGT    3600

TTGTTTATAA GAAGATATGC AAAAAACCTT TTTATCCACA GTAAGCCCCA GGCGTATCGA    3660

TGCACAAGGA TCCACCATGG CTATGTCTTA AGGATGTACC CAGAATATGA TCGTATCTCA    3720

TTGGCTAAGC AGAGCGTCCT CCAGTTTCTG ATTCTACAGA TAGTACATCC TGTAATGAAG    3780

AAATGGATCC TTCATCAAGT GTCGTTGATG GAGCATCATC CGGACAGTAC TTTGTAGTAG    3840

TGCTCTCGGA GTTCAGATCA TCGCTTGTAC TTACATCATC ATATGACGAA GAAACATCAA    3900

TCGTAGCATG TTCGGGTTGA GGCTCTGCCA GATGCACTTC CTGAGAGAGG AGGTCATGAT    3960

ATAAATCCCA CAGATAGTGC TGTTTTTAAC CAGGTCCCTG AAAAACTCTT CTGGAGAAAC    4020

TGGCAGAGGA GCCATTGCGT ACTGCAGTTT GGTAATATTC ATGCCTATGC AAGGGATGCG    4080

TTGAACGCGA ACAAGTGTAG GATCTGGTAC GCGCGTATCT TGAGGAGTAA AGACTTTCCG    4140

TTTATAGAAC CGATGCTTCA ATCTGAGTAG AAGACGTCCT AACGGAGGAC ATACTCTAAA    4200

CAGTAATGGT GGTGAGGTCT TTATATTGCA GTCTGGTGGA GTGATGATTG TCAGGTTTAA    4260

TGAACAGTTA TCATAGAGAA CTCGTCCCTC TCCTTGTATA GAGATCTCGT ATTTCAGTGC    4320

TGTGTTTACT TTGAACGCAG GAGTCTTTTC TCCCTCTGTA GACTGCGGCA CTTTCAGGAG    4380

AAAGTCCAAA TTCTCGCAGA CTGCAATACG CTCTGGTGTT ATTGCATCTA CCTGTTTTAT    4440

ATTGCTACAC GCTGATACAT AGATGCGATT TAGTAGATTT AGCGTGGCAC CTGCATCGCT    4500

AAAGAAGTAT TCTTTATCCA AAGCATGTTT TATAGGCCAA ATTACATCGA AACATACCCA    4560

GGCTGACAGC CCTCCTTGAT GGCAATGGCT TGCTATTTCA TCAAGCAGTC TAATGTCTGG    4620

GACGACCCCA TGACGATCAT CTCGGAACAT TTTTTGCAGC ATGGCTATCG CGAGACTTCT    4680

TTCACGATAG CGGCGCAAAA ATACCCCTCT ACTTACTCCA TATGTTCTCT GACATACAAG    4740

ATTAAGGTTA GTGATGCTCG ACGATTTTAT GCTCCTTTCT AGTCTTGCAA TATGAGCACT    4800
```

-continued

```
TACATTTTGT CTAGGGTAAA ATGTTTTATT GATGCACCAG TCACATCTAT GCATATCGAT       4860

TAGAAACTGA TGGCCGTACA AGTTAGACTT GTTTTTATAC GAATCGCAAA GTGCGCTGTG       4920

GAAGGAAAAC CCCGATGCAC CTTCCAGCCA TTTTTTCTTT TGAGAATACT TTAAACTTAC       4980

ATCTATAGAA GGGCGATGAT CCTTATGCTT AGCTTTACTA TCCTTACTTG CGTCAGAGCT       5040

ATTGTGTGTG CAGATATGTA CTGAATTAGC CTCATCTTCT GCCTTAGAGA CAGCACTACT       5100

AGATGTTGAA AAAATTGAGA TTATCCTAAA AAACAGTGCT CTCAAATAGT TCAGGATACC       5160

ACTGACAGTT CTTCTAGATC CATTGTGAGT ATTCTTTTTA CGCAACTTAA ACCTCCATGT       5220

TACACAATAT GCAGCTTTGC TATTTTCCTT TCTCATGTGG ATGCGCTAAT CTGCGTTTGA       5280

TCAGTAGTAA CGACGCGCGC TGTAGTGTAG TTGTTCCAAC AATGAACATG CAAAATTGCT       5340

GCAATACTTA ACTTCCTCCT TCTGAAATGC ATTTCCCACA TTTCAGGCTT TTACTATTTC       5400

ATGCTTTACA TCGTGTAGCG CATTTTTGAA AAAACAAGAT ATTAGTACAG CATTTCTGGT       5460

AAACCAGTAA TTGTTCCTAT TCAAGGTCTC TGAATCATGA CGACCACTTT CTTTGCGGCA       5520

ATTGAGAAAT TCCTCACATA TTTGATATAC ACCGCACTTT TTGTTTTTGC TCCATGAATG       5580

GATTACCGGA TCCAAGGGCA TTGCTATACT TCACTGTGCA ACACTACTGT AAGTGTCGTT       5640

AGCATATCAT GAAATTATTA AATAATATGT AGAATATGTT GTGCAAAAGA CGCTTATAAC       5700

AACTTAATAG TGAATTTCAT GAAATTTGTG AGTAGTTTTC TATCGGAATA CGTGTTTTAG       5760

CAACGCTATA GATGGGGTAA GATCGCTTTT ATGTTCAGAA ATTCGCAACC ATACTATTTT       5820

CTCTGTATGC GAAGACATGT CTTAGCGTCA AGCCACATAT GTGGGGTACT TAAGCGTTGC       5880

CTTGCACGCA ACAGCTCCAC ATTGCCTGGA TTTTTCTTAA CATCAGCTAA TTATATACCA       5940

GACTCACAGA TATACTACGC GTAACCAGTC ATATTATGCA GCACCTGTAC ATGTTCTCTG       6000

GGGAGTTCCT TTATGAAACG AGACATTTTC ATGGATTGGC TCCAGTTATT GATTTCTCTC       6060

ATTGCAGCAC ATGATATGTA TAGCTGCTCT CTAGCTCTTG TTATGCCAAC ATAGGCTAAG       6120

CGCCTCTCTT CTTCCAGAGC GTTTCCAGTT ATGTCATTCA TGGATTTTTC GTGTGGGAAG       6180

ACTCCTTCCT CCCATCCGGG GAGGAAAACC AACGGGAACT CCAACCCCTT TGCGGCATGT       6240

AATGTCATAA CGTGTACGTA GTTATTGTCT TCTTCTAAAG AATCATTTTC TGCCACTAAG       6300

CTAATGTGTT CTAAAAACTT CGACACATCA TCGAATCCTG ATACGGCTGA GAAGAGTTCC       6360

TTTATGTTCT CTATTCTTGA TAGACCTGAT TCCCCGTCTT TTTTTAGAGA TTCTATATAT       6420

CCAGAGTCAT GAGCAATAGC TTTTAGTACA TTGACGGATG AATCTCTACT TAACATTTCT       6480

CTCCAATCAT CAAACTGCTT GAGAAGATCT TGCAGAATGT TGGATGTATT ATCAGATAGT       6540

AATCCATCTT TTATCATTGA GTGTCCGGCT TCAGTTAGGG AAATACTGTG CTTTCTCCCA       6600

TATGCACGAA GCTTATTGAC AGTAGAAGTT CCGAGCTTGC GTTTGGGCTT ATTTATAATT       6660

TTCTCAAACG CTATGTCGTT ATTGGGGTTG ACTACTACTT TGAGATATGC AACAAGATCG       6720

CGGATTTCTA CCCTATCATA GAACTTGGTT CCGCCGATAA TTTTGTAAGG TATACCATAT       6780

CTTACGAAGA ACTCCTCGAA GACTCTAGTC TGAAAGCTGG CTCTTACTAG AACAGCAGTT       6840

TCACTAAATT TATAATCGTA AGAGCTCTTA ATATGCTCAC TAATGTATTG AGCTTCGAGC       6900

CGTCCATCGA AGAACTTCAT TAAACCAACT TTTTGTCCTG CCTGATTGTG CGTCCATAAT       6960

GTTTTTTTAA GGCGGGATTT ATTATTATCA ATTATCGCTG ATGCTGAGGC TAATATGTTA       7020

GACGTTGACC TATAATTACA TTCCAGCCTT ATTACTTTAG CGTCTGGGAA ATCATCTGAA       7080

AATCTGAGTA T                                                           7091
```

(2) INFORMATION FOR SEQ ID NO:47:

(i) SEQUENCE CHARACTERISTICS:
        (A) LENGTH: 3947 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:47:

```
GGTATATCGA TAGCCTACGT AGTCACTCCT TATTATTAAA AAGGAAGACC AAGGGTATTA      60

GAGATAGTGG AAGTAAGGAA GATGAAGCAG ATACAGTATA TCTACTAGCT AAGGAGTTAG     120

CTTATGATGT TGTTACTGGG CAGACTGATA ACCTTGCCGC TGCTCTTGCC AAAACCTCCG     180

GTAAGGACTT TGTTAAATTT GCCAATGCTG TTGTTGGAAT TTCTCACCCC GATGTTAATA     240

AGAAGGTTTG TGCGACGAGG AAGGACAGTG GTGGTACTAG ATATGCGAAG TATGCTGCCA     300

CGACTAATAA GAGCAGCAAC CCTGAAACCT CACTGTGTGG AGACGAAGGT GGCTCGAGCG     360

GCACGAATAA TACACAAGAG TTTCTTAAGG AATTTGTAGC CAAAACCCTA GTAGAAAATG     420

AAAGTAAAAA CTGGCCTACT TCAAGCGGGA CTGGGTTGAA GACTAACGAC AACGCCAAAG     480

CCGTAGCCAC GGACCTAGTA GCGCTTAATC GTGACGAAAA AACCATAGTA GCTGGGCTAC     540

TAGCTAAAAC TATTGAAGGG GGTGAGGTTG TTGAAATAAG GGCAGTTTCT TCTACTTCTG     600

TGATGGCGCT TGAACTCCGG GTATGCTGGT GATTTTGAGG TATTGGGAGT TATACCGCAA     660

GTATATAACT TAAATACTGC ATCGTAAGGA TATCCTTCTG TTTCTGAGAC ACTGGTAAGT     720

ATGCCCATTA CCTATGAATC TCTATGTAGA TGTAATAAGA GCATACACAG TAACTCTTAT     780

TATTAAAAAC AAGACCAATG GTATAAGGGA TAGAAGAAGA GTATTATTAG AGAGGATGAA     840

GTAGATACAG TATATCTACT AGCTAAGGAG TTAGCTTATG ATGTTGTTAC TGGACAGACT     900

GATAAGCTTA CTGCTGCTCT TGCCAAAACC TCCGGTAAAG ACATCGTTCA GTTTGCTAAG     960

GCGGTTGGGG TTTCTCATCC CAGTATTGAT GGGAAGGTTT GTAGGACGAA GCGGAAGGCT    1020

GGTGACAGTA GCGGCACCTA TGCCAAGTAT GGGGAAGAAA CGGATAATAA TACTAGCGGT    1080

CAAAGTACGG TTGCGGTTTG TGGAGAGAAG GCTGGACACA ACGCCAATGG GTCGGGTACC    1140

GTGCAGTCTT TAAAAGACTT TGTAAGAGAG ACGCTAAAAG CGGATGGTAA TAGGAATTGG    1200

CCTACTTCAA GGGAGAAATC GGGAAATACT AACACAAAGC CTCAACCTAA CGACAACGCC    1260

AAAGCTGTAG CTAAAGACCT AGTACAAGAG CTTAATCATG ATGAAAAAAC CATAGTAGCT    1320

GGGTTACTAG CTAAAACTAT TGAAGGTGGG GAAGTGGTTG AGATTAGGGC GGTTTCTTCT    1380

ACTTCTGTGA TGGTCAATGC TTGTTATGAT CTTCTTAGTG AAGGTTTAGG TGTTGTTCCT    1440

TATGCTTGCG TCGGGCTCGG TGGTAACTTC GTGGGCGTGG TTGATGGGCA TATCACAATC    1500

CGTTGGGCTT CGACCCTATA TGCTCACAGC AAGTCACTAG GCAAAATTGG AGCTGCATCA    1560

CTCCGAAACA GACTACGATC AGCGATTCTC CATACCTAGT AGATCAGTAC AGTGGCTTTA    1620

TACTCTTACC CAGCATGAAA TACTTGCTAT CTAAGAATCT CCTCTAAAAC TTTCCAGAGG    1680

TTATCTGTAC TTCGAGAGGA AGCTAATCTG CGACTAATAC GGATGGTGTT TATAATATCA    1740

CTCCTAAACT TGCTTATAGG TTAAAAGCTG GGTTGAGTTA TCAGCTTTCT CATGAAATCT    1800

CGGCTTTTGC GGGTGGCTTC TACCATCGTG TTGTTGGTGA TGGTGTTTAT GATGATCTTC    1860

CGGCTCAACT ACCTACAAAT TGATAGGTAC ACTAAAAGCC CACGTAATAA CTCTCATTAT    1920

TAAAATGAGG AAGATGAAGC AGATACAGTA TATCTACTAG CTAAGGAGTT AGCTTATGAT    1980

GTTGTTACTG GGCAGACTGA TAACCTTGCT GCTGCTCTTG CCAAAACTTC CGGTAAAGAC    2040
```

```
TTTGTTCAGT TTGCGAATGC TGTGAAAATT TCTGCCCCTA ATACTCGTGC CGAATTCGGC    2100

ACGAGCGGCA CGAGCTATAT TTAACTTATA AGAAATCAGC AGACTATTTT TCAAATTGAT    2160

TGTACAATTT ACCTTACCTG GGAATATATG TGAGAACCCT GGCTTCTCTA CCTTTTAACA    2220

ATATTTGCTA TTATTATTTT TAAAGTATTA GCTATTGTGG TTATGTGGAA TTAAATATCA    2280

ACTTGGTTTC AATTTGCATT TTCCTAATGA GGAATGCTGT TGACTACGTT TTGCATGTGC    2340

TTGTGGGCCA TTTATGTATC TTCATTACAT TTGTTAAGGG ATCGTGTGAG ACATTCATTC    2400

ATTTTTATTT TATTGTCATT CCATTACTTG TTAACTCTTT CTACTAGTCT TTTAAAATAA    2460

TGTTTAATTT ATCACCTTTT TATTTATGGC TTTCTTTTCT TGGCCTTGTT GGACAGATAT    2520

TTTTCCTACC CCACATCATG AAGACAGTCC CCTATGTTCT TGTTTGTTTG ATAAAATACG    2580

TAGACTTTAA CTCTTGAATG AGATGCATAA CTTACCTCAA ATTAAGTTTG TGAATGTTAG    2640

TAGGTAGAGG GCAACATACA AATTGTATAT GAATATATTG TTGTTCCATC ATCATTGGTT    2700

TAAAAAATTC TTAATTCTCC TGATGAAATT ACTTGGGATG TCTGTCAAAT AAATCTTAAA    2760

ATACTTTTTG TTAATTTTTA TTAAGTAGTG TACTGAAATT AAATTGGAAC TGGTTAAATC    2820

TATAGATTGT TAAATTGAAT ATATAAAGGT TAAATTGAAA TTCATTCAAT TCATGTACTT    2880

CTTAAATTTC TATCAGCTAA CTTTTATAAT TTTTGGTATA GAAATCATAC ACAACATAAA    2940

AAAATACTAA GTATTTTATC TATTTTTGAT ACAAATGTAA ATTAAAATTT AATTTTTTAC    3000

TGCTAATATT ACTTATTTAA AATTTTAACT CTTAATCATT AAATATCTCT AATATCACAT    3060

ATATATTTCA ATGTATATAA TTATAAAGTA ACACTTCTTC CTTGTCAATT TGTGTGGCTT    3120

GTACTAAATT GTATTAATTT TTCTTTATTT AAGATGTCTT TATTTCCTCT TTATTCTTCA    3180

ATAATATGTT CTCTGGAATC AAAATCAAGA TTTACATTTC TTTTATTTCT ACACTTGAGA    3240

GATATGGTGT CAGTTCTTCC TGGTTTCCAT GATTTCCATA GTTCCCACTG TTTTCATGAA    3300

ATCCACTGTT AAGCAATTTA TCCCCTTTAT ATAAAGTGTC ATTTTTTGT TGTTACTTTC     3360

TTTGTTGTAT TTAGTTTTTA GAAATTTGAT TATGATATGT TGTAGTGTAG ATTTCCCAGG    3420

TGTTTTCTTG TTTGATGTTC TCTAGTTTGG TGGCTACCTT GTTGAATCTA TAGGTTTTTT    3480

TATTTACACT TAACTAAATT TGAGAAGTTG TCAGCCATTA TTTTCTTAAA TTACTTTTGA    3540

CTTTTTTAGC CTCTACTATT TCTATTTCTT TTTTTGAGGC TCTGATGACA TGGATATGAG    3600

GTCTTTTGTT TTAGTTCCAC AACTCGTGCC GCTCGTGCCG AATTCGGCAC GAGAAAAGGA    3660

CAAATGTTGT ACAGTTTCAC TTACATGAGA TACCTAGCAC AGGCCTTTTC ATAGGGAAAG    3720

TGGAATAGAG GTTACCAGAG CTCAGGGCAT TGGGAAATGG GGAGTATTGT TTAATGGGCA    3780

CGGAGTTTCT GTTTGAGATG AGGAAAAAGT TCTGGAAATG TGCAGTATTG TACAAGCTCA    3840

CAAATTGTAC TAAGCTCATC AATTTAATGT TAATGCCACT GAATTGTCTA CTTAAAAATT    3900

GTTAAAATGT TAATTTTCAT ATTGTGTATA TTTGACCACA GTTTAAA                  3947
```

(2) INFORMATION FOR SEQ ID NO:48:

(i) SEQUENCE CHARACTERISTICS:
        (A) LENGTH: 5521 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:48:

```
TTCACCTGGC CAAATCTTAT TGGATCTTCA GGACAAAGAC CAAGAATCTG CTTCTCCAAG    60
```

```
AAGCATTCTC TGACCCCCAC CTACCTATCT GACTCTTAGC TTAGATTCCT AATGGTGTGA    120
GTGTGTCAGA GCCTTTACTT AGTCTAAGCG TAACTGTAAA AACATCTTTT CAAAAGTCTC    180
TGCATGACTG TCTAGGTCTC ACCTATCACA CTGTAAGCAT CTGGAAAACA AAGCCACTGA    240
GTCTTCCTTT TACCAAAAAG GCCTAGCCTT GTTTTTGACA AATGGCAAGA ACACATTAGA    300
TGTTTGTTGA GAGAACAAAA GGAGAGAACT CATTATGAAA CTCTGGACAA CATTTATATA    360
CCTCTCTACA TTTTTTGTGT TGGAGGTTAG TTTTCTTTTC TAATAATTTG ATTTCTTTGG    420
ATACATCGAG GCAATACACT TAAGAAGCAA GAAGATTGGG GCCAGCCTTC TAGACTGTTC    480
AAAGGGTTAC ACCCAACAGA AGGGAAATAT TCCCGAGATG ACCTTGGTGC CTGTTGGGGT    540
GATCAAGCCC AACACCAGGC CGTCGGGGCT ACAAAGTCCA GTGGGGTCAA AGGAATGAGA    600
AAAGACAAGT TAAGAGTGCA TAAAGTGTAT CCAGGGGGCT AACGCTAGAT TGGAGGCTGT    660
GAAGGCCCGG AGCTCTGGGA GCCCACACTA TTTATTGCTG GAGTAGAAAG GTAGCAGTGC    720
ATCAAGTGTA GCTGTGACAG TTTAGCATTT TCTTTGACAC ATATAGAATA TGCTCTGCTG    780
CTTGATATAA TGGAGAGCAT GTTTATGAGC CTGGGAGAGC AACCAACAAG TCTGTGCACA    840
TTCCAGAGGC TACGAGGGGC TTTATGCCCT GAGCCCTGGA TTCCATCCAA GCCGCAAGGG    900
GTTTTATGCC CTGGGCTTAG ATTTGTGGCG TGGCAGTGCA GCCTTCCACC CTTTGGCACA    960
GAGCTTGGTG TTCCAAAGGC CACGAGGGGT TTTAGACCCT GGACCCCGGA CATCCTCCAA   1020
GGATCTTTTA TATTACGACA AACAAGCCAG TCCTGCCTCA GCTCTTCTAC CAACAGGTAC   1080
CTTTGGCCAA ATGTCTGAAA TAGGGTTACA GATTCTATAA CTGATGGATC TCCTAACAGG   1140
ATAATTGAGT GTCTTATAGG GAAGTTGACA TTTTTTTGGT TACTCTACTC CAAGGCATTG   1200
AATTGTTTAC AGTTTTTATT TGTTCATGGT GGAAACTGTG GCTGTATATT ATTTCTTATT   1260
GGTGTAGGCT AGTATGATAA ACTTTGCTTA TCTTTTAGTT TGTTATCAAC CCATAGTAGC   1320
ACATCAAACT GAATCTACAA AAAAAACTAT GGAAAACCCT TATGTATGTG TTTCATGAGC   1380
AAAATTACCT TTGCTTCAAA TTCCAACCTT GGAAATGTTT CTTGAGTTTC TACAGGTAGT   1440
CTAATACCAG ATTCTATGTA CCTTGTTGTA ACCTCGTGCC GAATTCGGCA CGAGCTCGTG   1500
CCGTGCTGAG TCATTATTTC CTCTCATAGA TATAGTGCTT TCTGAAGGAG GAATATCCTA   1560
CCAAAATTTA ACTGACATTG CAGTAATAAT AGGCCCTGGA AGCTTTACTG GGTTAAGAGT   1620
ATCTCTGGCA ACAGCACAAG GTTTTGAGCT TGCTTCTAGT GTTGCTGTTC ATGGGATCAG   1680
TCTTCTTGAA CTACAAGCAT ATTCAATTTT GTGTGCTTCT GAACAAACTG AAGAAGATAT   1740
AGTTGCTGTG ATAGAATCTA CAAAAGCCGA TTTTGTCTAT TATCAAATGT TCAATAACTC   1800
CCTCATTCCC CTAACAGGTG TGCATTTAGT GCCTCTAAAT GAAGTGCCTC AAGGCAAAAT   1860
ATTGAAGGGC TCCCCTGCTA TAGCTTTGGA TACCAAGTCT ATTGGGTTGT ACCTTATTTA   1920
TAAACTATCA AATCGACTTC CGAAAACTAC ACTTGCCCCC ATTTATTCGC GCTTTTACCA   1980
CTAGAGTGTC CATGATAATT TAACTGATAA CATCAATCGG GCTAGATATG TGTCTAGCTT   2040
TTGTGCGTAA GCTCTTATGG AAATAAGTGT GATATTTTGC GAGCACATGG TGATGGAGAG   2100
CTCATCTAAG GCAGCCTCAG TAACATGCCC CGCGTCTATG AATTGTGATT GTAATGCGTA   2160
TTAAGGATTC CACAATTTCC TGTGACAACC ACTAAAAGTA GTCTACAAGC TATAAACTCT   2220
TAAATCTATA GATTGCTAGG GCTGATAAAG AACCTTTAGC ATTAGAAGCG TAGAGAGACA   2280
CTGATGGGTT AGAATTTGAT ACAAAAACAT GACCTTATTA CTACAAATAGT TTACTTGTGA   2340
GCAGTGCACA CCAAGAATAT AACATTAAGC TTCTGAGAGG ATACACTCAC TGAGACTCTG   2400
```

```
TGAGATCTGA CGTACCCTTA CCCAATCTAC TACACTCTAC CTCTGGCAAC GCATTCTACA    2460

GAGCACGTTT TAGCGTGAAA ATCTTCACAC GAAGATACCG TTGTATTGTG GCTCCAGTTA    2520

GCGTCACTAA GTATTGAGCT AGCAGTTCCA CCTTGATTAA AAGGTACTGC ATCTTATACA    2580

GACTTTAGCA GTCCCATTAC ATACTCACCT TGATCTAGAA AACAATGATC TAGCCGCACC    2640

TAACATTTCT ATCTTCAAAA AACCACTTAT AGCGTTTTTC TCTCCAACTT CTAAAACATA    2700

CTCTATATAC TTTAAAGGTT TTATTGAGGA AATCAGAAAA GATTTTTCAA GTAACACTGA    2760

GCTTTCTTTT AAACATCTGG TGCAGAGATA TGTACTACAC AAACTGAAAT ATAAACGTTT    2820

TGGAAAATAT CTATAAATAT GAAACATTAA GTTTTAAGCA TAATATGCTT TAAAACTAGC    2880

AGAATATATT GCAACACATA TTCTATACAT TCTTGCTTGC ATTAGAATAA AAATAGATTG    2940

CTCAAGGAAA CTGCTAGGTA TACATATACC TTTTCACCAA ATTAGCAGTG TATACCTTCT    3000

GGAATACTCA TAAGCGTCTT GTGAATACGA TGTTTTTCTA CACTGCAGGT AAGATGACGT    3060

TTGGCCTATT TTTCGTATCA GCAGGGCTCA GGTAAATGAT GTATGTGCGG TGTTATTATC    3120

TATCAACAAA TGCGTATGGT GTATTTTTGA TGCCGAAAAT TGTCTCCATC TCACAGGCAG    3180

CATATCTTAC TCTTGTAAGC ATATAAAATT TTAGTTCACA GTGTTAAGAA ACACTGTTAT    3240

TTGATCCCTT GAAGGTATGC TTAAACGGTT TGAAAATGCA CGTCCTGCAG TGTGTTTGTA    3300

ATACCTGTTC TAACAACCAA GAGCTTTAAG CATCTCGAAA AAGCTTTTAA GAAATTGATG    3360

CGTCCCCTAG TAGTGCCGCG GTAAGCATTA TTATGAACGC TCAAAGGTAT AGTATTTTGG    3420

CATATTGAAT ATTACAGTAC AGCATCAATA TACAGTTTAA AACTCAAGTA TCACATCTCC    3480

TACTGCTATC ATCTATGCTG GAAAAACTCA TTTATACCCT GTGATGCGCT TTTAAGAGTG    3540

TTACACTGTT AATTCTTTCC TCTGTTTAAA TGTTATGCAG AACATGAGTA ATAAAACTAA    3600

TAGAAGATAT GTGAGAAGAG GCATTCAGCC CATTACTTAC TCATGGATTA GATAAGAAAC    3660

TAGAGCCACG TTTGCTTCTG TTTTTCGTGA CATGCTTATG TAGAATTCTG CACAAGCAGC    3720

AGAATGGTGC TTTCATTAAC ACGGATGTAT ATGGGATGGG TAAGGGCTCT TAAGCTTTGC    3780

ATGGCAAGGT TCTATAGCTT TTTAGAACTT CATATATCGT ACCGAAACAA ATTAATACGG    3840

GTCTATCCAT ACATTACGTA ATGGCTACTA TGCAAAATTC AGAATATTGC CCATAAACAA    3900

CTAGAAAAAG TCTTGCAGAT TTTTTCTGAT TACTATATTC CTTCGGGAAT CTGACCAGCT    3960

ATGGGCGTTC TGTTATGCGA TCAAGGAAGA TTTATGTTTG GGTGGTCATG GCAACGGTTT    4020

TAGGTGCCAT GGCTTTTGTC ACTTTTGGAA GCATGGATACC AATGGGTAAG TTGTCTAATT    4080

CTGGCAACGG ACAGTGCGTT GCAATGTTGG GTAATAAATG TCTACCATTG CGGGATTACC    4140

GTATAATGTA CCGCAACGAG TTGGCAGAAC TAGAGAAGAT GTTACAACAC AAATTGTCTG    4200

ATGCTCAAAT TAATCAGTTT GGTATTAAGG AAGTTGTCCT CAAGAACATG ATAGCCGACA    4260

TGGTCGTTGA AAAGTTTGCT CATGACTTAG GCATACGTGT TGGCTCAAAT AGCTTACGGA    4320

GTCTGATCAA AAATATAAGA ATATTTCAGG ATGCTAATGG TGTCTTCGAC CAGGAGAGAT    4380

ATGAAGCCGT ATTGGCTGAC AGCGGAATGA CTGAGTCGTC CTATGTGAAT AAAATTCGCA    4440

ATGCTTTACC TTCTACTATT CTAATGGAGT GTTTATTCCC TAATAGGGCG GAATTACATA    4500

TTCCTTATTA TGATGCATTA GCAAAAGATG TTGTGTTGGG ATTGCTGCAG CATCGTGTGG    4560

CAGACATAGT GGAAATATCT TCTGATGCCG TAGACATTTC AGGAAGTGAT ATATCTGATG    4620

ATGAATTGCA AAAATTGTTT GAGGAGCAGT ACAAGAATTC TCTAAATTTC CTGAATATC    4680

GCAGTGCTGA TTATATAATC ATGGCAGAAG ACGACTTGCT TGCTGATGTC ATTGTTTCGG    4740

ATCAAGAGGT AGACGTTGAG ATTAAAAACA GTGAACTACA TGATCAAAGA GATGTTCTAA    4800
```

-continued

```
ATTTAGTATT TACAGACAAA AATGAAGCTG AGCTAGCTTA CAAAGCTTAC CAAGAGGGTA    4860

AGTCTTTTGA GGAATTGGTT AGTGATGCTG GCTACACCAT AGAGGATATT GCACTCAATA    4920

ATATCTCTAA GGATGTTCTT CCGGTAGGTG TGCGAAATGT GGTGTTTGCA CTAAATGAAG    4980

GAGAAGTCAG TGAAATGTTC CGTAGCGTTG TCGGCTGGCA TATCATGAAG GTAATAAGGA    5040

AGCATGAGAT CACTAAGGAA GACCTAGAAA AGCTGAAAGA GAAGATATCT TCAAATATTA    5100

GAAGGCAAAA GGCAGGTGAG TTGCTAGTTA GCAATGTGAA AAAAGCAAAC GATATGATCA    5160

GCCGCGGGGC ATTGCTGAAT GAACTAAAGG ATATGTTTGG TGCGCGGATC AGTGGTGTTT    5220

TGACGAATTT TGATATGCAT GGGCTCGATA AATCTGGCAA CTTAGTGAAA GACTTTCCGT    5280

TGCAGCTTGG TATAAACGCC TTTACTACTT TGGCGTTTTC ATCTGCCGTA GGAAAACCGT    5340

CTCATCTGGT TAGCAATGGT GACGCTTATT TCGGCGTTCT TGTTACTGAA GTAGTGCCTC    5400

CAAGACCAAG GACACTTGAA GAAAGCAGGT CTATTCTTAC TGAAGAATGG AAGAGTGCAT    5460

TACGTATGAA GAAATACGT GAATTTGCTG TGGAGTTGCG CTCGAAGCTA CAAAATGGCA    5520

C                                                                  5521
```

(2) INFORMATION FOR SEQ ID NO:49:

(i) SEQUENCE CHARACTERISTICS:
        (A) LENGTH: 1938 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:49:

```
TTGAGGAGTA TTAAGCAAGT CTCCGAAAGA TGAGTTTGAC AAATGCTTTC GAGACTCTTT      60

AAGCATCTTT AAAAAGCATT TTTCTGTAAC CTTATCAGAA TATAAAGCCT CATGTAACGC     120

TGTATCTCCC ATATGAGAAA GGAGTGCTTG ACAGCTATCT GGGCATTTTT TCGCAATTTA     180

CTTATATAGC TTACCGTCAC CATTAGCAGC TGCTATATGT AAAGCCGTCT TACCATAAGC     240

ATCTCTCTGC GTTGCTGGAG CCCCTTTATC CAAGAGCAAC CTAGCAGTCT TCTGGTTGCC     300

AGCAGCTGTT GCTAAATGCA AGGCTGGAGT TCCAGTGTGA TCCGTAGACG AAAGATCTGC     360

ACCCCTCTGT AAAAGGAAAT TTACAATCCT ATTAGCCTCT TTAAGGTTAC TTGCCTCATT     420

TGCCACTTGA ACTGCAGCAG CTAAAGGGCT CATAGATCCG GTAGGAGTAT TTATATGTGC     480

CCCAGCTTCT ACAACACGCT TTAAATGCTT TATAGCTTTA CCCCCCTGAA AGCACCCTCC     540

TTGTATACCC ACAGAAATAG CTGGTTCTGG AGACGCATTT ACATCAGCAC TGTTTTTAAT     600

TAACGTCTTC ACTGCAGCAT ATTGACCACT AGTTAGTGCT TCAGCGGTCA AAGTTGTCTT     660

TTTTCCTTCA GGAGTTGTAA TTTCTTCATT TACACTAATC ACTTCAGTGG TAATAAGATG     720

CCTCAATACA TCTGCTGCAC CTTTTCTTAC TGCCTCGACA GCAACATGCT GCGGGTAAGG     780

CTCATATCTC ATTAACATGT CAAGTGCTGG TAGCGATACT TTTCCACCAC TTGCTTCACG     840

AATCGCATAT ACACCTGGAG TAGGAACACC ATCCTTTACA GGAAACTTAG AATAACTACT     900

CTTCCTTCCA AGAGCCTGCT GCAATATCTC TAAATTTCCA TCCTTTGCTG CGTAATGTAT     960

TATAGTTCCA CCATCATGTG ACCGAGCATC TACGTCCATG CTATTACAGC GTAACATAGT    1020

CTTAACACCC TCAGTGTTGC CCCCTTTATA CGCAGCTACC ACAGGCGTTT CACCTGTCAC    1080

TGGAGATGGT ACATTGATTG ATGGAATATT ACGCACATTC TCAATCAACA TCTGCAATTT    1140

AACGCTTACG CCTTTATGGC TTGGCTCATC CTCAACTATC ATGTGAATAG GCGCTTTGCC    1200
```

```
ATTCGGTGCT AATTGATTTA CAACAGACTC AGGAGTGCAT CTTACCACCT GCTCAAAAAC    1260

CCCCACTGTT GATTTTTGTG CTGCAGCATG TATAGGTGCA TTACCTGCAA TATCTAAATT    1320

AGTAAAAGGT TCCTCTCCAT ACCTATGATA TGCTTCCTCC AATACCCTTT TCGCAAGAGG    1380

ATCAAAATTT GGGGTCCCAT TAGAAGATAC AAAATGCACC AGCGTTGATG CGTCCTCTGG    1440

ATTAGGACAT GTAAGAGAG ATTTTACTTC TGAAGAAGCT GAGCCATACA CTTTATCTGC     1500

AATGTTCATG GCCTTCTCGA AGATCTTCTC AGCCTCCGGT ATAGCCTTCT AATAGCATAC    1560

TGTACTGCAC TCATCCCTTT TTTATCCGGG AATATTAGTG CCTCTGCACA CTGCGATTGC    1620

CCTCAATATT TGACGACACC GCTTCTTGCA TCTTGTCAAT GTATGATAAA ACATCCCGCC    1680

TTGGCCATTG CTTTGCAACA ATGTGGCAAA CGGTTTCACC AGCATCATTT GCAACGCTAA    1740

TATCACTTAA CCTTGAGAGA AGATGCTTTA CTTTCTGGTG ATCCATACGC TCCGTAGCAA    1800

TATGAAGCGG AGTGTTTCCA CCCGGTCCCT TAGCATTAAC ATCTGCTATA AGAGCTTTGT    1860

CGCATAGTAC ATCAAGATTG CCTAAAGCAT TTTTGCCTAC TGAAGATGCA GCTGTATGTA    1920

ATGGCGTATT ACCATCTA                                                  1938
```

(2) INFORMATION FOR SEQ ID NO:50:

(i) SEQUENCE CHARACTERISTICS:
        (A) LENGTH: 578 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:50:

```
Met Tyr Gly Ile Asp Ile Glu Leu Ser Asp Tyr Arg Ile Gly Ser Glu
1               5                  10                  15

Thr Ile Ser Ser Gly Asp Asp Gly Tyr Tyr Glu Gly Cys Ala Cys Asp
            20                  25                  30

Lys Asp Ala Ser Thr Asn Ala Tyr Ser Tyr Asp Lys Cys Arg Val Val
        35                  40                  45

Arg Gly Thr Trp Arg Pro Ser Glu Leu Val Leu Tyr Val Gly Asp Glu
    50                  55                  60

His Val Ala Cys Arg Asp Val Ala Ser Gly Met His His Gly Asn Leu
65                  70                  75                  80

Pro Gly Lys Val Tyr Phe Ile Glu Ala Glu Ala Gly Arg Ala Ala Thr
                85                  90                  95

Ala Glu Gly Gly Val Tyr Thr Thr Val Val Glu Ala Leu Ser Leu Val
            100                 105                 110

Gln Glu Glu Glu Gly Thr Gly Met Tyr Leu Ile Asn Ala Pro Glu Lys
        115                 120                 125

Ala Val Val Arg Phe Phe Lys Ile Glu Lys Ser Ala Ala Glu Glu Pro
    130                 135                 140

Gln Thr Val Asp Pro Ser Val Val Glu Ser Ala Thr Gly Ser Gly Val
145                 150                 155                 160

Asp Thr Gln Glu Glu Gln Glu Ile Asp Gln Glu Ala Pro Ala Ile Glu
                165                 170                 175

Glu Val Glu Thr Glu Glu Gln Glu Val Ile Leu Glu Glu Gly Thr Leu
            180                 185                 190

Ile Asp Leu Glu Gln Pro Val Ala Gln Val Pro Val Val Ala Glu Ala
        195                 200                 205
```

```
Glu Leu Pro Gly Val Glu Ala Ala Glu Ala Ile Val Pro Ser Leu Glu
    210                 215                 220
Glu Asn Lys Leu Gln Glu Val Val Ala Pro Glu Ala Gln Gln Leu
225                 230                 235                 240
Glu Ser Ala Pro Glu Val Ser Ala Pro Ala Gln Pro Glu Ser Thr Val
                245                 250                 255
Leu Gly Val Ala Glu Gly Asp Leu Lys Ser Glu Val Ser Val Glu Ala
                260                 265                 270
Asn Ala Asp Val Ala Gln Lys Glu Val Ile Ser Gly Gln Gln Glu Gln
                275                 280                 285
Glu Ile Ala Glu Ala Leu Glu Gly Thr Glu Ala Pro Val Glu Val Lys
    290                 295                 300
Glu Glu Thr Glu Val Leu Leu Lys Glu Asp Thr Leu Ile Asp Leu Glu
305                 310                 315                 320
Gln Pro Val Ala Gln Val Pro Val Val Ala Glu Ala Glu Leu Pro Gly
                325                 330                 335
Val Glu Ala Ala Glu Ala Ile Val Pro Ser Leu Glu Glu Asn Lys Leu
                340                 345                 350
Gln Glu Val Val Ala Pro Glu Ala Gln Gln Leu Glu Ser Ala Pro
                355                 360                 365
Glu Val Ser Ala Pro Ala Gln Pro Glu Ser Thr Val Leu Gly Val Thr
    370                 375                 380
Glu Gly Asp Leu Lys Ser Glu Val Ser Val Glu Ala Asp Ala Gly Met
385                 390                 395                 400
Gln Gln Glu Ala Gly Ile Ser Asp Gln Glu Thr Gln Ala Thr Glu Glu
                405                 410                 415
Val Glu Lys Val Glu Val Ser Val Glu Thr Lys Thr Glu Glu Pro Glu
                420                 425                 430
Val Ile Leu Glu Glu Gly Thr Leu Ile Asp Leu Glu Gln Pro Val Ala
                435                 440                 445
Gln Val Pro Val Ala Glu Ala Glu Leu Pro Gly Val Glu Ala Ala
    450                 455                 460
Glu Ala Ile Val Pro Ser Leu Glu Glu Asn Lys Leu Gln Glu Val Val
465                 470                 475                 480
Val Ala Pro Glu Ala Gln Gln Leu Glu Ser Ala Pro Glu Val Ser Ala
                485                 490                 495
Pro Val Gln Pro Glu Ser Thr Val Leu Gly Val Thr Glu Gly Asp Leu
                500                 505                 510
Lys Ser Glu Val Ser Val Glu Ala Asp Ala Gly Met Gln Gln Glu Ala
                515                 520                 525
Gly Ile Ser Asp Gln Glu Thr Gln Ala Thr Glu Glu Val Glu Lys Val
                530                 535                 540
Glu Val Ser Val Glu Ala Asp Ala Gly Met Gln Gln Glu Leu Val Asp
545                 550                 555                 560
Val Pro Thr Ala Leu Pro Leu Lys Asp Pro Asp Glu Asp Val Leu
                565                 570                 575
Ser Tyr (2) INFORMATION FOR SEQ ID NO:51:
    (i) SEQUENCE CHARACTERISTICS:
        (A) LENGTH: 125 amino acids
        (B) TYPE: amino acid
        (C) STRANDEDNESS:
        (D) TOPOLOGY: linear
```

```
    (ii) MOLECULE TYPE: protein (ix) FEATURE:
     (A) NAME/KEY: Modified-site
     (B) LOCATION: 1
     (D) OTHER INFORMATION: /note= "Residue can be either Thr
         or Lys"

(ix) FEATURE:
     (A) NAME/KEY: Modified-site
     (B) LOCATION: 4
     (D) OTHER INFORMATION: /note= "Residue can be Gln, Thr or
         Pro"

(ix) FEATURE:
     (A) NAME/KEY: Modified-site
     (B) LOCATION: 7
     (D) OTHER INFORMATION: /note= "Residue can be either Ile
         or Leu"

(ix) FEATURE:
     (A) NAME/KEY: Modified-site
     (B) LOCATION: 9
     (D) OTHER INFORMATION: /note= "Residue can be either Glu
         or Lys"

(ix) FEATURE:
     (A) NAME/KEY: Modified-site
     (B) LOCATION: 11
     (D) OTHER INFORMATION: /note= "Residue can be either Gly
         or Asp"

(ix) FEATURE:
     (A) NAME/KEY: Modified-site
     (B) LOCATION: 71
     (D) OTHER INFORMATION: /note= "Residue can be either Ala
         or Val"

(ix) FEATURE:
     (A) NAME/KEY: Modified-site
     (B) LOCATION: 81
     (D) OTHER INFORMATION: /note= "Residue can be either Ala
         or Thr"

(ix) FEATURE:
     (A) NAME/KEY: Modified-site
     (B) LOCATION: 94
     (D) OTHER INFORMATION: /note= "Residue can be either Asn
         or Asp"

(ix) FEATURE:
     (A) NAME/KEY: Modified-site
     (B) LOCATION: 96
     (D) OTHER INFORMATION: /note= "Residue can be either Asp
         or Gly"

(ix) FEATURE:
     (A) NAME/KEY: Modified-site
     (B) LOCATION: 97
     (D) OTHER INFORMATION: /note= "Residue can be either Val
         or Met"

(ix) FEATURE:
     (A) NAME/KEY: Modified-site
     (B) LOCATION: 98
     (D) OTHER INFORMATION: /note= "Residue can be either Ala
         or Gln"

(ix) FEATURE:
     (A) NAME/KEY: Modified-site
     (B) LOCATION: 100
     (D) OTHER INFORMATION: /note= "Residue can be either Lys
         or Glu"

(ix) FEATURE:
     (A) NAME/KEY: Modified-site
     (B) LOCATION: 101
     (D) OTHER INFORMATION: /note= "Residue can be either Glu
``` or Ala"

(ix) FEATURE:
    (A) NAME/KEY: Modified-site
    (B) LOCATION: 102
    (D) OTHER INFORMATION: /note= "Residue can be either Val
        or Gly"

(ix) FEATURE:
    (A) NAME/KEY: Modified-site
    (B) LOCATION: 105
    (D) OTHER INFORMATION: /note= "Residue can be either Gly
        or Asp"

(ix) FEATURE:
    (A) NAME/KEY: Modified-site
    (B) LOCATION: 107
    (D) OTHER INFORMATION: /note= "Residue can be either Gln
        or Glu"

(ix) FEATURE:
    (A) NAME/KEY: Modified-site
    (B) LOCATION: 108
    (D) OTHER INFORMATION: /note= "Residue can be either Glu
        or Thr"

(ix) FEATURE:
    (A) NAME/KEY: Modified-site
    (B) LOCATION: 110
    (D) OTHER INFORMATION: /note= "Residue can be either Glu
        or Ala"

(ix) FEATURE:
    (A) NAME/KEY: Modified-site
    (B) LOCATION: 112
    (D) OTHER INFORMATION: /note= "Residue can be either Ala
        or Thr"

(ix) FEATURE:
    (A) NAME/KEY: Modified-site
    (B) LOCATION: 114
    (D) OTHER INFORMATION: /note= "Residue can be either Ala
        or Glu"

(ix) FEATURE:
    (A) NAME/KEY: Modified-site
    (B) LOCATION: 115
    (D) OTHER INFORMATION: /note= "Residue can be either Leu
        or Val"

(ix) FEATURE:
    (A) NAME/KEY: Modified-site
    (B) LOCATION: 117
    (D) OTHER INFORMATION: /note= "Residue can be either Gly
        or Lys"

(ix) FEATURE:
    (A) NAME/KEY: Modified-site
    (B) LOCATION: 118
    (D) OTHER INFORMATION: /note= "Residue can be either Thr
        or Val"

(ix) FEATURE:
    (A) NAME/KEY: Modified-site
    (B) LOCATION: 120
    (D) OTHER INFORMATION: /note= "Residue can be either Ala
        or Val"

(ix) FEATURE:
    (A) NAME/KEY: Modified-site
    (B) LOCATION: 121
    (D) OTHER INFORMATION: /note= "Residue can be either Pro
        or Ser"

(ix) FEATURE:
    (A) NAME/KEY: Modified-site
    (B) LOCATION: 124
    (D) OTHER INFORMATION: /note= "Residue can be Val, Thr or
        Ala"

(xi) SEQUENCE DESCRIPTION: SEQ ID NO:51:

```
Xaa Glu Glu Xaa Glu Val Xaa Leu Xaa Glu Xaa Thr Leu Ile Asp Leu
1               5                  10                  15

Glu Gln Pro Val Ala Gln Val Pro Val Ala Glu Ala Glu Leu Pro
            20                  25                  30

Gly Val Glu Ala Ala Glu Ala Ile Val Pro Ser Leu Glu Glu Asn Lys
            35                  40                  45

Leu Gln Glu Val Val Ala Pro Glu Ala Gln Gln Leu Glu Ser Ala
50                  55                  60

Pro Glu Val Ser Ala Pro Xaa Gln Pro Glu Ser Thr Val Leu Gly Val
65                  70                  75                  80

Xaa Glu Gly Asp Leu Lys Ser Glu Val Ser Val Glu Ala Xaa Ala Xaa
                85                  90                  95

Xaa Xaa Gln Xaa Xaa Xaa Ile Ser Xaa Xaa Gln Glu Xaa Xaa Xaa Xaa
            100                 105                 110

Glu Xaa Xaa Glu Xaa Xaa Glu Xaa Xaa Val Glu Xaa Xaa
        115                 120                 125
```

(2) INFORMATION FOR SEQ ID NO:52:

(i) SEQUENCE CHARACTERISTICS:
        (A) LENGTH: 253 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:52:

```
Ala Val Lys Ile Thr Asn Ser Thr Ile Asp Gly Lys Val Cys Asn Gly
1               5                  10                  15

Ser Arg Glu Lys Gly Asn Ser Ala Gly Asn Asn Ser Ala Val Ala
            20                  25                  30

Thr Tyr Ala Gln Thr His Thr Ala Asn Thr Ser Thr Ser Gln Cys Ser
            35                  40                  45

Gly Leu Gly Thr Thr Val Val Lys Gln Gly Tyr Gly Ser Leu Asn Lys
50                  55                  60

Phe Val Ser Leu Thr Gly Val Gly Glu Gly Lys Asn Trp Pro Thr Gly
65                  70                  75                  80

Lys Ile His Asp Gly Ser Ser Gly Val Lys Asp Gly Glu Gln Asn Gly
                85                  90                  95

Asn Ala Lys Ala Val Ala Lys Asp Leu Val Asp Leu Asn Arg Asp Glu
            100                 105                 110

Lys Thr Ile Val Ala Gly Leu Leu Ala Lys Thr Ile Glu Gly Gly Glu
            115                 120                 125

Val Val Glu Ile Arg Ala Val Ser Ser Thr Ser Val Met Val Asn Ala
130                 135                 140

Cys Tyr Asp Leu Leu Ser Glu Gly Leu Gly Val Val Pro Tyr Ala Cys
145                 150                 155                 160

Val Gly Leu Gly Gly Asn Phe Val Gly Val Asp Gly His Ile Thr
            165                 170                 175

Pro Lys Leu Ala Tyr Arg Leu Lys Ala Gly Leu Ser Tyr Gln Leu Ser
            180                 185                 190

Pro Glu Ile Ser Ala Phe Ala Gly Gly Phe Tyr His Arg Val Val Gly
            195                 200                 205
```

-continued

```
Asp Gly Val Tyr Asp Asp Leu Pro Ala Gln Arg Leu Val Asp Asp Thr
    210                 215                 220

Ser Pro Ala Gly Arg Thr Lys Asp Thr Ala Val Ala Asn Phe Ser Met
225                 230                 235                 240

Ala Tyr Val Gly Gly Glu Phe Gly Val Arg Phe Ala Phe
                245                 250
```

(2) INFORMATION FOR SEQ ID NO:53:

(i) SEQUENCE CHARACTERISTICS:
        (A) LENGTH: 366 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:53:

```
Tyr Met Arg Ser Arg Ser Lys Leu Leu Leu Gly Ser Val Met Met Ser
1               5                   10                  15

Met Ala Ile Val Met Ala Gly Asn Asp Val Arg Ala His Asp Asp Val
                20                  25                  30

Ser Ala Leu Glu Thr Gly Gly Ala Gly Tyr Phe Tyr Val Gly Leu Asp
            35                  40                  45

Tyr Ser Pro Ala Phe Ser Lys Ile Arg Asp Phe Ser Ile Arg Glu Ser
50                  55                  60

Asn Gly Glu Thr Lys Ala Val Tyr Pro Tyr Leu Lys Asp Gly Lys Ser
65                  70                  75                  80

Val Lys Leu Glu Ser His Lys Phe Asp Trp Asn Thr Pro Asp Pro Arg
                85                  90                  95

Ile Gly Phe Lys Asp Asn Met Leu Val Ala Met Glu Gly Ser Val Gly
                100                 105                 110

Tyr Gly Ile Gly Gly Ala Arg Val Glu Leu Glu Ile Gly Tyr Glu Arg
            115                 120                 125

Phe Lys Thr Lys Gly Ile Arg Asp Ser Gly Ser Lys Glu Asp Glu Ala
130                 135                 140

Asp Thr Val Tyr Leu Leu Ala Lys Glu Leu Ala Tyr Asp Val Val Thr
145                 150                 155                 160

Gly Gln Thr Asp Asn Leu Ala Ala Leu Ala Lys Thr Ser Gly Lys
                165                 170                 175

Asp Ile Val Gln Phe Ala Asn Ala Val Lys Ile Thr Asn Ser Ala Ile
                180                 185                 190

Asp Gly Lys Ile Cys Asn Arg Gly Lys Ala Ser Gly Ser Lys Gly
                195                 200                 205

Leu Ser Ser Ser Lys Ala Gly Ser Cys Asp Ser Ile Asp Lys Gln Ser
    210                 215                 220

Gly Ser Leu Glu Gln Ser Leu Thr Ala Ala Leu Gly Asp Lys Gly Ala
225                 230                 235                 240

Glu Lys Trp Pro Lys Ile Asn Asn Gly Thr Ser Asp Thr Thr Leu Asn
                245                 250                 255

Gly Asn Asp Thr Ser Ser Thr Pro Tyr Thr Lys Asp Ala Ser Ala Thr
                260                 265                 270

Val Ala Lys Asp Leu Val Ala Leu Asn His Asp Glu Lys Thr Ile Val
        275                 280                 285

Ala Gly Leu Leu Ala Lys Thr Ile Glu Gly Gly Glu Val Val Glu Ile
290                 295                 300
```

```
Arg Ala Val Ser Ser Thr Ser Val Met Val Asn Ala Cys Tyr Asp Leu
305                 310                 315                 320

Leu Ser Glu Gly Leu Gly Val Val Pro Tyr Ala Cys Val Gly Leu Gly
            325                 330                 335

Gly Asn Phe Val Gly Val Val Asp Gly His Ile Thr Pro Lys Leu Ala
            340                 345                 350

Tyr Arg Leu Lys Ala Gly Leu Ser Tyr Gln Leu Ser Pro Glu
            355                 360             365
```

(2) INFORMATION FOR SEQ ID NO:54:

(i) SEQUENCE CHARACTERISTICS:
        (A) LENGTH: 340 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:54:

```
Arg Ser Asp Tyr Gln Gly Gln Val Leu Ala Ile Ile Arg Pro Gln Gly
1               5                   10                  15

Glu Ala Thr Ala Glu Gly Val Asn Lys Glu Pro Glu Ser Lys Glu Glu
            20                  25                  30

Val Leu Ala Gln Pro Val Val Ala Gln Ala Val Ser Thr Gln Lys Pro
        35                  40                  45

Gln Glu Lys Thr Ile Ile Glu Gly Lys Gly Leu Val Thr Pro Thr Val
    50                  55                  60

Glu Asp Phe Val Ala Gly Ile Asn Thr Thr Pro Thr Ser Arg Ala Leu
65                  70                  75                  80

Gly Met Ser Ala Lys Ser Glu Gln Asp Lys Lys Ile Val Ala Ser Gln
                85                  90                  95

Pro Ser Lys Asp Leu Met Ser Cys His Gly Asp Val Val Gly Glu Arg
            100                 105                 110

Arg Val Lys Met Ser Lys Ile Arg Gln Val Ile Ala Ala Arg Leu Lys
            115                 120                 125

Glu Ser Gln Asn Thr Ser Ala Thr Leu Ser Thr Phe Asn Glu Val Asp
130                 135                 140

Met Ser Lys Val Met Glu Leu Arg Ala Lys Tyr Lys Asp Ala Phe Val
145                 150                 155                 160

Lys Arg Tyr Asp Val Lys Leu Gly Phe Met Ser Phe Phe Ile Arg Ala
            165                 170                 175

Val Val Leu Val Leu Ser Glu Ile Pro Val Leu Asn Ala Glu Ile Ser
            180                 185                 190

Gly Asp Asp Ile Val Tyr Arg Asp Tyr Cys Asn Ile Gly Val Ala Val
            195                 200                 205

Gly Thr Asp Lys Gly Leu Val Val Pro Val Ile Arg Arg Ala Glu Thr
            210                 215                 220

Met Ser Leu Ala Glu Met Glu Gln Ala Leu Val Asp Leu Ser Thr Lys
225                 230                 235                 240

Ala Arg Ser Gly Lys Leu Ser Val Ser Asp Met Ser Gly Ala Thr Phe
            245                 250                 255

Thr Ile Thr Asn Gly Gly Val Tyr Gly Ser Leu Leu Ser Thr Pro Ile
            260                 265                 270

Ile Asn Pro Pro Gln Ser Gly Ile Leu Gly Met His Ala Ile Gln Gln
            275                 280                 285
```

Arg Pro Val Ala Val Asp Gly Lys Val Glu Ile Arg Pro Met Met Tyr
    290                 295                 300

Leu Ala Leu Ser Tyr Asp His Arg Ile Val Asp Gly Gln Gly Ala Val
305                 310                 315                 320

Thr Phe Leu Val Arg Val Lys Gln Tyr Ile Glu Asp Pro Asn Arg Leu
                325                 330                 335

Ala Leu Gly Ile
            340

(2) INFORMATION FOR SEQ ID NO:55:

(i) SEQUENCE CHARACTERISTICS:
        (A) LENGTH: 177 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:55:

Gly Val Phe Met Gly Arg Gly Thr Ile Thr Ile His Ser Lys Glu Asp
1               5                   10                  15

Phe Ala Cys Met Arg Arg Ala Gly Met Leu Ala Ala Lys Val Leu Asp
                20                  25                  30

Phe Ile Thr Pro His Val Val Pro Gly Val Thr Thr Asn Ala Leu Asn
            35                  40                  45

Asp Leu Cys His Asp Phe Ile Ile Ser Ala Gly Ala Ile Pro Ala Pro
        50                  55                  60

Leu Gly Tyr Arg Gly Tyr Pro Lys Ser Ile Cys Thr Ser Lys Asn Phe
65                  70                  75                  80

Val Val Cys His Gly Ile Pro Asp Asp Ile Ala Leu Lys Asn Gly Asp
                85                  90                  95

Ile Val Asn Ile Asp Val Thr Val Ile Leu Asp Gly Trp His Gly Asp
                100                 105                 110

Thr Asn Arg Met Tyr Trp Val Gly Asp Asn Val Ser Ile Lys Ala Lys
            115                 120                 125

Arg Ile Cys Glu Ala Ser Tyr Lys Ala Leu Met Ala Ala Ile Gly Val
130                 135                 140

Ile Gln Pro Gly Lys Lys Leu Asn Ser Ile Gly Leu Ala Ile Glu Glu
145                 150                 155                 160

Glu Ile Arg Gly Tyr Gly Tyr Ser Ile Val Arg Asp Tyr Cys Gly His
                165                 170                 175

Gly (2) INFORMATION FOR SEQ ID NO:56:

(i) SEQUENCE CHARACTERISTICS:
        (A) LENGTH: 197 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:56:

Glu Trp Trp Cys Thr Pro Leu Trp Cys Ala Lys Asn Thr Ile Met Leu
1               5                   10                  15

Cys Arg Leu Lys Asn Thr Gly Cys Glu Val Met Arg Glu Val Leu
                20                  25                  30

-continued

```
Val Pro Tyr Ala Gly Val Ser Pro Ser Val Asp Ser Thr Ala Phe Ile
            35                  40                  45

Ala Gly Tyr Ala Arg Ile Ile Gly Asp Val Cys Ile Gly Lys Asn Ala
        50                  55                  60

Ser Ile Trp Tyr Gly Thr Val Leu Arg Gly Asp Val Asp Lys Ile Glu
65                  70                  75                  80

Val Gly Glu Gly Thr Asn Ile Gln Asp Asn Thr Val Val His Thr Asp
                85                  90                  95

Ser Met His Gly Asp Thr Val Ile Gly Lys Phe Val Thr Ile Gly His
                100                 105                 110

Ser Cys Ile Leu His Ala Cys Thr Leu Gly Asn Asn Ala Phe Val Gly
            115                 120                 125

Met Gly Ser Ile Val Met Asp Arg Ala Val Met Glu Glu Gly Ser Met
        130                 135                 140

Leu Ala Ala Gly Ser Leu Leu Thr Arg Gly Lys Ile Val Lys Ser Gly
145                 150                 155                 160

Glu Leu Trp Ala Gly Arg Pro Ala Lys Phe Leu Arg Met Met Thr Glu
                165                 170                 175

Glu Glu Ile Leu Tyr Leu Gln Lys Ser Ala Glu Asn Tyr Ile Ala Leu
                180                 185                 190

Ser Arg Gly Tyr Leu
            195
```

(2) INFORMATION FOR SEQ ID NO:57:

(i) SEQUENCE CHARACTERISTICS:
      (A) LENGTH: 172 amino acids
      (B) TYPE: amino acid
      (C) STRANDEDNESS:
      (D) TOPOLOGY: linear (ii) MOLECULE TYPE: protein (xi) SEQUENCE DESCRIPTION: SEQ ID NO:57:

```
Ala Asn Leu Ala Arg Ala Thr Ala Pro Ser Met Phe Ser Phe Ser Leu
1               5                   10                  15

Lys Gly Arg Pro Ser Phe Phe Glu Ile Ala Phe Ser Leu Gly Ser Val
                20                  25                  30

Met Met Ser Met Ala Ile Val Met Ala Gly Asn Asp Val Arg Ala His
            35                  40                  45

Asp Asp Val Ser Ala Leu Glu Thr Gly Gly Ala Gly Tyr Phe Tyr Val
        50                  55                  60

Gly Leu Asp Tyr Ser Pro Ala Phe Ser Lys Ile Arg Asp Phe Ser Ile
65                  70                  75                  80

Arg Glu Ser Asn Gly Glu Thr Lys Ala Val Tyr Pro Tyr Leu Lys Asp
                85                  90                  95

Gly Lys Ser Val Lys Leu Glu Ser Asn Lys Phe Asp Trp Asn Thr Pro
                100                 105                 110

Asp Pro Arg Ile Gly Phe Lys Asp Asn Met Leu Val Ala Met Glu Gly
            115                 120                 125

Ser Val Gly Tyr Gly Ile Gly Gly Ala Arg Val Glu Leu Glu Ile Gly
        130                 135                 140

Tyr Glu Arg Phe Lys Thr Lys Gly Ile Arg Asp Ser Gly Ser Lys Glu
145                 150                 155                 160

Asp Glu Ala Asp Thr Val Tyr Leu Leu Ala Lys Glu
                165                 170
```

(2) INFORMATION FOR SEQ ID NO:58:

(i) SEQUENCE CHARACTERISTICS:
        (A) LENGTH: 196 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:58:

```
Lys Leu Lys Glu Asp Val Ala Ser Met Ser Asp Glu Ala Leu Leu Lys
 1               5                  10                  15

Phe Ala Asn Arg Leu Arg Arg Gly Val Pro Met Ala Ala Pro Val Phe
            20                  25                  30

Glu Gly Pro Lys Asp Ala Gln Ile Ser Arg Leu Leu Glu Leu Ala Asp
        35                  40                  45

Val Asp Pro Ser Gly Gln Val Asp Leu Tyr Asp Gly Arg Ser Gly Gln
 50                  55                  60

Lys Phe Asp Arg Lys Val Thr Val Gly Tyr Ile Tyr Met Leu Lys Leu
 65                  70                  75                  80

His His Leu Val Asp Asp Lys Ile His Ala Arg Ser Val Gly Pro Tyr
                85                  90                  95

Gly Leu Val Thr Gln Gln Pro Leu Gly Gly Lys Ser His Phe Gly Gly
            100                 105                 110

Gln Arg Phe Gly Glu Met Glu Cys Trp Ala Leu Gln Ala Tyr Gly Ala
        115                 120                 125

Ala Tyr Thr Leu Gln Glu Met Leu Thr Val Lys Ser Asp Asp Ile Val
130                 135                 140

Gly Arg Val Thr Ile Tyr Glu Ser Ile Ile Lys Gly Asp Ser Asn Phe
145                 150                 155                 160

Glu Cys Gly Ile Pro Glu Ser Phe Asn Val Met Val Lys Glu Leu Arg
                165                 170                 175

Ser Leu Cys Leu Asp Val Val Leu Lys Gln Asp Lys Glu Phe Thr Ser
            180                 185                 190

Ser Lys Val Glu
        195
```

(2) INFORMATION FOR SEQ ID NO:59:

(i) SEQUENCE CHARACTERISTICS:
        (A) LENGTH: 719 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:59:

```
Gly Phe Thr Ile Met Lys Thr Leu Asp Leu Tyr Gly Tyr Thr Ser Ile
 1               5                  10                  15

Ala Gln Ser Phe Asp Asn Ile Cys Ile Ser Ile Ser Ser Pro Gln Ser
            20                  25                  30

Ile Arg Ala Met Ser Tyr Gly Ile Lys Asp Ile Ser Thr Thr Ile
        35                  40                  45

Tyr Arg Thr Phe Lys Val Glu Lys Gly Gly Leu Phe Cys Pro Lys Ile
 50                  55                  60

Phe Gly Pro Val Asn Asp Asp Glu Cys Leu Cys Gly Lys Tyr Arg Lys
 65                  70                  75                  80
```

-continued

```
Lys Arg Tyr Arg Gly Ile Val Cys Glu Lys Cys Gly Val Glu Val Thr
                85                  90                  95
Ser Ser Lys Val Arg Arg Glu Arg Met Gly His Ile Glu Leu Val Ser
            100                 105                 110
Pro Val Ala His Ile Trp Phe Leu Lys Ser Leu Pro Ser Arg Ile Gly
        115                 120                 125
Ala Leu Leu Asp Met Pro Leu Lys Ala Ile Glu Asn Ile Leu Tyr Ser
    130                 135                 140
Gly Asp Phe Val Val Ile Asp Pro Val Ala Thr Pro Phe Ala Lys Gly
145                 150                 155                 160
Glu Val Ile Ser Glu Val Val Tyr Asn Gln Ala Arg Asp Ala Tyr Gly
                165                 170                 175
Glu Asp Gly Phe Phe Ala Leu Thr Gly Val Glu Ala Ile Lys Glu Leu
            180                 185                 190
Leu Thr Arg Leu Asp Leu Glu Ala Ile Arg Ala Thr Leu Arg Asn Glu
        195                 200                 205
Leu Glu Ser Thr Ser Ser Glu Met Lys Arg Lys Val Val Lys Arg
    210                 215                 220
Leu Arg Leu Val Glu Asn Phe Ile Lys Ser Gly Asn Arg Pro Glu Trp
225                 230                 235                 240
Met Ile Leu Thr Val Ile Pro Val Leu Pro Pro Asp Leu Arg Pro Leu
                245                 250                 255
Val Ser Leu Glu Asn Gly Arg Pro Ala Val Ser Asp Leu Asn His His
            260                 265                 270
Tyr Arg Thr Ile Ile Asn Arg Asn Asn Arg Leu Glu Lys Leu Leu Lys
        275                 280                 285
Leu Asn Pro Pro Ala Ile Met Ile Arg Asn Glu Lys Arg Met Leu Gln
    290                 295                 300
Glu Ala Val Asp Ala Leu Phe Asp Ser Ser Arg Arg Ser Tyr Val Ser
305                 310                 315                 320
Ser Arg Val Gly Ser Met Gly Tyr Lys Lys Ser Leu Ser Asp Met Leu
                325                 330                 335
Lys Gly Lys Gln Gly Arg Phe Arg Gln Asn Leu Leu Gly Lys Arg Val
            340                 345                 350
Asp Tyr Ser Gly Arg Ser Val Ile Val Val Gly Pro Ser Leu Lys Leu
        355                 360                 365
His Gln Cys Gly Leu Pro Lys Lys Met Ala Leu Glu Leu Phe Lys Pro
    370                 375                 380
Phe Ile Cys Ser Lys Leu Lys Met Tyr Gly Ile Ala Pro Thr Val Lys
385                 390                 395                 400
Leu Ala Asn Lys Met Ile Gln Ser Glu Lys Pro Asp Val Trp Asp Val
                405                 410                 415
Leu Asp Glu Val Ile Lys Glu His Pro Ile Leu Leu Asn Arg Ala Pro
            420                 425                 430
Thr Leu His Arg Leu Gly Leu Gln Ala Phe Asp Pro Val Leu Ile Glu
        435                 440                 445
Gly Lys Ala Ile Gln Leu His Pro Leu Val Cys Ser Ala Phe Asn Ala
    450                 455                 460
Asp Phe Asp Gly Asp Gln Met Ala Val His Val Pro Leu Ser Gln Glu
465                 470                 475                 480
Ala Gln Leu Glu Ala Arg Val Leu Met Ser Thr Asn Asn Ile Leu
                485                 490                 495
```

-continued

```
Ser Pro Ser Asn Gly Arg Pro Ile Ile Val Pro Ser Lys Asp Ile Val
            500                 505                 510

Leu Gly Ile Tyr Tyr Leu Thr Leu Leu Glu Glu Asp Pro Glu Val Arg
            515                 520                 525

Glu Val Gln Thr Phe Ala Glu Phe Ser His Val Glu Tyr Ala Leu His
            530                 535                 540

Glu Gly Ile Val His Thr Cys Ser Arg Ile Lys Tyr Arg Met Gln Lys
545                 550                 555                 560

Ser Ala Ala Asp Gly Thr Val Ser Ser Glu Ile Val Glu Thr Thr Pro
                565                 570                 575

Gly Arg Leu Ile Leu Trp Gln Ile Phe Pro Gln His Lys Asp Leu Thr
            580                 585                 590

Phe Asp Leu Ile Asn Gln Val Leu Thr Val Lys Glu Ile Thr Ser Ile
            595                 600                 605

Val Asp Leu Val Tyr Arg Ser Cys Gly Gln Arg Glu Thr Val Glu Phe
            610                 615                 620

Ser Asp Lys Leu Met Tyr Trp Gly Phe Lys Tyr Ala Ser Gln Ser Gly
625                 630                 635                 640

Ile Ser Phe Gly Cys Lys Asp Met Ile Ile Pro Asp Thr Lys Ala Ala
                645                 650                 655

His Val Glu Asp Ala Ser Glu Lys Ile Arg Glu Phe Ser Ile Gln Tyr
            660                 665                 670

Gln Asp Gly Leu Ile Thr Lys Ser Glu Arg Tyr Asn Lys Val Val Asp
            675                 680                 685

Glu Trp Ser Lys Cys Thr Asp Leu Ile Ala Arg Asp Met Met Lys Ala
            690                 695                 700

Ile Ser Leu Cys Asp Glu Pro Ala Arg Ser Gly Ala Pro Asp Thr
705                 710                 715
```

(2) INFORMATION FOR SEQ ID NO:60:

(i) SEQUENCE CHARACTERISTICS:
        (A) LENGTH: 439 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:60:

```
Ile His Ser Ala Tyr Asn Met Leu His Asp Cys Ala Thr Ala Gln Cys
1               5                   10                  15

Asn Lys Glu Val Pro Arg Phe Met Asp Pro Asp Phe Thr Arg Arg Glu
            20                  25                  30

Val His Leu Gln Ile Ala Lys Val Cys Ala Ile Leu Val Asn Ala Ile
            35                  40                  45

Thr Met Ala Ser Cys Phe Val Thr Thr Leu Thr Glu Ala Ser Asp Ser
        50                  55                  60

Ala Ile Gly Glu Ala Asp Glu His Ser Ala Tyr His Ala Asn Met Ala
65                  70                  75                  80

Leu Ser Ala Tyr Val Asn Ala Lys Phe Ser Ala Leu Ser Arg Cys Leu
            85                  90                  95

Asn Tyr Ser Pro Gly Pro Glu Glu Thr Lys Arg Arg Lys Ala Ile Leu
            100                 105                 110

Arg Val Val Arg His Asn Ile Glu Leu Cys Asn Lys Val Ala Glu Leu
            115                 120                 125
```

```
Val Asp Pro Glu Ile Pro Tyr Cys Phe Arg Asp Arg Thr Val Ser Cys
    130                 135                 140

Leu Asn Ser Met Leu Asp Ala Val Gly Ser Thr Ser Ala Glu Cys Glu
145                 150                 155                 160

Glu Met Val Ser Asp Asn Asp Ser Ala Lys Asn Arg Leu Ala Leu Ala
                165                 170                 175

Lys Lys Ala Arg Thr Gly Phe Leu His His Phe Lys Thr Tyr Lys Ser
            180                 185                 190

Leu Gly Leu Ser Val Ala Phe Lys Ser Phe Arg His Asp Lys Tyr Val
        195                 200                 205

Gln Ala Leu Val Tyr Ala Ile Gly Ser Leu Phe Ser Met His Arg Val
    210                 215                 220

Tyr Ala Ser Thr Gly Asn Thr Gly His Val Val Ala Ser Lys Ile Glu
225                 230                 235                 240

His Cys Leu Gln Met Leu Leu Thr Leu Tyr Lys Tyr Lys Val Arg Arg
                245                 250                 255

Ala Gly Ala Ser Glu Tyr Thr Ala Gln Glu Leu Tyr Leu Asp Met Cys
            260                 265                 270

Thr Val Tyr Asp Glu Ile Gln Glu Cys Val Thr Arg Gly Leu Leu Leu
        275                 280                 285

Asn Pro Gln Thr Glu Val Gly Phe Cys Ser Ala Met Leu Gly Tyr Leu
    290                 295                 300

Ser Ala Met Ile Gly Ile Trp Glu Lys Lys Tyr Glu Arg Tyr Phe Asn
305                 310                 315                 320

Asn Ile Arg Gln Thr Glu Gly Ser Pro Ser Gln Pro Ser Thr Ser Arg
                325                 330                 335

Leu Gly Ser Ala Gly Ala Gly Ile Gly Gly Ser Gln Ala Ser Tyr Thr
            340                 345                 350

Leu Pro His Asp Pro Gly His Met Pro Ser Ser Pro Ser Gln Pro Ser
        355                 360                 365

Thr Ser Gly Leu Gly Gly Asn Pro Ala Gly Gln Gly Ala Leu Gln Ala
    370                 375                 380

Gln Ala Pro Cys Gly Pro Leu Gln Asp Tyr Ser Tyr Ala Gln Pro Ser
385                 390                 395                 400

Thr Ser Gly Leu Gly Gly Ala Ser Ser Thr Leu Glu Gly Ala Gln Val
                405                 410                 415

Val Ser Pro Arg Ser Gln Thr Pro Ser Asp Asp Glu Leu Glu Pro Pro
            420                 425                 430

Ser Arg Arg Ser Arg Ser Ala
        435
```

(2) INFORMATION FOR SEQ ID NO:61:

(i) SEQUENCE CHARACTERISTICS:
        (A) LENGTH: 752 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:61:

```
Met His Met Pro Arg Ile Phe Thr Thr Pro Val Met Ser Gly Tyr Ala
1                   5                   10                  15

Tyr Ser Gly Cys Ser Ser Ala Glu Tyr Lys Glu Thr Val Cys Asn Ser
                20                  25                  30
```

-continued

```
Ile Met Thr Asn Ser Arg Pro Tyr Ala Ala Cys Leu Gln Ala Ile Arg
        35                  40                  45

Gln Cys Met Leu Glu Leu Arg Asp Thr Phe Val Lys Leu Arg Gly Val
    50                  55                  60

Asp Val Val Phe Ala Ala Asp Lys Ile Asp Ser Ile Asn Ser Cys
65                  70                  75                  80

Ile Thr Ala Ala Glu Gly Ala Ser Ser Ala Glu Pro Gly Val Leu Tyr
                85                  90                  95

Ser Leu Ile Asn Arg Leu Tyr Asp Ala Leu Gln Asp Cys Ile Thr Ala
            100                 105                 110

Gln Cys Asn Lys Glu Val Pro Leu Phe Met Asp Gln Asp Phe Ile Lys
        115                 120                 125

Arg Lys Ala His Leu Gln Ile Gly Lys Ala Cys Ala Ile Ile Val Asn
    130                 135                 140

Val Ile Ala Ile Val Asn Cys Cys Ala Arg Thr Ile Ala Thr Arg Phe
145                 150                 155                 160

Thr Gly Ala Val Ser Ser Glu Arg Arg Asp Gly Ser Ala Ser His Thr
                165                 170                 175

Val Thr Ala Leu Ser Ala Tyr Cys Tyr Val Lys Phe Ser Ala Leu Ser
            180                 185                 190

Arg Cys Leu Asn Ser Ser Leu Asp Ser Glu Thr Glu Asn Ile Lys
        195                 200                 205

Ala Ile Leu Arg Val Val Arg His Asn Ile Glu Leu Cys Ser Lys Val
    210                 215                 220

Ala Glu Leu Val Glu Pro Asn Thr Pro Arg Phe Phe Arg His Arg Thr
225                 230                 235                 240

Glu Ala Cys Leu Asp Ser Val Ile Asp Ala Ile Glu Thr Ser Ala Ala
                245                 250                 255

Ala Cys Glu Ala Met Val Arg Asn Asn Glu Ser Ala Arg Leu Arg Leu
            260                 265                 270

Gly Leu Ser Arg Arg Ala Met Ala Asn Phe Leu Tyr Tyr Leu Glu Ala
        275                 280                 285

Tyr Val Glu Gly Leu Gly Val His Ser Phe Asp Leu Arg Leu Lys Arg
    290                 295                 300

Glu Arg Tyr Arg Gly Gly Ala Leu Val His Ala Val Gly Gly Leu Phe
305                 310                 315                 320

Leu Met Tyr Arg Val Tyr Ala Ser Thr Gly Asn Val Asp His Val Val
                325                 330                 335

Ala Gly Arg Ile Gly His Cys Leu Gln Ile Leu Cys Ala Leu Tyr Ser
            340                 345                 350

Arg Arg Arg Glu Leu Gly Ala Tyr Arg Ala Arg Lys Ser Phe Leu Asp
        355                 360                 365

Met Cys His Val Tyr Glu Glu Ile Asn Glu His Ile Thr Glu Asp Ala
    370                 375                 380

Leu Leu Ile Pro Gln Ile Glu Val Lys Trp Arg Asn Thr Ala Leu Arg
385                 390                 395                 400

Tyr Leu Ser Val Met Met Asn Ile Cys Asp Lys Lys Tyr Gly Arg Tyr
                405                 410                 415

Phe Asn Ala Val Glu Gln Thr Gly Ala Ala Pro Ser Gln Pro Ser Thr
            420                 425                 430

Ser Gly Leu Gly Ser Thr Ser Ala Gly Val Glu Gly Ala Gln Ala Ile
        435                 440                 445

Ser Val Pro Leu Arg Val Leu Glu Arg Ile Pro Ile Pro Tyr Gly Ala
```

-continued

```
            450                 455                 460
Pro Trp Asp Gln Pro Ser Thr Ser Gly Met Gly Gly Thr Ala Gly Thr
465                 470                 475                 480

Gly Ser Gln Gln Ala Ser His Ile Pro Pro His Asp Pro Gly Met Met
                485                 490                 495

Pro Tyr Ser Tyr Ala Gln Pro Ser Thr Leu Trp Asp Gln Pro Ser Thr
            500                 505                 510

Ser Gly Leu Gly Ser Ala Ala Gly Thr Gly Ser Gln Gln Ala Ser His
            515                 520                 525

Ile Pro Pro His Asp Pro Gly Met Met Pro Tyr Ser Tyr Ala Gln Pro
            530                 535                 540

Ser Thr Ser Trp Asp Gln Pro Ser Thr Ser Gly Leu Gly Ser Ala Ala
545                 550                 555                 560

Gly Met Gly Ser Gln Gln Ala Ser His Ile Pro Pro His Asp Pro Gly
                565                 570                 575

Met Met Pro Tyr Ser Tyr Ala Gln Pro Ser Thr Ser Trp Asp Gln Pro
            580                 585                 590

Ser Thr Ser Gly Leu Gly Ser Ala Ala Gly Met Gly Ser Gln Gln Ala
            595                 600                 605

Ser His Ile Pro Pro His Asp Pro Gly Met Met Pro Tyr Ser Tyr Ala
            610                 615                 620

Gln Pro Ser Thr Ser Trp Asp Gln Pro Ser Thr Ser Trp Asp Gln Pro
625                 630                 635                 640

Ser Thr Ser Gly Leu Gly Gly Thr Ala Gly Gln Gly Ala Gln Leu Val
                645                 650                 655

Pro Pro Pro Pro His Ile Ile Leu Arg Val Leu Glu Asn Val Pro Tyr
            660                 665                 670

Pro Ser Ser Gln Phe Ser Thr Ser Gly Leu Gly Gly Thr Ser Thr Gly
            675                 680                 685

Met Gly Arg Ser Gln Ala Pro Tyr Val Pro Pro Gln Asp Gln Gly Ile
            690                 695                 700

Met Pro Tyr Ser Trp Asp Gln Pro Ser Ala Ser Gly Leu Gly Gly Ala
705                 710                 715                 720

Ser Tyr Thr Leu Glu Glu Ala Gln Val Ser Ser His Arg Pro Arg Thr
                725                 730                 735

Pro Ser Asp Asp Asp Ser Glu Pro Pro Ser Lys Gln Ala Arg Arg Ala
            740                 745                 750

(2) INFORMATION FOR SEQ ID NO:62:

(i) SEQUENCE CHARACTERISTICS:
        (A) LENGTH: 110 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:62:

Met Tyr Thr Val Ser Asp Ser Glu Ser Ile Thr Ser Phe Val Thr Pro
1               5                   10                  15

Pro Met Leu Met Ala Asn Ile Ser Ser Thr Lys Arg Ser Gly Tyr Leu
                20                  25                  30

Leu Ser Leu Ser Val Glu Pro Ser Asp Phe Phe Thr Val Thr Phe Phe
            35                  40                  45

Leu Lys Glu Thr Pro Phe Thr Thr Asp Asn Ser Val Pro Phe Cys Ser
```

```
                    50                  55                  60
Phe Glu Arg Asn Ser Thr Ala Asn Ser Arg Ile Phe Phe Ile Arg Asn
 65                  70                  75                  80

Ala Leu Phe His Ser Ser Val Arg Ile Asp Leu Leu Ser Ser Ser Val
                 85                  90                  95

Leu Gly Leu Gly Gly Thr Thr Ser Val Thr Arg Thr Pro Lys
                100                 105                 110
```

(2) INFORMATION FOR SEQ ID NO:63:

(i) SEQUENCE CHARACTERISTICS:
        (A) LENGTH: 149 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:63:

```
Asp Gly Phe Pro Thr Ala Asp Glu Asn Ala Lys Val Val Lys Ala Phe
 1               5                  10                  15

Ile Pro Ser Cys Asn Gly Lys Ser Phe Thr Lys Leu Pro Asp Leu Ser
                20                  25                  30

Ser Pro Cys Ile Ser Lys Phe Val Lys Thr Pro Leu Ile Arg Ala Pro
             35                  40                  45

Asn Ile Ser Phe Ser Ser Phe Ser Asn Ala Pro Arg Leu Ile Ile Ser
 50                  55                  60

Phe Ala Phe Phe Thr Leu Leu Thr Ser Asn Ser Pro Ala Phe Cys Leu
 65                  70                  75                  80

Leu Ile Phe Glu Asp Ile Phe Ser Phe Ser Phe Ser Arg Ser Ser Leu
                 85                  90                  95

Val Ile Ser Cys Phe Leu Ile Thr Phe Met Ile Cys Gln Pro Thr Thr
                100                 105                 110

Leu Arg Asn Ile Ser Leu Thr Ser Pro Ser Phe Ser Ala Asn Thr Thr
                115                 120                 125

Phe Arg Thr Pro Thr Gly Arg Thr Ser Leu Glu Ile Leu Leu Ser Ala
            130                 135                 140

Ile Ser Ser Met Val
145
```

(2) INFORMATION FOR SEQ ID NO:64:

(i) SEQUENCE CHARACTERISTICS:
        (A) LENGTH: 590 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:64:

```
Leu Leu Tyr Ser Phe Gly Asn Leu Thr Ser Tyr Gly Arg Ser Val Met
 1               5                  10                  15

Arg Ser Arg Lys Ile Tyr Val Trp Val Val Met Ala Thr Val Leu Gly
                20                  25                  30

Ala Met Ala Phe Val Thr Phe Gly Ser Met Ile Pro Met Gly Lys Leu
             35                  40                  45

Ser Asn Ser Gly Asn Gly Gln Cys Val Ala Met Leu Gly Asn Lys Cys
 50                  55                  60
```

```
Leu Pro Leu Arg Asp Tyr Arg Ile Met Tyr Arg Asn Glu Leu Ala Glu
65                  70                  75                  80

Leu Glu Lys Met Leu Gln His Lys Leu Ser Asp Ala Gln Ile Asn Gln
                85                  90                  95

Phe Gly Ile Lys Glu Val Val Leu Lys Asn Met Ile Ala Asp Met Val
                100                 105                 110

Val Glu Lys Phe Ala His Asp Leu Gly Ile Arg Val Gly Ser Asn Ser
            115                 120                 125

Leu Arg Ser Leu Ile Lys Asn Ile Arg Ile Phe Gln Asp Ala Asn Gly
        130                 135                 140

Val Phe Asp Gln Glu Arg Tyr Glu Ala Val Leu Ala Asp Ser Gly Met
145                 150                 155                 160

Thr Glu Ser Ser Tyr Val Asn Lys Ile Arg Asn Ala Leu Pro Ser Thr
                165                 170                 175

Ile Leu Met Glu Cys Leu Phe Pro Asn Arg Ala Glu Leu His Ile Pro
                180                 185                 190

Tyr Tyr Asp Ala Leu Ala Lys Asp Val Val Leu Gly Leu Leu Gln His
            195                 200                 205

Arg Val Ala Asp Ile Val Glu Ile Ser Ser Asp Ala Val Asp Ile Ser
        210                 215                 220

Gly Ser Asp Ile Ser Asp Asp Glu Leu Gln Lys Leu Phe Glu Glu Gln
225                 230                 235                 240

Tyr Lys Asn Ser Leu Asn Phe Pro Glu Tyr Arg Ser Ala Asp Tyr Ile
                245                 250                 255

Ile Met Ala Glu Asp Asp Leu Leu Ala Asp Val Ile Val Ser Asp Gln
                260                 265                 270

Glu Val Asp Val Glu Ile Lys Asn Ser Glu Leu His Asp Gln Arg Asp
            275                 280                 285

Val Leu Asn Leu Val Phe Thr Asp Lys Asn Glu Ala Glu Leu Ala Tyr
        290                 295                 300

Lys Ala Tyr Gln Glu Gly Lys Ser Phe Glu Glu Leu Val Ser Asp Ala
305                 310                 315                 320

Gly Tyr Thr Ile Glu Asp Ile Ala Leu Asn Asn Ile Ser Lys Asp Val
                325                 330                 335

Leu Pro Val Gly Val Arg Asn Val Val Phe Ala Leu Asn Glu Gly Glu
                340                 345                 350

Val Ser Glu Met Phe Arg Ser Val Val Gly Trp His Ile Met Lys Val
            355                 360                 365

Ile Arg Lys His Glu Ile Thr Lys Glu Asp Leu Glu Lys Leu Lys Glu
        370                 375                 380

Lys Ile Ser Ser Asn Ile Arg Arg Gln Lys Ala Gly Glu Leu Leu Val
385                 390                 395                 400

Ser Asn Val Lys Lys Ala Asn Asp Met Ile Ser Arg Gly Ala Leu Leu
                405                 410                 415

Asn Glu Leu Lys Asp Met Phe Gly Ala Arg Ile Ser Gly Val Leu Thr
                420                 425                 430

Asn Phe Asp Met His Gly Leu Asp Lys Ser Gly Asn Leu Val Lys Asp
            435                 440                 445

Phe Pro Leu Gln Leu Gly Ile Asn Ala Phe Thr Thr Leu Ala Phe Ser
        450                 455                 460

Ser Ala Val Gly Lys Pro Ser His Leu Val Ser Asn Gly Asp Ala Tyr
465                 470                 475                 480

Phe Gly Val Leu Val Thr Glu Val Val Pro Pro Arg Pro Arg Thr Leu
```

```
                        485                 490                     495
Glu Glu Ser Arg Ser Ile Leu Thr Glu Glu Trp Lys Ser Ala Leu Arg
                500                 505                 510

Met Lys Lys Ile Arg Glu Phe Ala Val Glu Leu Arg Ser Lys Leu Gln
            515                 520                 525

Asn Gly Thr Glu Leu Ser Val Val Asn Gly Val Ser Phe Lys Lys Asn
        530                 535                 540

Val Thr Val Lys Lys Ser Asp Gly Ser Thr Asp Asn Asp Ser Lys Tyr
545                 550                 555                 560

Pro Glu Arg Leu Val Asp Glu Ile Phe Ala Ile Asn Ile Gly Gly Val
                565                 570                 575

Thr Lys Glu Val Ile Asp Ser Glu Ser Glu Thr Val Tyr Ile
                580                 585                 590

(2) INFORMATION FOR SEQ ID NO:65:

(i) SEQUENCE CHARACTERISTICS:
        (A) LENGTH: 245 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:65:

Gly Ser Cys Cys Tyr Glu Val Asp Gly Met Ala Lys Arg Phe Leu Asn
1               5                   10                  15

Asp Thr Glu Lys Lys Leu Leu Ser Leu Leu Lys Ser Val Met Gln His
            20                  25                  30

Tyr Lys Pro Arg Thr Gly Phe Val Arg Ala Leu Leu Ser Ala Leu Arg
        35                  40                  45

Ser Ile Ser Val Gly Asn Pro Arg Gln Thr Ala His Asp Leu Ser Val
    50                  55                  60

Leu Val Thr Gln Asp Phe Leu Val Glu Val Ile Gly Ser Phe Ser Thr
65                  70                  75                  80

Gln Ala Ile Ala Pro Ser Phe Leu Asn Ile Met Ala Leu Val Asp Glu
                85                  90                  95

Glu Ala Leu Asn His Tyr Asp Arg Pro Gly Arg Ala Pro Met Phe Ala
            100                 105                 110

Asp Met Leu Arg Tyr Ala Gln Glu Gln Ile Arg Arg Gly Asn Leu Leu
        115                 120                 125

Gln His Arg Trp Asn Glu Glu Thr Phe Ala Ser Phe Ala Asp Ser Tyr
    130                 135                 140

Leu Arg Arg Arg His Glu Arg Val Ser Ala Glu His Leu Arg Gln Ala
145                 150                 155                 160

Met Gln Ile Leu His Ala Pro Ala Ser Tyr Arg Val Leu Ser Thr Asn
                165                 170                 175

Trp Phe Leu Leu Arg Leu Ile Ala Ala Gly Tyr Val Arg Asn Ala Val
            180                 185                 190

Asp Val Val Asp Ala Glu Ser Ala Gly Leu Thr Ser Pro Arg Ser Ser
        195                 200                 205

Ser Glu Arg Thr Ala Ile Glu Ser Leu Leu Lys Asp Tyr Asp Glu Glu
    210                 215                 220

Gly Leu Ser Glu Met Leu Glu Thr Glu Lys Gly Val Met Thr Ser Leu
225                 230                 235                 240

Phe Gly Thr Val Leu
```

-continued

245

(2) INFORMATION FOR SEQ ID NO:66:

(i) SEQUENCE CHARACTERISTICS:
(A) LENGTH: 456 amino acids
(B) TYPE: amino acid
(C) STRANDEDNESS:
(D) TOPOLOGY: linear (ii) MOLECULE TYPE: protein (xi) SEQUENCE DESCRIPTION: SEQ ID NO:66:

```
Lys Ala Ile Pro Glu Ala Glu Lys Ile Phe Glu Lys Ala Met Asn Ile
 1               5                  10                  15

Ala Asp Lys Val Tyr Gly Ser Ala Ser Ser Glu Val Lys Ser Leu Phe
            20                  25                  30

Thr Cys Pro Asn Pro Glu Asp Ala Ser Thr Leu Val His Phe Val Ser
        35                  40                  45

Ser Asn Gly Thr Pro Asn Phe Asp Pro Leu Ala Lys Arg Val Leu Glu
    50                  55                  60

Glu Ala Tyr His Arg Tyr Gly Glu Glu Pro Phe Thr Asn Leu Asp Ile
65                  70                  75                  80

Ala Gly Asn Ala Pro Ile His Ala Ala Gln Lys Ser Thr Val Gly
                85                  90                  95

Val Phe Glu Gln Val Val Arg Cys Thr Pro Glu Ser Val Val Asn Gln
            100                 105                 110

Leu Ala Pro Asn Gly Lys Ala Pro Ile His Met Ile Val Glu Asp Glu
        115                 120                 125

Pro Ser His Lys Gly Val Ser Val Lys Leu Gln Met Leu Ile Glu Asn
    130                 135                 140

Val Arg Asn Ile Pro Ser Ile Asn Val Pro Ser Pro Val Thr Gly Glu
145                 150                 155                 160

Thr Pro Val Val Ala Ala Tyr Lys Gly Gly Asn Thr Glu Gly Val Lys
                165                 170                 175

Thr Met Leu Arg Cys Asn Ser Met Asp Val Asp Ala Arg Ser His Asp
            180                 185                 190

Gly Gly Thr Ile Ile His Tyr Ala Ala Lys Asp Gly Asn Leu Glu Ile
        195                 200                 205

Leu Gln Gln Ala Leu Gly Arg Lys Ser Ser Tyr Ser Lys Phe Pro Val
    210                 215                 220

Lys Asp Gly Val Pro Thr Pro Gly Val Tyr Ala Ile Arg Glu Ala Ser
225                 230                 235                 240

Gly Gly Lys Val Ser Leu Pro Ala Leu Asp Met Leu Met Arg Tyr Glu
                245                 250                 255

Pro Tyr Pro Gln His Val Ala Val Glu Ala Val Arg Lys Gly Ala Ala
            260                 265                 270

Asp Val Leu Arg His Leu Ile Thr Thr Glu Val Ile Ser Val Asn Glu
        275                 280                 285

Glu Ile Thr Thr Pro Glu Gly Lys Lys Thr Thr Leu Thr Ala Glu Ala
    290                 295                 300

Leu Thr Ser Gly Gln Tyr Ala Ala Val Lys Thr Leu Ile Lys Asn Ser
305                 310                 315                 320

Ala Asp Val Asn Ala Ser Pro Glu Pro Ala Ile Ser Val Gly Ile Gln
                325                 330                 335

Gly Gly Cys Phe Gln Gly Gly Lys Ala Ile Lys His Leu Lys Arg Val
```

-continued

```
                   340                 345                 350
Val Glu Ala Gly Ala His Ile Asn Thr Pro Thr Gly Ser Met Ser Pro
                355                 360                 365
Leu Ala Ala Ala Val Gln Val Ala Asn Glu Ala Ser Asn Leu Lys Glu
            370                 375                 380
Ala Asn Arg Ile Val Asn Phe Leu Leu Gln Arg Gly Ala Asp Leu Ser
385                 390                 395                 400
Ser Thr Asp His Thr Gly Thr Pro Ala Leu His Leu Ala Thr Ala Ala
                405                 410                 415
Gly Asn Gln Lys Thr Ala Arg Leu Leu Leu Asp Lys Gly Ala Pro Ala
                420                 425                 430
Thr Gln Arg Asp Ala Tyr Gly Lys Thr Ala Leu His Ile Ala Ala Ala
                435                 440                 445
Asn Gly Asp Gly Lys Leu Tyr Lys
            450                 455
```

(2) INFORMATION FOR SEQ ID NO:67:

(i) SEQUENCE CHARACTERISTICS:
        (A) LENGTH: 113 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:67:

```
Asp Gly Asn Thr Pro Leu His Thr Ala Ala Ser Ser Val Gly Lys Asn
1               5                   10                  15
Ala Leu Gly Asn Leu Asp Val Leu Cys Asp Lys Ala Leu Ile Ala Asp
                20                  25                  30
Val Asn Ala Lys Gly Pro Gly Gly Asn Thr Pro Leu His Ile Ala Thr
                35                  40                  45
Glu Arg Met Asp His Gln Lys Val Lys His Leu Leu Ser Arg Leu Ser
            50                  55                  60
Asp Ile Ser Val Ala Asn Asp Ala Gly Glu Thr Val Cys His Ile Val
65                  70                  75                  80
Ala Lys Gln Trp Pro Arg Arg Asp Val Leu Ser Tyr Ile Asp Lys Met
                85                  90                  95
Gln Glu Ala Val Ser Ser Asn Ile Glu Gly Asn Arg Ser Val Gln Arg
                100                 105                 110
His
```

(2) INFORMATION FOR SEQ ID NO:68:

(i) SEQUENCE CHARACTERISTICS:
        (A) LENGTH: 623 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:68:

```
Asp Glu Ala Pro Met Thr Leu Leu Leu Lys Gln Asn Pro Ser Lys Ala
1               5                   10                  15
Ser Val Ala Leu Leu Gly Ser Ala Ile Asp Phe Phe Leu Cys Arg Asp
                20                  25                  30
Arg Asn Ser His Pro Ala Arg Arg Arg Met Val Ile Leu Leu Ala Glu
```

-continued

```
            35                  40                  45
Gly Phe Thr Leu Arg Glu Gly Ser Ala Val Pro Pro Ala Leu Ile His
         50                  55                  60
Glu Asn Leu Thr Ser Pro Asp Leu Leu Ala Arg Ala Leu His Lys Thr
 65                  70                  75                  80
Ala Ser Asn Ser Thr Ala Phe Gln Gln Val Pro Phe Gln Leu Trp His
                 85                  90                  95
Ala Leu Ala Leu Ala Tyr Asn Ser Leu Pro Gly Lys Asn Gln Glu Glu
                100                 105                 110
Asp Leu Thr Asn Phe Val Leu Gly Cys Leu Asp Gly Val Ser Glu Asp
                115                 120                 125
Met Thr Ile Val Arg Glu Glu Asp Ser Thr Thr Phe Glu Val Gln Ser
    130                 135                 140
Tyr Thr Thr Phe Ser Arg Val His Ser Leu Leu Ala Ser Ala Pro Ser
145                 150                 155                 160
Ser Tyr Lys Asn Gly Ala Leu Thr Val His Glu Ser Cys Ile Phe Ser
                165                 170                 175
Ile Gln Asp Asn Ser Gly Val Pro Ile Ala Lys Val Lys Met Trp Val
                180                 185                 190
Glu Tyr Asp Ile Ala Pro Ser Thr Lys Ala Glu Gly Val Tyr Arg Thr
    195                 200                 205
Ala Val Lys Lys Val Lys Leu Val Leu Thr Glu Arg Asp Cys Arg Asp
    210                 215                 220
Val Arg Gln Gly Glu Pro Gly Ser Val Cys Ser Trp His Asn Ile Pro
225                 230                 235                 240
Lys Ala Leu Ala Lys His Tyr Val Arg Val Pro Glu Lys Pro Thr His
                245                 250                 255
Val Leu Tyr Ser Ala Cys Asn Leu Gln Arg His Asn Pro Arg Tyr Met
                260                 265                 270
Ala Arg Arg Val Phe Tyr Asp Val Ser Asp Ile Asp Glu Cys Ile Leu
    275                 280                 285
Arg Ala Tyr Ser Val Ile Ser Gly Met Pro Leu Glu Val Leu Glu Leu
    290                 295                 300
Ser Phe Cys Asn Thr Val Ile Ser Gln Glu Ala Ser Gly Val Phe Arg
305                 310                 315                 320
Val Val Val Arg Gly Val Val Gly Leu Val Gly Tyr Asp Lys Ser Ser
                325                 330                 335
Val Val Gln Gln Gly Ala Val Ser His Gly Arg Asp Ala Val Ser Lys
                340                 345                 350
Met Gly Val Cys Met Ser Phe Val Ala Ser Gln Ala His Asp Ala Cys
    355                 360                 365
Ala Thr Ile Leu Arg His Val Ala Val Thr Val Asn Thr Phe Gly Asn
    370                 375                 380
Val Leu Thr Leu Gly Gly Gly Ile Ser Leu Arg Asp Phe Leu Ala Gly
385                 390                 395                 400
Ser Ala Lys Asp Thr Asp Phe Ala Gly Gly His Ile Phe Asn Leu Ala
                405                 410                 415
Glu Glu Ile Val Ala His Gly Leu Ser Leu Trp Glu Asp Leu Gly Lys
                420                 425                 430
Arg His Arg Trp Ala Ser His Ser Val Pro Val Arg Gly Asp Cys Gly
    435                 440                 445
Ile Phe Ile Gln His Ser Asp Glu Ile Arg Glu Ile Leu Arg Ser Gln
    450                 455                 460
```

-continued

```
Pro Lys His Ala Ala Asn Ile Val Glu Lys Thr Gly Val Asn Thr Glu
465                 470                 475                 480

Asn Leu Arg Val Leu Leu Ser Ser Ile Leu Ser Asn Ser Ser Gly Ser
            485                 490                 495

Ser Leu Pro Val Glu Leu Ala Ala His Tyr Val Ala His Glu Gly Val
            500                 505                 510

Val Ala Asp Asn Gly Asp Ser Ala Arg Arg Leu Pro Val Asn Gln His
            515                 520                 525

Val Leu Glu Glu His Leu Val Tyr Arg Val Thr Ser Val Ser Gly Ile
            530                 535                 540

His Ile His Ala Cys Val Asp Tyr Val Val Glu Asp Ile Asp Thr Pro
545                 550                 555                 560

Gly Ser Val Lys Asp Leu Gly Leu Cys Ile Arg Asp Val Arg Ile Gly
                565                 570                 575

Thr Arg Val Ala Ser Ser Ala Glu Glu Val Cys Ser Ala Ile Gln Glu
                580                 585                 590

Lys Glu Gly Arg Ile Asp Arg Asn Asp Phe Ala Trp Phe Asn Val Asp
            595                 600                 605

Gln Ser Leu Val Glu Thr Ser Arg Ala Glu Phe Arg Ala Ala Ile
            610                 615                 620

(2) INFORMATION FOR SEQ ID NO:69:

(i) SEQUENCE CHARACTERISTICS:
        (A) LENGTH: 464 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:69:

Arg Ile His Met Arg Lys Glu Asn Ser Lys Ala Ala Tyr Cys Val Thr
1               5                   10                  15

Trp Arg Phe Lys Leu Arg Lys Lys Asn Thr His Asn Gly Ser Arg Arg
                20                  25                  30

Thr Val Ser Gly Ile Leu Asn Tyr Leu Arg Ala Leu Phe Phe Arg Ile
            35                  40                  45

Ile Ser Ile Phe Ser Thr Ser Ser Ala Val Ser Lys Ala Glu Asp
50                  55                  60

Glu Ala Asn Ser Val His Ile Cys Thr His Asn Ser Ser Asp Ala Ser
65                  70                  75                  80

Lys Asp Ser Lys Ala Lys His Lys Asp His Arg Pro Ser Ile Asp Val
            85                  90                  95

Ser Leu Lys Tyr Ser Gln Lys Lys Lys Trp Leu Glu Gly Ala Ser Gly
            100                 105                 110

Phe Ser Phe His Ser Ala Leu Cys Asp Ser Tyr Lys Asn Lys Ser Asn
            115                 120                 125

Leu Tyr Gly His Gln Phe Leu Ile Asp Met His Arg Cys Asp Trp Cys
130                 135                 140

Ile Asn Lys Thr Phe Tyr Pro Arg Gln Asn Val Ser Ala His Ile Ala
145                 150                 155                 160

Arg Leu Glu Arg Ser Ile Lys Ser Ser Ser Ile Thr Asn Leu Asn Leu
                165                 170                 175

Val Cys Gln Arg Thr Tyr Gly Val Ser Arg Gly Val Phe Leu Arg Arg
            180                 185                 190
```

```
Tyr Arg Glu Arg Ser Leu Ala Ile Ala Met Leu Gln Lys Met Phe Arg
            195                 200                 205

Asp Asp Arg His Gly Val Val Pro Asp Ile Arg Leu Leu Asp Glu Ile
    210                 215                 220

Ala Ser His Cys His Gln Gly Gly Leu Ser Ala Trp Val Cys Phe Asp
225                 230                 235                 240

Val Ile Trp Pro Ile Lys His Ala Leu Asp Lys Glu Tyr Phe Phe Ser
                245                 250                 255

Asp Ala Gly Ala Thr Leu Asn Leu Leu Asn Arg Ile Tyr Val Ser Ala
            260                 265                 270

Cys Ser Asn Ile Lys Gln Val Asp Ala Ile Thr Pro Glu Arg Ile Ala
    275                 280                 285

Val Cys Glu Asn Leu Asp Phe Leu Leu Lys Val Pro Gln Ser Thr Glu
290                 295                 300

Gly Glu Lys Thr Pro Ala Phe Lys Val Asn Thr Ala Leu Lys Tyr Glu
305                 310                 315                 320

Ile Ser Ile Gln Gly Glu Gly Arg Val Leu Tyr Asp Asn Cys Ser Leu
            325                 330                 335

Asn Leu Thr Ile Ile Thr Pro Pro Asp Cys Asn Ile Lys Thr Ser Pro
            340                 345                 350

Pro Leu Leu Phe Arg Val Cys Pro Pro Leu Gly Arg Leu Leu Leu Arg
        355                 360                 365

Leu Lys His Arg Phe Tyr Lys Arg Lys Val Phe Thr Pro Gln Asp Thr
        370                 375                 380

Arg Val Pro Asp Pro Thr Leu Val Arg Val Gln Arg Ile Pro Cys Ile
385                 390                 395                 400

Gly Met Asn Ile Thr Lys Leu Gln Tyr Ala Met Ala Pro Leu Pro Val
                405                 410                 415

Ser Pro Glu Glu Phe Phe Arg Asp Leu Val Lys Asn Ser Thr Ile Cys
            420                 425                 430

Gly Ile Tyr Ile Met Thr Ser Ser Leu Arg Lys Cys Ile Trp Gln Ser
        435                 440                 445

Leu Asn Pro Asn Met Leu Arg Leu Met Phe Leu Arg His Met Met Met
450                 455                 460

(2) INFORMATION FOR SEQ ID NO:70:

(i) SEQUENCE CHARACTERISTICS:
        (A) LENGTH: 378 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:70:

Ile Leu Arg Phe Ser Asp Asp Phe Pro Asp Ala Lys Val Ile Arg Leu
1               5                   10                  15

Glu Cys Asn Tyr Arg Ser Thr Ser Asn Ile Leu Ala Ser Ala Ser Ala
                20                  25                  30

Ile Ile Asp Asn Asn Lys Ser Arg Leu Lys Lys Thr Leu Trp Thr His
            35                  40                  45

Asn Gln Ala Gly Gln Lys Val Gly Leu Met Lys Phe Phe Asp Gly Arg
        50                  55                  60

Leu Glu Ala Gln Tyr Ile Ser Glu His Ile Lys Ser Ser Tyr Asp Tyr
65                  70                  75                  80
```

```
Lys Phe Ser Glu Thr Ala Val Leu Val Arg Ala Ser Phe Gln Thr Arg
                85                  90                  95

Val Phe Glu Glu Phe Phe Val Arg Tyr Gly Ile Pro Tyr Lys Ile Ile
            100                 105                 110

Gly Gly Thr Lys Phe Tyr Asp Arg Val Glu Ile Arg Asp Leu Val Ala
            115                 120                 125

Tyr Leu Lys Val Val Asn Pro Asn Asn Asp Ile Ala Phe Glu Lys
        130                 135                 140

Ile Ile Asn Lys Pro Lys Arg Lys Leu Gly Thr Ser Thr Val Asn Lys
145                 150                 155                 160

Leu Arg Ala Tyr Gly Arg Lys His Ser Ile Ser Leu Thr Glu Ala Gly
                165                 170                 175

His Ser Met Ile Lys Asp Gly Leu Leu Ser Asp Asn Thr Ser Asn Ile
            180                 185                 190

Leu Gln Asp Leu Leu Lys Gln Phe Asp Asp Trp Arg Glu Met Leu Ser
            195                 200                 205

Arg Asp Ser Ser Val Asn Val Leu Lys Ala Ile Ala His Asp Ser Gly
            210                 215                 220

Tyr Ile Glu Ser Leu Lys Lys Asp Gly Glu Ser Gly Leu Ser Arg Ile
225                 230                 235                 240

Glu Asn Ile Lys Glu Leu Phe Ser Ala Val Ser Gly Phe Asp Asp Val
                245                 250                 255

Ser Lys Phe Leu Glu His Ile Ser Leu Val Ala Glu Asn Asp Ser Leu
            260                 265                 270

Glu Glu Asp Asn Asn Tyr Val His Val Met Thr Leu His Ala Ala Lys
            275                 280                 285

Gly Leu Glu Phe Pro Leu Val Phe Leu Pro Gly Trp Glu Glu Gly Val
            290                 295                 300

Phe Pro His Glu Lys Ser Met Asn Asp Ile Thr Gly Asn Ala Leu Glu
305                 310                 315                 320

Glu Glu Arg Arg Leu Ala Tyr Val Gly Ile Thr Arg Ala Arg Glu Gln
                325                 330                 335

Leu Tyr Ile Ser Cys Ala Ala Met Arg Glu Ile Asn Asn Trp Ser Gln
            340                 345                 350

Ser Met Lys Met Ser Arg Phe Ile Lys Glu Leu Pro Arg Glu His Val
            355                 360                 365

Gln Val Leu His Asn Met Thr Gly Tyr Ala
            370                 375

(2) INFORMATION FOR SEQ ID NO:71:

(i) SEQUENCE CHARACTERISTICS:
        (A) LENGTH: 209 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:71:

Tyr Ile Asp Ser Leu Arg Ser His Ser Leu Leu Leu Lys Arg Lys Thr
1               5                   10                  15

Lys Gly Ile Arg Asp Ser Gly Ser Lys Glu Asp Glu Ala Asp Thr Val
            20                  25                  30

Tyr Leu Leu Ala Lys Glu Leu Ala Tyr Asp Val Val Thr Gly Gln Thr
        35                  40                  45
```

-continued

```
Asp Asn Leu Ala Ala Leu Ala Lys Thr Ser Gly Lys Asp Phe Val
    50                  55                  60
Lys Phe Ala Asn Ala Val Val Gly Ile Ser His Pro Asp Val Asn Lys
 65                  70                  75                  80
Lys Val Cys Ala Thr Arg Lys Asp Ser Gly Thr Arg Tyr Ala Lys
                 85                  90                  95
Tyr Ala Ala Thr Thr Asn Lys Ser Ser Asn Pro Glu Thr Ser Leu Cys
                100                 105                 110
Gly Asp Glu Gly Gly Ser Ser Gly Thr Asn Asn Thr Gln Glu Phe Leu
                115                 120                 125
Lys Glu Phe Val Ala Lys Thr Leu Val Glu Asn Glu Ser Lys Asn Trp
    130                 135                 140
Pro Thr Ser Ser Gly Thr Gly Leu Lys Thr Asn Asp Asn Ala Lys Ala
145                 150                 155                 160
Val Ala Thr Asp Leu Val Ala Leu Asn Arg Asp Glu Lys Thr Ile Val
                165                 170                 175
Ala Gly Leu Leu Ala Lys Thr Ile Glu Gly Gly Glu Val Val Glu Ile
                180                 185                 190
Arg Ala Val Ser Ser Thr Ser Val Met Ala Leu Glu Leu Arg Val Cys
                195                 200                 205
Trp
```

(2) INFORMATION FOR SEQ ID NO:72:

(i) SEQUENCE CHARACTERISTICS:
       (A) LENGTH: 261 amino acids
       (B) TYPE: amino acid
       (C) STRANDEDNESS:
       (D) TOPOLOGY: linear (ii) MOLECULE TYPE: protein (xi) SEQUENCE DESCRIPTION: SEQ ID NO:72:

```
Lys Lys Ser Ile Ile Arg Glu Asp Glu Val Asp Thr Val Tyr Leu Leu
  1               5                  10                  15
Ala Lys Glu Leu Ala Tyr Asp Val Val Thr Gly Gln Thr Asp Lys Leu
                 20                  25                  30
Thr Ala Ala Leu Ala Lys Thr Ser Gly Lys Asp Ile Val Gln Phe Ala
                 35                  40                  45
Lys Ala Val Gly Val Ser His Pro Ser Ile Asp Gly Lys Val Cys Arg
    50                  55                  60
Thr Lys Arg Lys Ala Gly Asp Ser Ser Gly Thr Tyr Ala Lys Tyr Gly
 65                  70                  75                  80
Glu Glu Thr Asp Asn Asn Thr Ser Gly Gln Ser Thr Val Ala Val Cys
                 85                  90                  95
Gly Glu Lys Ala Gly His Asn Ala Asn Gly Ser Gly Thr Val Gln Ser
                100                 105                 110
Leu Lys Asp Phe Val Arg Glu Thr Leu Lys Ala Asp Gly Asn Arg Asn
    115                 120                 125
Trp Pro Thr Ser Arg Glu Lys Ser Gly Asn Thr Asn Thr Lys Pro Gln
    130                 135                 140
Pro Asn Asp Asn Ala Lys Ala Val Ala Lys Asp Leu Val Gln Glu Leu
145                 150                 155                 160
Asn His Asp Glu Lys Thr Ile Val Ala Gly Leu Leu Ala Lys Thr Ile
                165                 170                 175
```

```
Glu Gly Gly Glu Val Val Glu Ile Arg Ala Val Ser Ser Thr Ser Val
            180                 185                 190

Met Val Asn Ala Cys Tyr Asp Leu Leu Ser Glu Gly Leu Gly Val Val
            195                 200                 205

Pro Tyr Ala Cys Val Gly Leu Gly Gly Asn Phe Val Gly Val Val Asp
            210                 215                 220

Gly His Ile Thr Ile Arg Trp Ala Ser Thr Leu Tyr Ala His Ser Lys
225                 230                 235                 240

Ser Leu Gly Lys Ile Gly Ala Ala Ser Leu Arg Asn Arg Leu Arg Ser
            245                 250                 255

Ala Ile Leu His Thr
            260
```

(2) INFORMATION FOR SEQ ID NO:73:

(i) SEQUENCE CHARACTERISTICS:
        (A) LENGTH: 530 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:73:

```
Leu Leu Tyr Ser Phe Gly Asn Leu Thr Ser Tyr Gly Arg Ser Val Met
1               5                   10                  15

Arg Ser Arg Lys Ile Tyr Val Trp Val Met Ala Thr Val Leu Gly
            20                  25                  30

Ala Met Ala Phe Val Thr Phe Gly Ser Met Ile Pro Met Gly Lys Leu
            35                  40                  45

Ser Asn Ser Gly Asn Gly Gln Cys Val Ala Met Leu Gly Asn Lys Cys
50                  55                  60

Leu Pro Leu Arg Asp Tyr Arg Ile Met Tyr Arg Asn Glu Leu Ala Glu
65                  70                  75                  80

Leu Glu Lys Met Leu Gln His Lys Leu Ser Asp Ala Gln Ile Asn Gln
            85                  90                  95

Phe Gly Ile Lys Glu Val Val Leu Lys Asn Met Ile Ala Asp Met Val
            100                 105                 110

Val Glu Lys Phe Ala His Asp Leu Gly Ile Arg Val Gly Ser Asn Ser
            115                 120                 125

Leu Arg Ser Leu Ile Lys Asn Ile Arg Ile Phe Gln Asp Ala Asn Gly
            130                 135                 140

Val Phe Asp Gln Glu Arg Tyr Glu Ala Val Leu Ala Asp Ser Gly Met
145                 150                 155                 160

Thr Glu Ser Ser Tyr Val Asn Lys Ile Arg Asn Ala Leu Pro Ser Thr
            165                 170                 175

Ile Leu Met Glu Cys Leu Phe Pro Asn Arg Ala Glu Leu His Ile Pro
            180                 185                 190

Tyr Tyr Asp Ala Leu Ala Lys Asp Val Val Leu Gly Leu Leu Gln His
            195                 200                 205

Arg Val Ala Asp Ile Val Glu Ile Ser Ser Asp Ala Val Asp Ile Ser
            210                 215                 220

Gly Ser Asp Ile Ser Asp Asp Glu Leu Gln Lys Leu Phe Glu Glu Gln
225                 230                 235                 240

Tyr Lys Asn Ser Leu Asn Phe Pro Glu Tyr Arg Ser Ala Asp Tyr Ile
            245                 250                 255
```

-continued

```
Ile Met Ala Glu Asp Asp Leu Leu Ala Asp Val Ile Val Ser Asp Gln
            260                 265                 270

Glu Val Asp Val Glu Ile Lys Asn Ser Glu Leu His Asp Gln Arg Asp
        275                 280                 285

Val Leu Asn Leu Val Phe Thr Asp Lys Asn Glu Ala Glu Leu Ala Tyr
    290                 295                 300

Lys Ala Tyr Gln Glu Gly Lys Ser Phe Glu Glu Leu Val Ser Asp Ala
305                 310                 315                 320

Gly Tyr Thr Ile Glu Asp Ile Ala Leu Asn Asn Ile Ser Lys Asp Val
                325                 330                 335

Leu Pro Val Gly Val Arg Asn Val Val Phe Ala Leu Asn Glu Gly Glu
            340                 345                 350

Val Ser Glu Met Phe Arg Ser Val Val Gly Trp His Ile Met Lys Val
        355                 360                 365

Ile Arg Lys His Glu Ile Thr Lys Glu Asp Leu Glu Lys Leu Lys Glu
    370                 375                 380

Lys Ile Ser Ser Asn Ile Arg Arg Gln Lys Ala Gly Glu Leu Leu Val
385                 390                 395                 400

Ser Asn Val Lys Lys Ala Asn Asp Met Ile Ser Arg Gly Ala Leu Leu
                405                 410                 415

Asn Glu Leu Lys Asp Met Phe Gly Ala Arg Ile Ser Gly Val Leu Thr
            420                 425                 430

Asn Phe Asp Met His Gly Leu Asp Lys Ser Gly Asn Leu Val Lys Asp
        435                 440                 445

Phe Pro Leu Gln Leu Gly Ile Asn Ala Phe Thr Thr Leu Ala Phe Ser
    450                 455                 460

Ser Ala Val Gly Lys Pro Ser His Leu Val Ser Asn Gly Asp Ala Tyr
465                 470                 475                 480

Phe Gly Val Leu Val Thr Glu Val Val Pro Pro Arg Pro Arg Thr Leu
                485                 490                 495

Glu Glu Ser Arg Ser Ile Leu Thr Glu Glu Trp Lys Ser Ala Leu Arg
            500                 505                 510

Met Lys Lys Ile Arg Glu Phe Ala Val Glu Leu Arg Ser Lys Leu Gln
        515                 520                 525

Asn Gly
    530
```